(12) United States Patent
Pan et al.

(10) Patent No.: US 9,096,656 B2
(45) Date of Patent: *Aug. 4, 2015

(54) FACTOR VIII CONJUGATES

(71) Applicant: Bayer HealthCare LLC, Whippany, NJ (US)

(72) Inventors: Clark Q. Pan, Castro Valley, CA (US); John E. Murphy, Berkeley, CA (US); Baisong Mei, Danville, CA (US); Jonathan S. Strauss, Walnut Creek, CA (US); Hendri Tjandra, Union City, CA (US); Jianmin Chen, Concord, CA (US); Thomas Barnett, Chapel Hill, NC (US); Liang Tang, Richmond, CA (US); Deqian Wang, Concord, CA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/748,983

(22) Filed: Jan. 24, 2013

(65) Prior Publication Data

US 2013/0274445 A1  Oct. 17, 2013

Related U.S. Application Data

(63) Continuation of application No. 12/407,703, filed on Aug. 13, 2009, which is a continuation of application No. 11/273,896, filed on Nov. 14, 2005, now Pat. No. 7,632,921.

(60) Provisional application No. 60/627,277, filed on Nov. 12, 2004.

(51) Int. Cl.
*C07K 17/08* (2006.01)
*A61K 47/48* (2006.01)
*A61K 38/00* (2006.01)
*C07K 14/755* (2006.01)

(52) U.S. Cl.
CPC .......... *C07K 17/08* (2013.01); *A61K 47/48215* (2013.01); *C07K 14/755* (2013.01); *A61K 38/00* (2013.01); *C07K 2319/00* (2013.01)

(58) Field of Classification Search
CPC ................................ C07K 14/75; A61K 38/03
See application file for complete search history.

(56) References Cited

U.S. PATENT DOCUMENTS

| 4,970,300 A | 11/1990 | Fulton et al. |
| 5,171,844 A | 12/1992 | van Ooyen et al. |

(Continued)

FOREIGN PATENT DOCUMENTS

| EP | 690126 | 1/1996 |
| EP | 786474 B1 | 7/1997 |

(Continued)

OTHER PUBLICATIONS

Adair F, et al. "The immunogenicity of Therapeutic Proteins," BioPharm, vol. 15, No. 2, 2002, pp. 30-36.

(Continued)

*Primary Examiner* — Alexander Kim
(74) *Attorney, Agent, or Firm* — Buchanan Ingersoll & Rooney

(57) ABSTRACT

This invention relates to Factor VIII muteins that are covalently bound, at a predefined site that is not an N-terminal amine, to one or more biocompatible polymers such as polyethylene glycol. The mutein conjugates retain FVIII procoagulant activity and have improved pharmacokinetic properties.

20 Claims, 52 Drawing Sheets

(56) References Cited

U.S. PATENT DOCUMENTS

| | | | |
|---|---|---|---|
| 5,422,260 | A | 6/1995 | Kaufman et al. |
| 5,451,521 | A | 9/1995 | Kaufman et al. |
| 5,766,897 | A | 6/1998 | Braxton |
| 5,919,766 | A | 7/1999 | Österberg et al. |
| 5,925,739 | A | 7/1999 | Spira et al. |
| 5,972,885 | A | 10/1999 | Spira et al. |
| 6,037,452 | A | 3/2000 | Minamino et al. |
| 6,048,720 | A | 4/2000 | Dalborg et al. |
| 6,251,632 | B1 | 6/2001 | Lillicrap et al. |
| 6,316,226 | B1 | 11/2001 | Van Ooyen et al. |
| 6,346,513 | B1 | 2/2002 | Van Ooyen et al. |
| 6,753,165 | B1 | 6/2004 | Cox et al. |
| 6,759,216 | B1 | 7/2004 | Lollar |
| 6,770,744 | B2 | 8/2004 | Lollar |
| 6,919,311 | B2 | 7/2005 | Lenting et al. |
| 6,930,087 | B2 | 8/2005 | Baru et al. |
| 7,033,791 | B2 | 4/2006 | Lollar |
| 7,138,505 | B1 | 11/2006 | Kuo et al. |
| 7,199,223 | B2 | 4/2007 | Bossard et al. |
| 7,205,278 | B2 | 4/2007 | Griffin et al. |
| 7,211,559 | B2 | 5/2007 | Saenko et al. |
| 7,645,860 | B2 | 1/2010 | Turecek et al. |
| 7,683,158 | B2 | 3/2010 | Siekmann et al. |
| 7,858,749 | B2 | 12/2010 | Bossard et al. |
| 7,863,421 | B2 | 1/2011 | Bossard et al. |
| 2002/0182670 | A1 | 12/2002 | Lollar |
| 2003/0077752 | A1 | 4/2003 | Cho et al. |
| 2003/0125232 | A1 | 7/2003 | Griffin et al. |
| 2004/0180054 | A1 | 9/2004 | Kim et al. |
| 2004/0235734 | A1 | 11/2004 | Bossard et al. |
| 2004/0248785 | A1 | 12/2004 | Saenko et al. |
| 2005/0107297 | A1 | 5/2005 | Holmes et al. |
| 2005/0118684 | A1 | 6/2005 | Lollar |
| 2005/0123997 | A1 | 6/2005 | Lollar |
| 2005/0176108 | A1 | 8/2005 | Kim et al. |
| 2005/0256304 | A1 | 11/2005 | Jones et al. |
| 2005/0288490 | A1 | 12/2005 | Nakamoto et al. |
| 2006/0073113 | A1 | 4/2006 | Nakamoto et al. |
| 2006/0160994 | A1 | 7/2006 | Lenting et al. |
| 2010/0120689 | A1 | 5/2010 | Bossard et al. |
| 2010/0125049 | A1 | 5/2010 | Bossard et al. |
| 2010/0130427 | A1 | 5/2010 | Bossard et al. |

FOREIGN PATENT DOCUMENTS

| | | | |
|---|---|---|---|
| EP | 808901 | | 11/1997 |
| EP | 1502921 | | 2/2005 |
| WO | WO-90/12874 | | 11/1990 |
| WO | WO-94/15625 | | 7/1994 |
| WO | WO-9511987 | A1 | 5/1995 |
| WO | WO 96/41813 | | 12/1996 |
| WO | WO-97/03195 | | 1/1997 |
| WO | WO-97/11957 | A1 | 4/1997 |
| WO | WO 00/42175 | | 7/2000 |
| WO | WO-00/71714 | | 11/2000 |
| WO | WO-02/098454 | | 12/2002 |
| WO | WO-03/031598 | | 4/2003 |
| WO | WO 2004/060965 | A2 | 7/2004 |
| WO | WO 2004/060966 | A2 | 7/2004 |
| WO | WO 2004/063250 | | 7/2004 |
| WO | WO-2004/075923 | | 9/2004 |
| WO | WO 2004075923 | * 9/2004 ............ A61K 47/48 |
| WO | WO-2005/000360 | A1 | 1/2005 |
| WO | WO-2005/046583 | | 5/2005 |
| WO | WO-2005/055930 | | 6/2005 |
| WO | WO-2006/027111 | A1 | 3/2006 |
| WO | WO-2006/103298 | | 10/2006 |

OTHER PUBLICATIONS

Dalborg J, et al. "Bioavailability of B-Domain Deleted Recombinant Factor VIII Conjugated with Monomethoxy polyethylene glycol," XXIII International Congress of the World Federation of Hemophilia. The Hague, The Netherlands, May 17-21, 1998. Abstracts. Haemophilia, vol. 4, No. 3, 1998, p. 163.

Ferreira J, Therapeutic Proteins: Present and Future Perspectives, Revista Portuguesa de Farmacia, vol. 49, No. 3, 1999, pp. 131-140. Abst.

Kleinberg M, et al., "Current and Future Considerations for the New Classes of Biologicals," American Journal of Health-System Pharmacy, vol. 61, No. 7, pp. 695-708.

Nucci ML, et al. "The Therapeutic Value of Poly(ethylene glycol)-Modified Proteins," Advanced Drug Delivery Reviews, vol. 6, No. 2, 1991, pp. 133-151.

Oguma Y, et al. "Studies on the Stability and Oral Administration of the Factor VIII and IX Concentrates," The Japanese Journal of Clinical Hematology, vol. 29, No. 5, 1988, pp. 655-661.

Sakuragawa N, et al. "Stability of Modified Factor-VIII Concentrate by Polyethylene Glycol," Ricerca in Clinica e in Laboratorio, vol. 16, No. 1, 1986, p. 113.

Sakuragawa N, et al. "Absorbability of Factor VIII or IX Concentrates Preparation Using Beagles," Acta Medica et Biologica, vol. 34, No. 3, 1986, pp. 77-84.

Schellekens H, et al., "Biopharmaceutical Molecules are Not Created Equally," The Pharmaceutical Journal, vol. 268, No. 7187, 2002, pp. 300-301.

Throm S, "Activities of the CPMP," Pharmazeutische Industrie, vol. 64, No. 8, 2002, pp. 757-763 (translation not available).

Fee C, "Size-Exclusion Reaction . . . Protein PEGylation", in Biotechnology and Bioengineering, vol. 82, No. 2. Apr. 20, 2003, Publisher: Wiley Periodicals, pp. 200-206.

Saenko, E., et al., "Role of the Low Density Lipoprotein-Related Protein Receptor in Mediation of Factor VIII Catabolism", The Journal of Biological Chemistry, vol. 274, No. 53, 1999, pp. 37685-37692.

Fay, P. J., et al., "Human Factor VIIIa Subunit Structure", The Journal of Biological Chemistry, vol. 266, No. 14, 1991, pp. 8957-8962.

Bovenschen, N., et al., "Low Density Lipoprotein Receptor-Related Protein and Factor IXa Share Structural Requirements for Binding to the A3 Domain of Coagulation Factor VIII", The Journal of Biological Chemistry, vol. 278, No. 11, 2003, pp. 9370-9377.

Jacquemin, M., et al., "A Novel Cause of Mild/Moderate Hemophilia A: Mutations Scattered in the Factor VIII C1 Domain Reduce Factor VIII Binding to von Willebrand Factor", Blood, vol. 96, No. 3, 2000, pp. 958-965.

Barrow, R., et al, "Reduction of the Antigenicity of Factor VIII Toward Complex Inhibitory Antibody Plasmas Using Multiply-Substituted Hybrid Human/Porcine Factor VIII Molecules", Blood, vol. 95, No. 2, 2000, pp. 564-568.

Regan, L., et al., "Activated Protein C-Catalyzed Proteolysis of Factor VIIIa Alters Its Interactions Within Factor Xase", The Journal of Biological Chemistry, vol. 271, No. 8, 1996, pp. 3982-3987.

Lenting, P., et al., "The Light Chain of Factor VIII Comprises a Binding Site for Low Density Lipoprotein Receptor-Related Protein", The Journal of Biological Chemistry, vol. 274, No. 34, 1999, pp. 23734-23739.

Lenting, P., et al., "The Sequence Glu811-Lys1818 of Human Blood Coagulation Factor VIII Comprises a Binding Site for Activated Factor IX", The Journal of Biological Chemistry, vol. 271, No. 4, 1996, pp. 1935-1940.

Lubin, I., et al., "Analysis of the Human Factor VIII A2 Inhibitor Epitope by Alanine Scanning Mutagenesis", The Journal of Biological Chemistry, vol. 272, No. 48, 1997, pp. 30191-30195.

Gilbert, G., et al., "Four Hydrophobic Amino Acids of the Factor VIII C2 Domain Are Constituents of Both the Membrane-Binding and von Willebrand Factor-Binding Motifs", The Journal of Biological Chemistry, vol. 277, No. 8, 2002, pp. 6374-6381.

Scandella, D., et al., "Localization of Epitopes for Human Factor VIII Inhibitor Antitodies by Immunoblotting and Antibody Neutralization", Blood, vol. 74, No. 5, 1989, pp. 1618-1626.

Foster, P., et al., "An Immunogenic Region within Residues Val1670-Glu1684 of the Factor VIII Light Chain Induces Antibodies Which Inhibit Binding of Factor VIII to von Willebrand Factor", The Journal of Biological Chemistry, vol. 263, No. 11, 1988, pp. 5230-5234.

Lubin, I., et al., "Elimination of a Major Inhibitor Epitope in Factor VIII", The Journal of Biological Chemistry, vol. 269, No. 12, 1994, pp. 8639-8641.

(56) References Cited

OTHER PUBLICATIONS

Scandella, D., et al., "A Recombinant Factor VIII A2 Domain Polypeptide Quantitatively Neutralizes Human Inhibitor Antibodies That Bind to A2", Blood, vol. 82, No. 6, 1993, pp. 1767-1775.
Sarafanov, A., "Cell Surface Heparan Sulfate Proteoglycans Participate in Factor VIII Catabolism Mediated by Low Density Lipoprotein Receptor-Related Protein", The Journal of Biological Chemistry, vol. 276, No. 15, 2001, pp. 11970-11979.
Parker, E., at al., "Reduction of the Inhibitory Antibody Response to Human Factor VIII in Hemophilia A Mice by Mutagenesis of the A2 Domain B-Cell Epitope", Blood, vol. 104, No, 3, 2004, pp. 704-710.
Scandella, D., et al., "Epitope Mapping of Human Factor VIII Inhibitor Antibodies by Deletion Analysis of Factor VIII Fragments Expressed in *Escherichia coli*", Proc. Natl. Acad. Sci. USA, vol. 85, 1988, pp. 6152-6156.
Nogami, K., et al., "Identification of a Factor Xa-Interactive Site Within Residues 337-372 of the Factor VIII Heavy Chain", The Journal of Biological Chemistry, vol. 279, No. 16, 2004, pp. 15763-15771.
Pittman, D., et al., "Proteolytic Requirements for Thrombin Activation of Anti-Hemophilic Factor (Factor VIII)", *Proc. Natl. Acad. Sci. USA*, vol. 85, 1988, pp. 2429-2433.
Healy, J., et al., "Residues 484-508 Contain a Major Determinant of the Inhibitory Epitope in the A2 Domain of Human Factor VIII", The Journal of Biological Chemistry, vol. 270, No. 24, 1995, pp. 14505-14509.
Fulcher, C., et al., "Localization of Human Factor FVIII Inhibitor Epitopes to Two Polypeptide Fragments", Proc. Natl. Acad. Sci. USA, vol. 82, 1985, pp. 7728-7732.
McMullen, B., et al., "Locations of Disulfide Bonds and Free Cysteines in the Heavy and Light Chains of Recombinant Human Factor VIII (Antihemophilic Factor A)", Protein Science, vol. 4, 1995, pp. 740-746.
Fay, P. , et al., "Factor VIIIa A2 Subunit Residues 558-565 Represent a Factor IXa Interactive Site", The Journal of Biological Chemistry, vol. 269, No. 32, 1994, pp. 20522-20527.
Spiegel. P. C., et al., "Surface-Exposed Hemophilic Mutations Across the Factor VIII C2 Domain Have Variable Effects on Stability and Binding Activities", The Journal of Biological Chemistry, vol. 279, No. 51. 2004, pp. 56391-56398.
Stoilova-McPhie, S., et al., "3-Dimensional Structure of Membrane-Bound Coagulation Factor VII: Modeling of the Factor VIII Heterodimer Within a 3-Dimensional Density Map Derived by Electron Crystallography", Blood, vol. 99, No. 4, 2002, pp. 1215-1223.
Gruppo, R.A. et al. "Comparative effectiveeness of full-length and B-domain deleted factor VIII for prophylaxis—a meta analysis", Haemophilia, vol. 4 2003, pp. 251-260.
Bovenschen, N. et al. "LDL receptor cooperates with LDL receptor-related protein in regulating plasma levels of coagulation factor VIII in vivo", Blood, vol. 106, No. 3, 2005, pp. 906-912.
Harris, J., et al., "Pegylation a Novel Process for Modifying Pharmacokinetics", Clin Pharmacokinet, vol. 40, No. 7, 2001, pp. 539-551.
Wang, W. et al., "Coagulation factor VIII: structure and stability", International Journal of Pharaceulics, vol. 259, 2003, pp. 1-15.
Kochendoerfer, G., " Site-specific polymer modification of therapeutic proteins", Current Opinion in Chemical Biology, vol. 9, 2005, pp. 555-560.
Scandella, D., at al, "A Soluble Recombinant Factor VIII Fragment Containing the A2 Domain Binds to Some Human Anti-Factor VIII Antibodies that Are not Detected by Immunoblotting", Thrombosis and Haemostasis, vol. 67, No. 6, 1992, pp. 665-671.
Rostin, J., et al., "B-Domain Deleted Recombinant Coagulation Factor VIII Modified with Monomethoxy Polyethylene Glycol", Bioconjugate Chem., vol. 11, 2000, pp. 387-396.
Goodson, R.et al., "Site-Directed Peglation of Recombinant Interleukin-2 at its Glycosylation Site", Bio/Technology, vol. 8, 1900, pp. 343-346.

Sakuragawa, N. et al. Studies on the Stability of Factor VIII Modified by Polyethylene Glycol. *Acta Medica et Biologica,* 36(1), pp. 1-6 (1988). (Abstract only).
Veronese, F. M., "Peptide and Protein PEGylation—a Review of Problems and Solutions", Biomaterials, Elsevier Science Publishers BV, Barking, GB (2001), No. 5, vol. 22, p. 405-417.
Kochendoerfer, G., "Chemical and Biological Properties of Polymer-Modified Proteins", Expert Opinion on Biological Therapy, (2003), vol. 3, No. 8, pp. 1253-1261.
Extended European Search Report (including suppl. European Search Report and the European search opinion) for EP App. 05849392.5 dated Dec. 1, 2008 (5 pages).
Guo et al., "Protein Tolerance to Random Amino Acid Change", Prox. Natl. Acad. Sci. USA, (2004), vol. 101, pp. 9205-9210.
Lazar, et al., Transforming Growth Factor Alpha: Mutation of Aspartic Acid 47 and Leucine 48 Results in Different Biological Activities, Mol. Cell. Biol., (1998), vol. 8, pp. 1247-1252.
Hill et al., Functional Analysis of Conserved Histidines in ADP-Glucose Pyrophosphorylase from *Escherichia coli,* Biochem, Biophys, Res. Comm., (1998), vol. 244, pp. 573-577.
Benhar, I., et al., "Pseudomonas Exotoxin A Mutants: Replacement of Surface-Exposed Residues in Domain III with Cysteine Residues That Can Be Modified with Polyethylene Glycol in a Site-Specific Manner," The Journal of Biological Chemistry, (May 6, 1994), vol. 109, No. 18, pp. 13398-13404.
Tsutsumi, Y., et al., "Site-specific chemical modification with polyethylene glycol of recombinant immunotoxin anti-Tac(Fv)-PE38 (LMB-2) improves antitumor activity and reduces animal toxicity and immunogenicity," PNAS, (Jul. 18, 2000), vol. 97, No. 15, pp. 8548-8553.
Yang, K., et al., "Tailoring structure-function and pharmacokinetic properties of single-chain Fv proteins by site-specific PEGylation," Protein Engineering. (2003), vol. 16, No. 10,—pp. 761-770.
Lenting, P., et al., "The Life Cycle of Coagulation Factor VIII in View of its Structure and Function", Blood, 1998, vol. 92, No. 11, pp. 3983-3996.
He et al., "Site-Directed Polyethylene Glycol Modification of Trichosanthin: Effects on its Biological Activities, Pharmacokinetics, and Antigenicity", Life Sciences, 1999, vol. 64, No. 14, pp. 1163-1175.
Kuan et al "Pseudomonas Exotoxin A Mutants: Replacement of Surface Exposed Residues in Domain II with Cysteine Residues that can be Modified with Polyethylene Glycol in a Site-Directed Manner", The Journal of Biological Chemistry, 1994, vol. 269, No. 10, Issue of Mar. 11, pp. 7610-7616.
Brinkhous et al., "Purified human factor VIII procoagulant protein: Comparative hemostatic response after infusions into hemophilic and von Willebrand disease dogs", Proc. Natl. Acad. Sci. USA, 1985, vol. 82, pp. 8752-8756.
Bovenschen et al., "The B domain of coagulation factor VIII interacts with the asialoglycoprotein receptor", Journal of Thrombosis and Haemostasis, 2005, vol. 3, pp. 1257-1265.
Lind et al., "Novel forms of B-domain-deleted recombinant factor VIII molecules", Construction and biochemical characterization, Eur. J. Biochem, 1995, vol. 232, pp. 19-27.
Gitshier et al., "Remembrances of factor VIII. Part 1: The race to the gene", Journal of Thrombosis and Haemostatsis, 2004, vol. 2, pp. 383-387.
Vehar et al., "Structure of human factor VIII", Nature, 1984, vol. 312, pp. 337-342.
Howard at al., "African-Americans Express Multiple Haplotypic Forms of the Wildtype Factor VIII (FVIII) Protein: A Possible Role for Pharmacogentics in FVIII Inhibitor Development?", Blood, vol. 104, 2004, Abstract 384.
Viel et al., "Inhibitors of Factor VIII in Black Patients with Hemophilia", The New England Journal of Medicine, 2009, vol. 360, pp. 1618-1627.
Toole et al., "Molecular cloning of a cDNA encoding human antihaemophilic factor", Nature, 1984, vol. 312, pp. 342-347.

\* cited by examiner

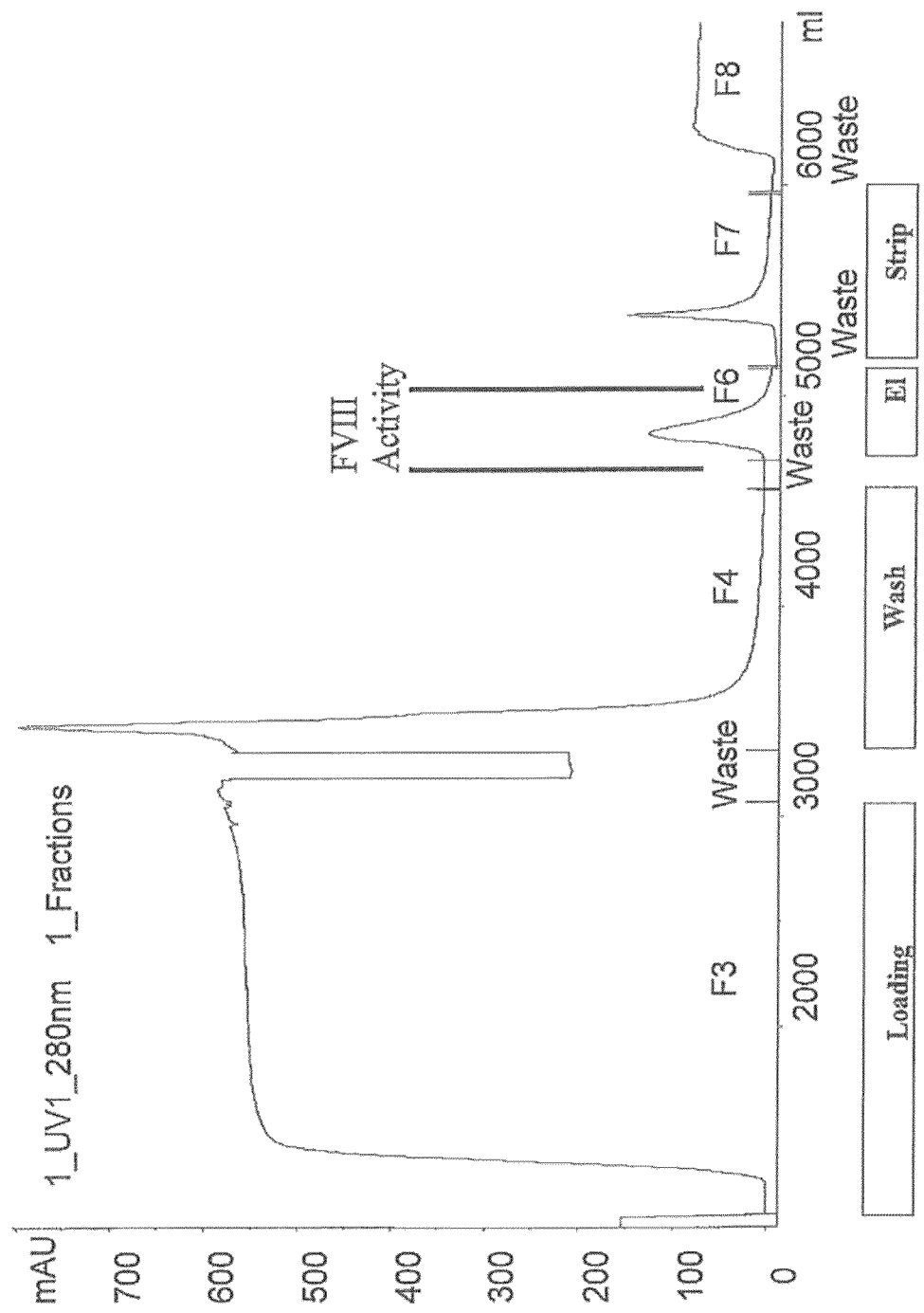

SEQUENCE LISTING

<160> NUMBER OF SEQ ID NOS: 35

<210> SEQ ID NO 1
<211> LENGTH: 4
<212> TYPE: PRT
<213> ORGANISM: Artificial Sequence
<220> FEATURE:
<223> OTHER INFORMATION: The first four amino acids for the B-domain of
      Human Factor VIII Sequence

<400> SEQUENCE: 1

```
Ser Phe Ser Gln
 1

<210> SEQ ID NO 2
<211> LENGTH: 10
<212> TYPE: PRT
<213> ORGANISM: Artificial Sequence
<220> FEATURE:
<223> OTHER INFORMATION: The last ten amino acids for the B-domain of
      Human Factor VIII Sequence

<400> SEQUENCE: 2

Asn Pro Pro Val Leu Lys Arg His Gln Arg
 1               5                  10

<210> SEQ ID NO 3
<211> LENGTH: 1457
<212> TYPE: PRT
<213> ORGANISM: Artificial Sequence
<220> FEATURE:
<223> OTHER INFORMATION: Derived from human factor VIII sequence

<400> SEQUENCE: 3

Met Gln Ile Glu Leu Ser Thr Cys Phe Phe Leu Cys Leu Leu Arg Phe
 1               5                  10                  15

Cys Phe Ser Ala Thr Arg Arg Tyr Tyr Leu Gly Ala Val Glu Leu Ser
             20                  25                  30

Trp Asp Tyr Met Gln Ser Asp Leu Gly Glu Leu Pro Val Asp Ala Arg
         35                  40                  45

Phe Pro Pro Arg Val Pro Lys Ser Phe Pro Phe Asn Thr Ser Val Val
     50                  55                  60

Tyr Lys Lys Thr Leu Phe Val Glu Phe Thr Val His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270
```

```
Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
            405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
```

-continued

```
            690                 695                 700
Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Pro Pro Val Leu
                755                 760                 765

Lys Arg His Gln Arg Glu Ile Thr Arg Thr Thr Leu Gln Ser Asp Gln
            770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
                820                 825                 830

Asp Tyr Gly Met Ser Ser Ser Pro His Val Leu Arg Asn Arg Ala Gln
                835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
                900                 905                 910

Ser Leu Ile Ser Tyr Glu Glu Asp Gln Arg Gln Gly Ala Glu Pro Arg
                915                 920                 925

Lys Asn Phe Val Lys Pro Asn Glu Thr Lys Thr Tyr Phe Trp Lys Val
                930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
                980                 985                 990

Gly Arg Gln Val Thr Val Gln Glu Phe Ala Leu Phe Phe Thr Ile Phe
                995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110
```

Leu Pro Ser Lys Ala Gly Ile Trp Arg Val Glu Cys Leu Ile Gly
1115                1120                1125

Glu His Leu His Ala Gly Met Ser Thr Leu Phe Leu Val Tyr Ser
1130                1135                1140

Asn Lys Cys Gln Thr Pro Leu Gly Met Ala Ser Gly His Ile Arg
1145                1150                1155

Asp Phe Gln Ile Thr Ala Ser Gly Gln Tyr Gly Gln Trp Ala Pro
1160                1165                1170

Lys Leu Ala Arg Leu His Tyr Ser Gly Ser Ile Asn Ala Trp Ser
1175                1180                1185

Thr Lys Glu Pro Phe Ser Trp Ile Lys Val Asp Leu Leu Ala Pro
1190                1195                1200

Met Ile Ile His Gly Ile Lys Thr Gln Gly Ala Arg Gln Lys Phe
1205                1210                1215

Ser Ser Leu Tyr Ile Ser Gln Phe Ile Ile Met Tyr Ser Leu Asp
1220                1225                1230

Gly Lys Lys Trp Gln Thr Tyr Arg Gly Asn Ser Thr Gly Thr Leu
1235                1240                1245

Met Val Phe Phe Gly Asn Val Asp Ser Ser Gly Ile Lys His Asn
1250                1255                1260

Ile Phe Asn Pro Pro Ile Ile Ala Arg Tyr Ile Arg Leu His Pro
1265                1270                1275

Thr His Tyr Ser Ile Arg Ser Thr Leu Arg Met Glu Leu Met Gly
1280                1285                1290

Cys Asp Leu Asn Ser Cys Ser Met Pro Leu Gly Met Glu Ser Lys
1295                1300                1305

Ala Ile Ser Asp Ala Gln Ile Thr Ala Ser Ser Tyr Phe Thr Asn
1310                1315                1320

Met Phe Ala Thr Trp Ser Pro Ser Lys Ala Arg Leu His Leu Gln
1325                1330                1335

Gly Arg Ser Asn Ala Trp Arg Pro Gln Val Asn Asn Pro Lys Glu
1340                1345                1350

Trp Leu Gln Val Asp Phe Gln Lys Thr Met Lys Val Thr Gly Val
1355                1360                1365

Thr Thr Gln Gly Val Lys Ser Leu Leu Thr Ser Met Tyr Val Lys
1370                1375                1380

Glu Phe Leu Ile Ser Ser Ser Gln Asp Gly His Gln Trp Thr Leu
1385                1390                1395

Phe Phe Gln Asn Gly Lys Val Lys Val Phe Gln Gly Asn Gln Asp
1400                1405                1410

Ser Phe Thr Pro Val Val Asn Ser Leu Asp Pro Pro Leu Leu Thr
1415                1420                1425

Arg Tyr Leu Arg Ile His Pro Gln Ser Trp Val His Gln Ile Ala
1430                1435                1440

Leu Arg Met Glu Val Leu Gly Cys Glu Ala Gln Asp Leu Tyr
1445                1450                1455

<210> SEQ ID NO 4
<211> LENGTH: 2332
<212> TYPE: PRT
<213> ORGANISM: Homo Sapiens
<220> FEATURE:
<223> OTHER INFORMATION: Human factor VIII sequence

<400> SEQUENCE: 4

```
Ala Thr Arg Arg Tyr Tyr Leu Gly Ala Val Glu Leu Ser Trp Asp Tyr
  1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Asp His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
             100                 105                 110

Glu Tyr Asp Asp Gln Thr Ser Gln Arg Glu Lys Glu Asp Asp Lys Val
         115                 120                 125

Phe Pro Gly Gly Ser His Thr Tyr Val Trp Gln Val Leu Lys Glu Asn
 130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                 165                 170                 175

Leu Val Cys Arg Glu Gly Ser Leu Ala Lys Glu Lys Thr Gln Thr Leu
             180                 185                 190

His Lys Phe Ile Leu Leu Phe Ala Val Phe Asp Glu Gly Lys Ser Trp
         195                 200                 205

His Ser Glu Thr Lys Asn Ser Leu Met Gln Asp Arg Asp Ala Ala Ser
 210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                 245                 250                 255

Val Ile Gly Met Gly Thr Thr Pro Glu Val His Ser Ile Phe Leu Glu
             260                 265                 270

Gly His Thr Phe Leu Val Arg Asn His Arg Gln Ala Ser Leu Glu Ile
         275                 280                 285

Ser Pro Ile Thr Phe Leu Thr Ala Gln Thr Leu Leu Met Asp Leu Gly
 290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                 325                 330                 335

Met Lys Asn Asn Glu Glu Ala Glu Asp Tyr Asp Asp Asp Leu Thr Asp
             340                 345                 350

Ser Glu Met Asp Val Val Arg Phe Asp Asp Asp Asn Ser Pro Ser Phe
         355                 360                 365

Ile Gln Ile Arg Ser Val Ala Lys Lys His Pro Lys Thr Trp Val His
 370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                 405                 410                 415
```

```
Gln Arg Ile Gly Arg Lys Tyr Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
        530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
        770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
```

```
                835             840             845
Phe Thr Pro Glu Ser Gly Leu Gln Leu Arg Leu Asn Glu Lys Leu Gly
    850             855             860

Thr Thr Ala Ala Thr Glu Leu Lys Lys Leu Asp Phe Lys Val Ser Ser
865             870             875             880

Thr Ser Asn Asn Leu Ile Ser Thr Ile Pro Ser Asp Asn Leu Ala Ala
            885             890             895

Gly Thr Asp Asn Thr Ser Ser Leu Gly Pro Pro Ser Met Pro Val His
            900             905             910

Tyr Asp Ser Gln Leu Asp Thr Thr Leu Phe Gly Lys Lys Ser Ser Pro
            915             920             925

Leu Thr Glu Ser Gly Gly Pro Leu Ser Leu Ser Glu Glu Asn Asn Asp
    930             935             940

Ser Lys Leu Leu Glu Ser Gly Leu Met Asn Ser Gln Glu Ser Ser Trp
945             950             955             960

Gly Lys Asn Val Ser Ser Thr Glu Ser Gly Arg Leu Phe Lys Gly Lys
            965             970             975

Arg Ala His Gly Pro Ala Leu Leu Thr Lys Asp Asn Ala Leu Phe Lys
            980             985             990

Val Ser Ile Ser Leu Leu Lys Thr Asn Lys Thr Ser Asn Asn Ser Ala
            995             1000            1005

Thr Asn Arg Lys Thr His Ile Asp Gly Pro Ser Leu Leu Ile Glu
    1010            1015            1020

Asn Ser Pro Ser Val Trp Gln Asn Ile Leu Glu Ser Asp Thr Glu
    1025            1030            1035

Phe Lys Lys Val Thr Pro Leu Ile His Asp Arg Met Leu Met Asp
    1040            1045            1050

Lys Asn Ala Thr Ala Leu Arg Leu Asn His Met Ser Asn Lys Thr
    1055            1060            1065

Thr Ser Ser Lys Asn Met Glu Met Val Gln Gln Lys Lys Glu Gly
    1070            1075            1080

Pro Ile Pro Pro Asp Ala Gln Asn Pro Asp Met Ser Phe Phe Lys
    1085            1090            1095

Met Leu Phe Leu Pro Glu Ser Ala Arg Trp Ile Gln Arg Thr His
    1100            1105            1110

Gly Lys Asn Ser Leu Asn Ser Gly Gln Gly Pro Ser Pro Lys Gln
    1115            1120            1125

Leu Val Ser Leu Gly Pro Glu Lys Ser Val Glu Gly Gln Asn Phe
    1130            1135            1140

Leu Ser Glu Lys Asn Lys Val Val Val Gly Lys Gly Glu Phe Thr
    1145            1150            1155

Lys Asp Val Gly Leu Lys Glu Met Val Phe Pro Ser Ser Arg Asn
    1160            1165            1170

Leu Phe Leu Thr Asn Leu Asp Asn Leu His Glu Asn Asn Thr His
    1175            1180            1185

Asn Gln Glu Lys Lys Ile Gln Glu Glu Ile Glu Lys Lys Glu Thr
    1190            1195            1200

Leu Ile Gln Glu Asn Val Val Leu Pro Gln Ile His Thr Val Thr
    1205            1210            1215

Gly Thr Lys Asn Phe Met Lys Asn Leu Phe Leu Leu Ser Thr Arg
    1220            1225            1230

Gln Asn Val Glu Gly Ser Tyr Asp Gly Ala Tyr Ala Pro Val Leu
    1235            1240            1245
```

```
Gln Asp Phe Arg Ser Leu Asn Asp Ser Thr Asn Arg Thr Lys Lys
1250                1255                1260

His Thr Ala His Phe Ser Lys Lys Gly Glu Glu Glu Asn Leu Glu
1265                1270                1275

Gly Leu Gly Asn Gln Thr Lys Gln Ile Val Glu Lys Tyr Ala Cys
1280                1285                1290

Thr Thr Arg Ile Ser Pro Asn Thr Ser Gln Gln Asn Phe Val Thr
1295                1300                1305

Gln Arg Ser Lys Arg Ala Leu Lys Gln Phe Arg Leu Pro Leu Glu
1310                1315                1320

Glu Thr Glu Leu Glu Lys Arg Ile Ile Val Asp Asp Thr Ser Thr
1325                1330                1335

Gln Trp Ser Lys Asn Met Lys His Leu Thr Pro Ser Thr Leu Thr
1340                1345                1350

Gln Ile Asp Tyr Asn Glu Lys Glu Lys Gly Ala Ile Thr Gln Ser
1355                1360                1365

Pro Leu Ser Asp Cys Leu Thr Arg Ser His Ser Ile Pro Gln Ala
1370                1375                1380

Asn Arg Ser Pro Leu Pro Ile Ala Lys Val Ser Ser Phe Pro Ser
1385                1390                1395

Ile Arg Pro Ile Tyr Leu Thr Arg Val Leu Phe Gln Asp Asn Ser
1400                1405                1410

Ser His Leu Pro Ala Ala Ser Tyr Arg Lys Lys Asp Ser Gly Val
1415                1420                1425

Gln Glu Ser Ser His Phe Leu Gln Gly Ala Lys Lys Asn Asn Leu
1430                1435                1440

Ser Leu Ala Ile Leu Thr Leu Glu Met Thr Gly Asp Gln Arg Glu
1445                1450                1455

Val Gly Ser Leu Gly Thr Ser Ala Thr Asn Ser Val Thr Tyr Lys
1460                1465                1470

Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635
```

```
Asn Pro Pro Val Leu Lys Arg His Gln Arg Glu Ile Thr Arg Thr
    1640                1645                1650

Thr Leu Gln Ser Asp Gln Glu Ile Asp Tyr Asp Asp Thr Ile
    1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
```

```
                    2030                2035                2040
Gly Gln Trp Ala Pro Lys Leu Ala Arg Leu His Tyr Ser Gly Ser
    2045                2050                2055
Ile Asn Ala Trp Ser Thr Lys Glu Pro Phe Ser Trp Ile Lys Val
    2060                2065                2070
Asp Leu Leu Ala Pro Met Ile Ile His Gly Ile Lys Thr Gln Gly
    2075                2080                2085
Ala Arg Gln Lys Phe Ser Ser Leu Tyr Ile Ser Gln Phe Ile Ile
    2090                2095                2100
Met Tyr Ser Leu Asp Gly Lys Lys Trp Gln Thr Tyr Arg Gly Asn
    2105                2110                2115
Ser Thr Gly Thr Leu Met Val Phe Phe Gly Asn Val Asp Ser Ser
    2120                2125                2130
Gly Ile Lys His Asn Ile Phe Asn Pro Pro Ile Ile Ala Arg Tyr
    2135                2140                2145
Ile Arg Leu His Pro Thr His Tyr Ser Ile Arg Ser Thr Leu Arg
    2150                2155                2160
Met Glu Leu Met Gly Cys Asp Leu Asn Ser Cys Ser Met Pro Leu
    2165                2170                2175
Gly Met Glu Ser Lys Ala Ile Ser Asp Ala Gln Ile Thr Ala Ser
    2180                2185                2190
Ser Tyr Phe Thr Asn Met Phe Ala Thr Trp Ser Pro Ser Lys Ala
    2195                2200                2205
Arg Leu His Leu Gln Gly Arg Ser Asn Ala Trp Arg Pro Gln Val
    2210                2215                2220
Asn Asn Pro Lys Glu Trp Leu Gln Val Asp Phe Gln Lys Thr Met
    2225                2230                2235
Lys Val Thr Gly Val Thr Thr Gln Gly Val Lys Ser Leu Leu Thr
    2240                2245                2250
Ser Met Tyr Val Lys Glu Phe Leu Ile Ser Ser Ser Gln Asp Gly
    2255                2260                2265
His Gln Trp Thr Leu Phe Phe Gln Asn Gly Lys Val Lys Val Phe
    2270                2275                2280
Gln Gly Asn Gln Asp Ser Phe Thr Pro Val Val Asn Ser Leu Asp
    2285                2290                2295
Pro Pro Leu Leu Thr Arg Tyr Leu Arg Ile His Pro Gln Ser Trp
    2300                2305                2310
Val His Gln Ile Ala Leu Arg Met Glu Val Leu Gly Cys Glu Ala
    2315                2320                2325
Gln Asp Leu Tyr
    2330

<210> SEQ ID NO 5
<211> LENGTH: 33
<212> TYPE: DNA
<213> ORGANISM: Artificial Sequence
<220> FEATURE:
<223> OTHER INFORMATION: Primer PEG1 used for Mutagenesis

<400> SEQUENCE: 5
gatgtccgtc ctttgtgctc aaggagatta cca                           33

<210> SEQ ID NO 6
<211> LENGTH: 34
<212> TYPE: DNA
<213> ORGANISM: Artificial Sequence
```

```
<220> FEATURE:
<223> OTHER INFORMATION: Primer PEG2 used for Mutagenesis

<400> SEQUENCE: 6
ttgtattcaa ggagatgccc aaaaggtgta aaac                              34

<210> SEQ ID NO 7
<211> LENGTH: 34
<212> TYPE: DNA
<213> ORGANISM: Artificial Sequence
<220> FEATURE:
<223> OTHER INFORMATION: Primer PEG3 used for Mutagenesis

<400> SEQUENCE: 7
ttaccaaaag gtgtatgcca tttgaaggat tttc                              34

<210> SEQ ID NO 8
<211> LENGTH: 33
<212> TYPE: DNA
<213> ORGANISM: Artificial Sequence
<220> FEATURE:
<223> OTHER INFORMATION: Primer PEG4 used for Mutagenesis

<400> SEQUENCE: 8
aaggattttc caatttgccc aggagaaata ttc                               33

<210> SEQ ID NO 9
<211> LENGTH: 34
<212> TYPE: DNA
<213> ORGANISM: Artificial Sequence
<220> FEATURE:
<223> OTHER INFORMATION: Primer PEG 5 used for Mutagenesis

<400> SEQUENCE: 9
gattatattt aagaattgcg caagcagacc atat                              34

<210> SEQ ID NO 10
<211> LENGTH: 36
<212> TYPE: DNA
<213> ORGANISM: Artificial Sequence
<220> FEATURE:
<223> OTHER INFORMATION: Primer PEG6 used for Mutagenesis

<400> SEQUENCE: 10
tagaaaaaac tttgtctgcc ctaatgaaac caaaac                            36

<210> SEQ ID NO 11
<211> LENGTH: 33
<212> TYPE: DNA
<213> ORGANISM: Artificial Sequence
<220> FEATURE:
<223> OTHER INFORMATION: Primer PEG7 used for Mutagenesis

<400> SEQUENCE: 11
aactttgtca agccttgcga aaccaaaact tac                               33

<210> SEQ ID NO 12
<211> LENGTH: 34
<212> TYPE: DNA
<213> ORGANISM: Artificial Sequence
<220> FEATURE:
<223> OTHER INFORMATION: Primer PEG8 used for Mutagenesis

<400> SEQUENCE: 12
gtcaagccta atgaatgcaa aacttacttt tgga                              34
```

```
<210> SEQ ID NO 13
<211> LENGTH: 35
<212> TYPE: DNA
<213> ORGANISM: Artificial Sequence
<220> FEATURE:
<223> OTHER INFORMATION: PEG9 Primer used for Mutagenesis

<400> SEQUENCE: 13
caagcctaat gaaacctgca cttacttttg gaaag                              35

<210> SEQ ID NO 14
<211> LENGTH: 36
<212> TYPE: DNA
<213> ORGANISM: Artificial Sequence
<220> FEATURE:
<223> OTHER INFORMATION: Primer PEG10 used for Mutagenesis

<400> SEQUENCE: 14
ctaatgaaac caaaacttgc ttttggaaag tgcaac                             36

<210> SEQ ID NO 15
<211> LENGTH: 33
<212> TYPE: DNA
<213> ORGANISM: Artificial Sequence
<220> FEATURE:
<223> OTHER INFORMATION: Primer PEG11 used for Mutagenesis

<400> SEQUENCE: 15
atttcttatg aggaatgcca gaggcaagga gca                                33

<210> SEQ ID NO 16
<211> LENGTH: 33
<212> TYPE: DNA
<213> ORGANISM: Artificial Sequence
<220> FEATURE:
<223> OTHER INFORMATION: Primer PEG12 used for Mutagenesis

<400> SEQUENCE: 16
tcttatgagg aagattgcag gcaaggagca gaa                                33

<210> SEQ ID NO 17
<211> LENGTH: 36
<212> TYPE: DNA
<213> ORGANISM: Artificial Sequence
<220> FEATURE:
<223> OTHER INFORMATION: Primer PEG13 used for Mutagenesis

<400> SEQUENCE: 17
caaggagcag aaccttgcaa aaactttgtc aagcct                             36

<210> SEQ ID NO 18
<211> LENGTH: 33
<212> TYPE: DNA
<213> ORGANISM: Artificial Sequence
<220> FEATURE:
<223> OTHER INFORMATION: Primer PEG14 used for Mutagenesis

<400> SEQUENCE: 18
ggagcagaac ctagatgcaa ctttgtcaag cct                                33

<210> SEQ ID NO 19
<211> LENGTH: 33
<212> TYPE: DNA
<213> ORGANISM: Artificial Sequence
<220> FEATURE:
<223> OTHER INFORMATION: Primer PEG15 used for Mutagenesis
```

```
<400> SEQUENCE: 19
cgctcagttg ccaagtgtca tcctaaaact tgg                                    33

<210> SEQ ID NO 20
<211> LENGTH: 33
<212> TYPE: DNA
<213> ORGANISM: Artificial Sequence
<220> FEATURE:
<223> OTHER INFORMATION: Primer PEG16 used for Mutagenesis

<400> SEQUENCE: 20
tcagttgcca agaagtgtcc taaaacttgg gta                                    33

<210> SEQ ID NO 21
<211> LENGTH: 33
<212> TYPE: DNA
<213> ORGANISM: Artificial Sequence
<220> FEATURE:
<223> OTHER INFORMATION: Primer PEG17 used for Mutagenesis

<400> SEQUENCE: 21
ctcctcatct gctactgcga atctgtagat caa                                    33

<210> SEQ ID NO 22
<211> LENGTH: 35
<212> TYPE: DNA
<213> ORGANISM: Artificial Sequence
<220> FEATURE:
<223> OTHER INFORMATION: Primer PEG18 used for Mutagenesis

<400> SEQUENCE: 22
caaaatcttt tccattctgc acctcagtcg tgtac                                  35

<210> SEQ ID NO 23
<211> LENGTH: 33
<212> TYPE: DNA
<213> ORGANISM: Artificial Sequence
<220> FEATURE:
<223> OTHER INFORMATION: Primer PEG19 used for Mutagenesis

<400> SEQUENCE: 23
gtcaatggtt atgtatgcag gtctctgcca ggt                                    33

<210> SEQ ID NO 24
<211> LENGTH: 33
<212> TYPE: DNA
<213> ORGANISM: Artificial Sequence
<220> FEATURE:
<223> OTHER INFORMATION: Primer PEG20 used for Mutagenesis

<400> SEQUENCE: 24
cagacttatc gaggatgttc cactggaacc tta                                    33

<210> SEQ ID NO 25
<211> LENGTH: 33
<212> TYPE: DNA
<213> ORGANISM: Artificial Sequence
<220> FEATURE:
<223> OTHER INFORMATION: Primer PEG21 used for Mutagenesis

<400> SEQUENCE: 25
atccaggctg aggtttgtga tacagtggtc att                                    33

<210> SEQ ID NO 26
```

<211> LENGTH: 33
<212> TYPE: DNA
<213> ORGANISM: Artificial Sequence
<220> FEATURE:
<223> OTHER INFORMATION: Primer PEG22 used for Mutagenesis

<400> SEQUENCE: 26
gaagatgata aagtctgtcc tggtggaagc cat        33

<210> SEQ ID NO 27
<211> LENGTH: 33
<212> TYPE: DNA
<213> ORGANISM: Artificial Sequence
<220> FEATURE:
<223> OTHER INFORMATION: Primer PEG23 used for Mutagenesis

<400> SEQUENCE: 27
cagcggattg gtaggtgtta caaaaaagtc cga        33

<210> SEQ ID NO 28
<211> LENGTH: 33
<212> TYPE: DNA
<213> ORGANISM: Artificial Sequence
<220> FEATURE:
<223> OTHER INFORMATION: Primer PEG24 used for Mutagenesis

<400> SEQUENCE: 28
gaagatgggc caacttgctc agatcctcgg tgc        33

<210> SEQ ID NO 29
<211> LENGTH: 33
<212> TYPE: DNA
<213> ORGANISM: Artificial Sequence
<220> FEATURE:
<223> OTHER INFORMATION: Primer PEG25 used for Mutagenesis

<400> SEQUENCE: 29
cagataatgt cagactgcag gaatgtcatc ctg        33

<210> SEQ ID NO 30
<211> LENGTH: 33
<212> TYPE: DNA
<213> ORGANISM: Artificial Sequence
<220> FEATURE:
<223> OTHER INFORMATION: Primer PEG26 used for Mutagenesis

<400> SEQUENCE: 30
cacactaaca cactgtgtcc tgctcatggg aga        33

<210> SEQ ID NO 31
<211> LENGTH: 33
<212> TYPE: DNA
<213> ORGANISM: Artificial Sequence
<220> FEATURE:
<223> OTHER INFORMATION: Primer PEG27 used for Mutagenesis

<400> SEQUENCE: 31
cagatggaag atccctgctt taaagagaat tat        33

<210> SEQ ID NO 32
<211> LENGTH: 33
<212> TYPE: DNA
<213> ORGANISM: Artificial Sequence
<220> FEATURE:
<223> OTHER INFORMATION: Primer PEG28 used for Mutagenesis

<400> SEQUENCE: 32

```
acccagggtg cccgttgcaa gttctccagc ctc                                    33

<210> SEQ ID NO 33
<211> LENGTH: 33
<212> TYPE: DNA
<213> ORGANISM: Artificial Sequence
<220> FEATURE:
<223> OTHER INFORMATION: Primer PEG29 used for Mutagenesis

<400> SEQUENCE: 33
aaagtaaagg tttttgcgg aaatcaagac tcc                                     33

<210> SEQ ID NO 34
<211> LENGTH: 33
<212> TYPE: DNA
<213> ORGANISM: Artificial Sequence
<220> FEATURE:
<223> OTHER INFORMATION: Primer PEG30 used for Mutagenesis

<400> SEQUENCE: 34
ttgcagttgt cagttgcttt gcatgaggtg gca                                    33

<210> SEQ ID NO 35
<211> LENGTH: 33
<212> TYPE: DNA
<213> ORGANISM: Artificial Sequence
<220> FEATURE:
<223> OTHER INFORMATION: Primer PEG31 used for Mutagenesis

<400> SEQUENCE: 35
aatatggaaa gaaacgctag ggctccctgc aat                                    33
```

FACTOR VIII CONJUGATES

CROSS REFERENCE TO RELATED APPLICATIONS

This application is a continuation of U.S. patent application Ser. No. 12/540,703 filed on Aug. 13, 2009, which is a continuation of U.S. patent application Ser. No. 11/273,896 filed on Nov. 14, 2005 (now U.S. Pat. No. 7,632,921), which claims benefit of priority to U.S. Patent App. Ser. No. 60/627,277 filed on Nov. 12, 2004, all of which applications are hereby incorporated herein by reference in their entireties.

FIELD OF THE INVENTION

This invention relates to Factor VIII (FVIII) muteins that allow coupling, at a defined site, to one or more biocompatible polymers such as polyethylene glycol. In addition, related formulations, dosages and methods of administration thereof for therapeutic purposes are provided. These modified FVIII variants, and associated compositions and methods are useful in providing a treatment option with reduced injection frequency and reduced immunogenic response for individuals afflicted with hemophilia A.

BACKGROUND OF THE INVENTION

Hemophilia A is the most common hereditary coagulation disorder, with an estimated incidence of 1 per 5000 males. It is caused by deficiency or structural defects in FVIII, a critical component of the intrinsic pathway of blood coagulation. The current treatment for hemophilia A involves intravenous injection of human FVIII. Human FVIII has been produced recombinantly as a single-chain molecule of approximately 300 kD. It consists of the structural domains A1-A2-B-A3-C1-C2 (Thompson, 2003, Semin. Hematol. 29, pp. 11-22). The precursor product is processed into two polypeptide chains of 200 kD (heavy) and 80 kD (light) in the Golgi Apparatus, with the two chains held together by metal ions (Kaufman et al., 1988, J. Biol. Chem. 263, p. 6352; Andersson et al., 1986, Proc. Natl. Acad. Sci. 83, p. 2979).

The B-domain of FVIII seems to be dispensable as B-domain deleted FVIII (BDD, 90 kD A1-A2 heavy chain plus 80 kD light chain) has also been shown to be effective as a replacement therapy for hemophilia A. The B-domain deleted FVIII sequence contains a deletion of all but 14 amino acids of the B-domain.

Hemophilia A patients are currently treated by intravenous administration of FVIII on demand or as a prophylactic therapy administered several times a week. For prophylactic treatment 15-25 IU/kg bodyweight is given of factor VIII three times a week. It is constantly required in the patient. Because of its short half-life in man, FVIII must be administered frequently. Despite its large size of greater than 300 kD for the full-length protein, FVIII has a half-life in humans of only about 11 hours. (Ewenstein et al, 2004, Semin. Hematol. 41, pp. 1-16). The need for frequent intravenous injection creates tremendous barriers to patient compliance. It would be more convenient for the patients if a FVIII product could be developed that had a longer half-life and therefore required less frequent administration. Furthermore, the cost of treatment could be reduced if the half-life were increased because fewer dosages may then be required.

An additional disadvantage to the current therapy is that about 25-30% of patients develop antibodies that inhibit FVIII activity (Saenko et al, 2002, Haemophilia 8, pp. 1-11). The major epitopes of inhibitory antibodies are located within the A2 domain at residues 484-508, the A3 domain at residues 1811-1818, and the C2 domain. Antibody development prevents the use of FVIII as a replacement therapy, forcing this group of patients to seek an even more expensive treatment with high-dose recombinant Factor VIIa and immune tolerance therapy.

The following studies identified FVIII epitopes of inhibitory antibodies. In a study of 25 inhibitory plasma samples, 11 were found to bind to the thrombin generated 73 kD light chain fragment A3C1C2, 4 to the A2 domain, and 10 to both (Fulcher, C. et al., 1985, Proc. Natl. Acad. Sci. 2(22), pp. 7728-32). In another study, six of eight A2 domain inhibitors from patients were neutralized by a recombinant A2 polypeptide (Scandella, D. et al., 1993, Blood 82(6), pp. 1767-75). Epitopes for six of nine inhibitors from patients were mapped to A2 residues 379-538 (Scandella, D. et al., 1988, Proc. Natl. Acad. Sci. 85(16), pp. 6152-6). An epitope for 18 heavy-chain inhibitors was localized to the same N-terminal 18.3 kD region of the A2 domain (Scandella, D. et al., 1989, Blood 74(5), pp. 1618-26).

An active, recombinant hybrid human/porcine FVIII molecule, generated by replacing human A2 domain residues 387-604 with the homologous porcine sequence, was resistant to a patient A2 inhibitor (Lubin, I. et al., 1994, J. Biol. Chem. 269(12), pp. 8639-41) and resistant to a murine monoclonal antibody mAB 413 IgG that competes with patient A2 inhibitors for binding to A2 (Scandella, D. et al., 1992, Thromb Haemost. 67(6), pp. 665-71). This A2 domain epitope was further localized to the A2 domain residues 484-508 when experiments showed that mAB 413 IgG and four patient inhibitors did not inhibit a hybrid human/porcine FVIII in which the A2 domain residues 484-508 were replaced with that of porcine (Healey, J. et al., 1995, J. Biol. Chem. 270(24), pp. 14505-9). This hybrid FVIII was also more resistant to at least half of 23 patient plasmas screened (Barrow, R. et al., 2000, Blood 95(2), pp. 564-8). Alanine scanning mutagenesis identified residue 487 to be critical for binding to all five patient inhibitors tested, while residues 484, 487, 489, and 492 were all important to interaction with mAB 413 IgG (Lubin, I., J. Biol. Chem. 272(48), pp. 30191-5). Inhibitory antibody titers in mice receiving the R484A/R489A/P492A mutant, but not the R484A/R489A mutant, were significantly lower than in mice receiving control human BDD FVIII (Parker, E. et al., 2004, Blood 104(3), pp. 704-10). In sum, the 484-508 region of the A2 domain seems to be a binding site for inhibitors of FVIII activity.

In addition to the development of an immune response to FVIII, another problem with conventional therapy is that it requires frequent dosaging because of the short half-life of FVIII in vivo. The mechanisms for clearance of FVIII from the circulation have been studied.

FVIII clearance from circulation has been partly attributed to specific binding to the low-density lipoprotein receptor-related protein (LRP), a hepatic clearance receptor with broad ligand specificity (Oldenburg et al., 2004, Haemophilia 10 Suppl 4, pp. 133-139). Recently, the low-density lipoprotein (LDL) receptor was also shown to play a role in FVIII clearance, such as by cooperating with LRP in regulating plasma levels of FVIII (Bovenschen et al., 2005, Blood 106, pp. 906-910). Both interactions are facilitated by binding to cell-surface heparin sulphate proteoglycans (HSPGs). Plasma half-life in mice can be prolonged by 3.3-fold when LRP is blocked or 5.5-fold when both LRP and cell-surface HSPGs are blocked (Sarafanov et al., 2001, J. Biol. Chem. 276, pp. 11970-11979). HSPGs are hypothesized to concentrate FVIII on the cell surface and to present it to LRP. LRP binding sites on FVIII have been localized to A2 residues 484-509 (Saenko et al., 1999, J. Biol. Chem. 274, pp. 37685-37692), A3 residues 1811-1818 (Bovenschen et al., 2003, J. Biol. Chem. 278, pp. 9370-9377) and an epitope in the C2 domain (Lenting et al., 1999, J. Biol. Chem. 274, pp. 23734-23739).

FVIII is also cleared from circulation by the action of proteases. To understand this effect, one must understand the mechanism by which FVIII is involved in blood coagulation. FVIII circulates as a heterodimer of heavy and light chains, bound to vWF. VWF binding involves FVIII residues 1649-1689 (Foster et al., 1988, J. Biol. Chem. 263, pp. 5230-5234), and parts of C1 (Jacquemin et al., 2000, Blood 96, pp. 958-965) and C2 domains (Spiegel, P. et al., 2004, J. Biol. Chem. 279(51), pp. 53691-8). FVIII is activated by thrombin, which cleaves peptide bonds after residues 372, 740, and 1689 to generate a heterotrimer of A1, A2, and A3-C1-C2 domains (Pittman et al., 1988, Proc. Natl. Acad. Sci. 85, pp. 2429-2433). Upon activation, FVIII dissociates from vWF and is concentrated to the cell surface of platelets by binding to phospholipid. Phospholipid binding involves FVIII residues 2199, 2200, 2251, and 2252 (Gilbert et al., 2002, J. Biol. Chem. 277, pp. 6374-6381). There it binds to FIX through interactions with FVIII residues 558-565 (Fay et al., 1994, J. Biol. Chem. 269, pp. 20522-20527) and 1811-1818 (Lenting et al., 1996, J. Biol. Chem. 271, pp. 1935-1940) and FX through interactions with FVIII residues 349-372 (Nogami et al., 2004, J. Biol. Chem. 279, pp. 15763-15771) and acts as a cofactor for FIX activation of FX, an essential component of the intrinsic coagulation pathway. Activated FVIII (FVIIIa) is partly inactivated by the protease activated protein C (APC) through cleavage after FVIII residues 336 and 562 (Regan et al., 1996, J. Biol. Chem. 271, pp. 3982-3987). The predominant determinant of inactivation, however, is the dissociation of the A2 domain from A1 and A3-C1-C2 (Fay et al., 1991, J. Biol. Chem. 266, pp. 8957-8962).

One method that has been demonstrated to increase the in vivo half-life of a protein is PEGylation. PEGylation is the covalent attachment of long-chained polyethylene glycol (PEG) molecules to a protein or other molecule. The PEG can be in a linear form or in branched form to produce different molecules with different features. Besides increasing the half-life of peptides or proteins, PEGylation has been used to reduce antibody development, protect the protein from protease digestion and keep the material out of the kidney filtrate (Harris et al., 2001, Clinical Pharmacokinetics 40, pp. 539-51). In addition, PEGylation may also increase the overall stability and solubility of the protein. Finally, the sustained plasma concentration of PEGylated proteins can reduce the extent of adverse side effects by reducing the trough to peak levels of a drug, thus eliminating the need to introduce superphysiological levels of protein at early time-points.

Random modification of FVIII by targeting primary amines (N-terminus and lysines) with large polymers such as PEG and dextran has been attempted with varying degree of success (WO94/15625, U.S. Pat. No. 4,970,300, U.S. Pat. No. 6,048,720). The most dramatic improvement, published in a 1994 patent application (WO94/15625), shows a 4-fold half-life improvement but at a cost of 2-fold activity loss after reacting full-length FVIII with 50-fold molar excess of PEG. WO2004/075923 discloses conjugates of FVIII and polyethylene glycol that are created through random modification. Randomly PEGylated proteins, such as interferon-alpha (Kozlowski et al, 2001, BioDrugs 15, pp. 419-429) have been approved as therapeutics in the past.

This random approach, however, is much more problematic for the heterodimeric FVIII. FVIII has hundreds of potential PEGylation sites, including the 158 lysines, the two N-termini, and multiple histidines, serines, threonines, and tyrosines, all of which could potentially be PEGylated with reagents primarily targeting primary amines. For example, the major positional isomer for PEGylated interferon Alpha-2b was shown to be a histidine (Wang et al., 2000, Biochemistry 39, pp. 10634-10640). Furthermore, heterogeneous processing of full length FVIII can lead to a mixture of starting material that leads to further complexity in the PEGylated products. An additional drawback to not controlling the site of PEGylation on FVIII is a potential activity reduction if the PEG were to be attached at or near critical active sites, especially if more than one PEG or a single large PEG is conjugated to FVIII. Because random PEGylation will invariably produce large amounts of multiply PEGylated products, purification to obtain only mono-PEGylated products will drastically lower overall yield. Finally, the enormous heterogeneity in product profile will make consistent synthesis and characterization of each lot nearly impossible. Since good manufacturing requires a consistent, well-characterized product, product heterogeneity is a barrier to commercialization. For all these reasons, a more specific method for PEGylating FVIII is desired.

Various site-directed protein PEGylation strategies have been summarized in a recent review (Kochendoerfer, G., Curr. Opin. Chem. Biol. 2005, available online as of Oct. 15, 2005, direct object identifier doi:10.1016/j.cbpa.2005.10.007). One approach involves incorporation of an unnatural amino acid into proteins by chemical synthesis or recombinant expression followed by the addition of a PEG derivative that will react specifically with the unnatural amino acid. For example, the unnatural amino acid may be one that contains a keto group not found in native proteins. However, chemical synthesis of proteins is not feasible for a protein as large as FVIII. Current limit of peptide synthesis is about 50 residues. Several peptides can be ligated to form a larger piece of polypeptide, but to produce even the B-domain deleted FVIII would require greater than 20 ligations, which would result in less than 1% recovery even under ideal reaction condition. Recombinant expression of proteins with unnatural amino acids has so far mainly been limited to non-mammalian expression systems. This approach is expected to be problematic for a large and complex protein such as FVIII that needs to be expressed in mammalian systems.

Another approach to site-specific PEGylation of proteins is by targeting N-terminal backbone amine with PEG-aldehydes. The low pH required under this process to achieve specificity over other amine groups, however, is not compatible with the narrow near-neutral pH range needed for the stability of FVIII (Wang et al., 2003, International J. Pharmaceutics 259, pp. 1-15). Moreover, N-terminal PEGylation of FVIII may not lead to improved plasma half-life if this region is not involved in plasma clearance. In fact, the N-terminal region of the FVIII light chain has been implicated in binding to the von Willebrand factor (vWF), a carrier protein that is critical for FVIII survival in circulation. By N-terminal modification of factor VIII, the critically important association with vWF may be disrupted or weakened. Thus, N-terminal PEGylation of FVIII may have the opposite effect of reducing plasma half-life of FVIII.

WO90/12874 discloses site-specific modification of human IL-3, granulocyte colony stimulating factor and erythropoietin polypeptides by inserting or substituting a cysteine for another amino acid, then adding a ligand that has a sulfhydryl reactive group. The ligand couples selectively to cysteine residues. Modification of FVIII or any variant thereof is not disclosed.

For the reasons stated above, there exists a need for an improved FVIII variant that possesses greater duration of action in vivo and reduced immunogenicity, while retaining functional activity. Furthermore, it is desirable that such a protein be produced as a homogeneous product in a consistent manner.

SUMMARY OF THE INVENTION

It is an object of the present invention to provide a biocompatible polymer-conjugated functional FVIII polypeptide having improved pharmacokinetic characteristics and therapeutic characteristics.

It is another object of the present invention to provide a biocompatible polymer-conjugated B domain deleted FVIII protein having improved pharmacokinetic properties.

It is yet another object of the invention to provide a biocompatible polymer-conjugated functional FVIII polypeptide having reduced binding to the low-density lipoprotein receptor-related protein (LRP), low-density lipoprotein (LDL) receptor, the heparan sulphate proteoglycans (HSPGs) and/or inhibitory antibodies against FVIII.

It is yet another object of the present invention to provide an improved FVIII variant that possesses greater duration of action in vivo and reduced immunogenicity, which is capable of being produced as a homogeneous product in a consistent manner.

In one aspect of the invention there is provided a conjugate having factor VIII procoagulant activity comprising a functional factor VIII polypeptide covalently attached at one or more predefined sites on the polypeptide to one or more biocompatible polymers, wherein the predefined site is a not an N-terminal amine. The invention also includes a method for the preparation of this conjugate comprising mutating a nucleotide sequence that encodes for the functional factor VIII polypeptide to substitute a coding sequence for a cysteine residue at a pre-defined site; expressing the mutated nucleotide sequence to produce a cysteine enhanced mutein; purifying the mutein; reacting the mutein with the biocompatible polymer that has been activated to react with polypeptides substantially only at the introduced cysteine residues such that the conjugate is formed; and purifying the conjugate. The invention is also directed to pharmaceutical compositions comprising the conjugate and a pharmaceutically acceptable adjuvant and methods of treating hemophilia by administering therapeutically effective amounts of these pharmaceutical compositions to a mammal in need thereof.

The invention also relates to a method for site-directed PEGylation of a factor VIII mutein comprising (a) expressing a site-directed factor VIII mutein wherein the mutein has a cysteine replacement for an amino acid residue on the exposed surface of the factor VIII mutein and that cysteine is capped; (b) contacting the cysteine mutein with a reductant under conditions to mildly reduce the cysteine mutein and to release the cap; (c) removing the cap and the reductant from the cysteine mutein; and (d) at least about 5 minutes after the removal of the reductant, treating the cysteine mutein with PEG comprising a sulfhydryl coupling moiety under conditions such that PEGylated factor VIII mutein is produced.

BRIEF DESCRIPTION OF THE FIGURES

FIG. 1A shows the Mutagenesis Vector and Shuttle Vector.
FIG. 1B shows the Expression Vector.
FIG. 2. A UV absorbance profile at 280 nm with respect to time for the PEG2 protein purified over a monoclonal FVIII antibody chromatography column. The chromatography was performed using an AKTA® Explorer 100 chromatography system from Amersham Bioscience.

FIGS. 6A and 6B were stained with heavy (H) chain antibody while FIGS. 6C and 6D were stained with light (L) chain antibody. "U" is unprocessed material containing both H & L.

FIGS. 28A and 28B include data collected at patient plasma dilution of 5- to 405-fold. FIG. 28C focuses on 1:15-fold dilution for patient HRF-828 plasma. FIG. 28D confirms that the 0.064 IU/mL used for each FVIII sample in the top two panels was not a saturating dose.

FIG. 32A shows PEG2+14; FIG. 32B shows reduction with 200 uM TCEP; FIG. 32C shows reduction with 67 uM TCEP; FIG. 32D shows reduction with 400 uM TCEP; FIG. 32E shows reduction with 100 uM TCEP; and FIG. 32F shows reduction with 670 uM TCEP.

DETAILED DESCRIPTION OF THE INVENTION

Figure 1A:
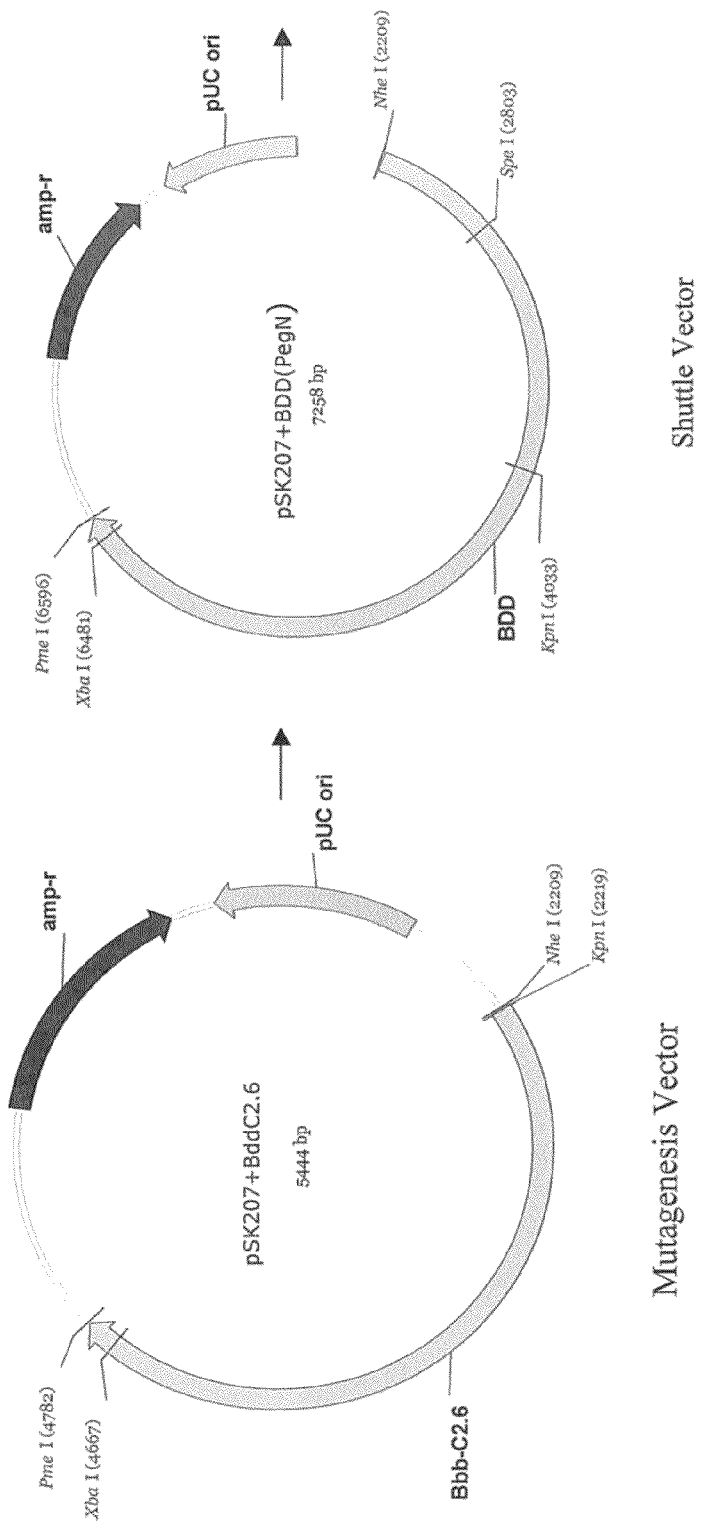
FIG. 1A-1B. Vector maps and mutagenesis strategy for PEG muteins.

The present invention is based on the discovery that polypeptides having FVIII activity can be covalently attached at a predefined site to a biocompatible polymer that is not at an N-terminal amine, and that such polypeptides substantially retain their coagulant activity. Furthermore, these polypeptide conjugates have improved circulation time and reduced antigenicity. The conjugates of the invention are advantageous over the prior art conjugates that had random polymer attachments to FVIII or attachments at an N-terminal. Site-directed attachment allows one to design modifications that avoid the regions required for biological activity and thereby to maintain substantial FVIII activity. It also allows for designing to attach polymers to block binding at sites involved in FVIII clearance. Site-directed attachment also allows for a uniform product rather than the heterogeneous conjugates produced in the art by random polymer coupling. By avoiding attachment at an N-terminal amine of the light chain, the conjugates of the present invention avoid the possible loss of activity from attaching a ligand at an active site of the FVIII polypeptide. The N-terminal region of the light chain is believed to be involved in the association of vWF factor to FVIII, which is a stabilizing association in the circulation.

DEFINITIONS

Biocompatible polymer. A biocompatible polymer includes polyalkylene oxides such as without limitation polyethylene glycol (PEG), dextrans, colominic acids or other carbohydrate based polymers, polymers of amino acids, biotin derivatives, polyvinyl alcohol (PVA), polycarboxylates, polyvinylpyrrolidone, polyethylene-co-maleic acid anhydride, polystyrene-co-malic acid anhydride, polyoxazoline, polyacryloylmorpholine, heparin, albumin, celluloses, hydrolysates of chitosan, starches such as hydroxyethyl-starches and hydroxy propyl-starches, glycogen, agaroses and derivatives thereof, guar gum, pullulan, inulin, xanthan gum, carrageenan, pectin, alginic acid hydrolysates, other bio-polymers and any equivalents thereof. Preferred is polyethylene glycol, and still more preferred is methoxypolyethylene glycol (mPEG). Other useful polyalkylene glycol compounds are polypropylene glycols (PPG), polybutylene glycols (PBG), PEG-glycidyl ethers (Epox-PEG), PEG-oxycarbonylimidazole (CDI-PEG), branched polyethylene glycols, linear polyethylene glycols, forked polyethylene glycols and multi-armed or "super branched" polyethylene glycols (star-PEG).

Polyethylene glycol (PEG). "PEG" and "polyethylene glycol" as used herein are interchangeable and include any water-soluble poly(ethylene oxide). Typically, PEGs for use in accordance with the invention comprise the following structure "—$(OCH_2CH_2)_n$—" where (n) is 2 to 4000. As used herein, PEG also includes "—$CH_2CF_{12}$—$O(CH_2CH_2O)_n$—$CH_2CH_2$—" and "—$(OCH_2CH_2)_nO$—," depending upon whether or not the terminal oxygens have been displaced. Throughout the specification and claims, it should be remembered that the term "PEG" includes structures having various terminal or "end capping" groups, such as without limitation a hydroxyl or a $C_{1-20}$ alkoxy group. The term "PEG" also means a polymer that contains a majority, that is to say, greater than 50%, of —$OCH_2CH_2$— repeating subunits. With respect to specific forms, the PEG can take any number of a variety of molecular weights, as well as structures or geometries such as branched, linear, forked, and multifunctional.

PEGylation. PEGylation is a process whereby a polyethylene glycol (PEG) is covalently attached to a molecule such as a protein.

Activated or Active functional group. When a functional group such as a biocompatible polymer is described as activated, the functional group reacts readily with an electrophile or a nucleophile on another molecule.

B domain deleted FVIII (BDD). As used herein, BDD is characterized by having the amino acid sequence which contains a deletion of all but 14 amino acids of the B-domain of FVIII. The first 4 amino acids of the B-domain (SFSQ, SEQ ID NO:1) are linked to the 10 last residues of the B-domain (NPPVLKRHQR, SEQ ID NO:2). (Lind, P. et al, 1995, Eur. J. Biochem. 232, pp. 19-27). The BDD used herein has the amino acid sequence of SEQ ID NO:3.

FVIII.

Blood clotting Factor VIII (FVIII) is a glycoprotein synthesized and released into the bloodstream by the liver. In the circulating blood, it is bound to von Willebrand factor (vWF, also known as Factor VIII-related antigen) to form a stable complex. Upon activation by thrombin, it dissociates from the complex to interact with other clotting factors in the coagulation cascade, which eventually leads to the formation of a thrombus. Human full-length FVIII has the amino acid sequence of SEQ ID NO:4, although allelic variants are possible.

Functional factor VIII polypeptide. As used herein, functional factor VIII polypeptide denotes a functional polypeptide or combination of polypeptides that are capable, in vivo or in vitro, of correcting human factor VIII deficiencies, characterized, for example, by hemophilia A. Factor VIII has multiple degradation or processed forms in the natural state. These are proteolytically derived from a precursor, one chain protein, as demonstrated herein. A functional factor VIII polypeptide includes such single chain protein and also provides for these various degradation products that have the biological activity of correcting human factor VIII deficiencies. Allelic variations likely exist. The functional factor VIII polypeptides include all such allelic variations, glycosylated versions, modifications and fragments resulting in derivatives of factor VIII so long as they contain the functional segment of human factor VIII and the essential, characteristic human factor VIII functional activity remains unaffected in kind. Those derivatives of factor VIII possessing the requisite functional activity can readily be identified by straightforward in vitro tests described herein. Furthermore, functional factor VIII polypeptide is capable of catalyzing the conversion of factor X to Xa in the presence of factor IXa, calcium, and phospholipid, as well as correcting the coagulation defect in plasma derived from hemophilia A affected individuals. From the disclosure of the sequence of the human factor VIII amino acid sequences and the functional regions herein, the fragments that can be derived via restriction enzyme cutting of the DNA or proteolytic or other degradation of human factor VIII protein will be apparent to those skilled in the art.

FIX.

As used herein, FIX means Coagulation Factor IX, which is also known as Human Clotting Factor IX, or Plasma Thromboplastin Component.

FX. As used herein, FX means Coagulation Factor X, which is also known by the names Human Clotting Factor X and by the eponym Stuart-Prower factor.

Pharmacokinetics. "Pharmacokinetics" ("PK") is a term used to describe the properties of absorption, distribution, metabolism, and elimination of a drug in a body. An improvement to a drug's pharmacokinetics means an improvement in those characteristics that make the drug more effective in vivo as a therapeutic agent, especially its useful duration in the body.

Mutein. A mutein is a genetically engineered protein arising as a result of a laboratory induced mutation to a protein or polypeptide.

Protein. As used herein, protein and polypeptide are synonyms.

FVIII clearance receptor. A FVIII clearance receptor as used herein means a receptor region on a functional FVIII polypeptide that binds or associates with one or more other molecules to result in FVIII clearance from the circulation. Factor VIII clearance receptors include without limitation the regions of the FVIII molecule that bind LRP, LDL receptor and/or HSPG.

Discussion

It is envisioned that any functional factor VIII polypeptide may be mutated at a predetermined site and then covalently attached at that site to a biocompatible polymer according to the methods of the invention. Useful polypeptides include, without limitation, full-length factor VIII having the amino acid sequence as shown in SEQ ID NO:4 and BDD FVIII having the amino acid sequence as shown in SEQ ID NO:3. Preferred is BDD FVIII.

The biocompatible polymer used in the conjugates of the invention may be any of the polymers discussed above. The biocompatible polymer is selected to provide the desired improvement in pharmacokinetics. For example, the identity, size and structure of the polymer is selected so as to improve the circulation half-life of the polypeptide having FVIII activity or decrease the antigenicity of the polypeptide without an unacceptable decrease in activity. Preferably, the polymer comprises PEG, and still more preferably has at least 50% of its molecular weight as PEG. In one embodiment, the polymer is a polyethylene glycol terminally capped with an end-capping moiety such as hydroxyl, alkoxy, substituted alkoxy, alkenoxy, substituted alkenoxy, alkynoxy, substituted alkynoxy, aryloxy and substituted aryloxy. Still more preferred are polymers comprising methoxypolyethylene glycol. Yet more preferred are polymers comprising methoxypolyethylene glycol having a size range from 3 kD to 100 kD, and more preferably from 5 kD to 64 kD or from 5 kD to 43 kD.

Preferably the polymer has a reactive moiety. For example, in one embodiment, the polymer has a sulfhydryl reactive moiety that can react with a free cysteine on a functional factor VIII polypeptide to form a covalent linkage. Such sulfhydryl reactive moieties include thiol, triflate, tresylate, aziridine, oxirane, S-pyridyl or maleimide moieties. Preferred is a maleimide moiety. In one embodiment, the polymer is linear and has a "cap" at one terminus that is not strongly reactive towards sulfhydryls (such as methoxy) and a sulfhydryl reactive moiety at the other terminus. In a preferred embodiment, the conjugate comprises PEG-maleimide and has a size range from 5 kD to 64 kD.

Further guidance for selecting useful biocompatible polymers is provided in the examples that follow.

Site-directed mutation of a nucleotide sequence encoding polypeptide having FVIII activity may occur by any method known in the art. Preferred methods include mutagenesis to introduce a cysteine codon at the site chosen for covalent attachment of the polymer. This may be accomplished using a commercially available site-directed mutagenesis kit such as the Stratagene cQuickChange™ II site-directed mutagenesis kit, the Clontech Transformer site-directed mutagenesis kit no. K1600-1, the Invitrogen GenTaylor site-directed mutagenesis system no. 12397014, the Promega Altered Sites II in vitro mutagenesis system kit no. Q6210, or the Takara Mirus Bio LA PCR mutagenesis kit no. TAK RR016.

The conjugates of the invention may be prepared by first replacing the codon for one or more amino acids on the surface of the functional FVIII polypeptide with a codon for cysteine, producing the cysteine mutein in a recombinant expression system, reacting the mutein with a cysteine-specific polymer reagent, and purifying the mutein.

In this system, the addition of a polymer at the cysteine site can be accomplished through a maleimide active functionality on the polymer. Examples of this technology are provided infra. The amount of sulfhydryl reactive polymer used should be at least equimolar to the molar amount of cysteines to be derivatized and preferably is present in excess. Preferably, at least a 5-fold molar excess of sulfhydryl reactive polymer is used, and still more preferably at least a ten-fold excess of such polymer is used. Other conditions useful for covalent attachment are within the skill of those in the art.

In the examples that follow, the muteins are named in a manner conventional in the art. The convention for naming mutants is based on the amino acid sequence for the mature, full length Factor VIII as provided in SEQ ID NO:4. As a secreted protein, FVIII contains a signal sequence that is proteolytically cleaved during the translation process. Following removal of the 19 amino acid signal sequence, the first amino acid of the secreted FVIII product is an alanine.

As is conventional and used herein, when referring to mutated amino acids in BDD FVIII, the mutated amino acid is designated by its position in the sequence of full-length FVIII. For example, the PEG6 mutein discussed below is designated K1808C because it changes the lysine (K) at the position analogous to 1808 in the full-length sequence to cysteine (C).

The predefined site for covalent binding of the polymer is best selected from sites exposed on the surface of the polypeptide that are not involved in FVIII activity or involved in other mechanisms that stabilize FVIII in vivo, such as binding to vWF. Such sites are also best selected from those sites known to be involved in mechanisms by which FVIII is deactivated or cleared from circulation. Selection of these sites is discussed in detail below. Preferred sites include an amino acid residue in or near a binding site for (a) low density lipoprotein receptor related protein, (b) a heparin sulphate proteoglycan, (c) low density lipoprotein receptor and/or (d) factor VIII inhibitory antibodies. By "in or near a binding site" means a residue that is sufficiently close to a binding site such that covalent attachment of a biocompatible polymer to the site would result in steric hindrance of the binding site. Such a site is expected to be within 20 Å of a binding site, for example.

In one embodiment of the invention, the biocompatible polymer is covalently attached to the functional factor VIII polypeptide at an amino acid residue in or near (a) a factor VIII clearance receptor as defined supra, (b) a binding site for a protease capable of degradation of factor VIII and/or (c) a binding site for factor VIII inhibitory antibodies. The protease may be activated protein C (APC). In another embodiment, the biocompatible polymer is covalently attached at the predefined site on the functional factor VIII polypeptide such that binding of low-density lipoprotein receptor related protein to the polypeptide is less than to the polypeptide when it is not conjugated, and preferably more than twofold less. In one embodiment, the biocompatible polymer is covalently attached at the predefined site on the functional factor VIII polypeptide such that binding of heparin sulphate proteoglycans to the polypeptide is less than to the polypeptide when it is not conjugated, and preferably is more than twofold less. In a further embodiment, the biocompatible polymer is covalently attached at the predefined site on the functional factor VIII polypeptide such that binding of factor VIII inhibitory antibodies to the polypeptide is less than to the polypeptide when it is not conjugated, preferably more than twofold less than the binding to the polypeptide when it is not conjugated. In another embodiment, the biocompatible polymer is covalently attached at the predefined site on the functional factor VIII polypeptide such that binding of low density lipoprotein receptor to the polypeptide is less than to the polypeptide when it is not conjugated, preferably more than twofold less. In another embodiment, the biocompatible polymer is covalently attached at the predefined site on the functional factor VIII polypeptide such that a plasma protease degrades the polypeptide less than when the polypeptide is not conjugated. In a further embodiment, the degradation of the polypeptide by the plasma protease is more than twofold less than the degradation of the polypeptide when it is not conjugated as measured under the same conditions over the same time period.

LRP, LDL receptor, or HSPG binding affinity for FVIII can be determined using surface plasmon resonance technology (Biacore). For example, FVIII can be coated directly or indirectly through a FVIII antibody to a Biacore™ chip, and varying concentrations of LRP can be passed over the chip to measure both on-rate and off-rate of the interaction (Bovenschen N. et al., 2003, J. Biol. Chem. 278(11), pp. 9370-7). The ratio of the two rates gives a measure of affinity. A two-fold, preferably five-fold, more preferably ten-fold, and even more preferably 30-fold decrease in affinity upon PEGylation would be desired.

Degradation of a FVIII by the protease APC can be measured by any of the methods known to those of skill in the art.

In one embodiment, the biocompatible polymer is covalently attached to the polypeptide at one or more of the factor VIII amino acid positions 81, 129, 377, 378, 468, 487, 491, 504, 556, 570, 711, 1648, 1795, 1796, 1803, 1804, 1808, 1810, 1864, 1903, 1911, 2091, 2118 and 2284. In another embodiment, the biocompatible polymer is covalently attached to the polypeptide at one or more of factor VIII amino acid positions 377, 378, 468, 491, 504, 556, 1795, 1796, 1803, 1804, 1808, 1810, 1864, 1903, 1911 and 2284 and (1) the binding of the conjugate to low-density lipoprotein receptor related protein is less than the binding of the unconjugated polypeptide to the low-density lipoprotein receptor related protein; (2) the binding of the conjugate to low-density lipoprotein receptor is less than the binding of the unconjugated polypeptide to the low-density lipoprotein receptor; or (3) the binding of the conjugate to both low-density lipoprotein receptor related protein and low-density lipoprotein receptor is less than the binding of the unconjugated polypeptide to the low-density lipoprotein receptor related protein and the low-density lipoprotein receptor.

In a further embodiment, the biocompatible polymer is covalently attached to the polypeptide at one or more of factor VIII amino acid positions 377, 378, 468, 491, 504, 556 and 711 and the binding of the conjugate to heparin sulphate proteoglycan is less than the binding of the unconjugated polypeptide to heparin sulphate proteoglycan. In a further embodiment, the biocompatible polymer is covalently attached to the polypeptide at one or more of the factor VIII amino acid positions 81, 129, 377, 378, 468, 487, 491, 504, 556, 570, 711, 1648, 1795, 1796, 1803, 1804, 1808, 1810, 1864, 1903, 1911, 2091, 2118 and 2284 and the conjugate has less binding to factor VIII inhibitory antibodies than the unconjugated polypeptide. In a further embodiment, the biocompatible polymer is covalently attached to the polypeptide at one or more of the factor VIII amino acid positions 81, 129, 377, 378, 468, 487, 491, 504, 556, 570, 711, 1648, 1795, 1796, 1803, 1804, 1808, 1810, 1864, 1903, 1911, 2091, 2118 and 2284, and preferably at one or more of positions 377, 378, 468, 491, 504, 556, and 711 and the conjugate has less degradation from a plasma protease capable of factor VIII degradation than does the unconjugated polypeptide. More preferred, the plasma protease is activated protein C.

In a further embodiment, the biocompatible polymer is covalently attached to B-domain deleted factor VIII at amino acid position 129, 491, 1804, and/or 1808, more preferably at 491 or 1808. In a further embodiment, the biocompatible polymer is attached to the polypeptide at factor VIII amino acid position 1804 and comprises polyethylene glycol. Preferably, the one or more predefined sites for biocompatible polymer attachment are controlled by site specific cysteine mutation.

One or more sites, preferably one or two, on the functional factor VIII polypeptide may be the predefined sites for polymer attachment. In particular embodiments, the polypeptide is mono-PEGylated or diPEGylated.

The invention also relates to a method for the preparation of the conjugate comprising mutating a nucleotide sequence that encodes for the functional factor VIII polypeptide to substitute a coding sequence for a cysteine residue at a pre-defined site; expressing the mutated nucleotide sequence to produce a cysteine enhanced mutein; purifying the mutein; reacting the mutein with the biocompatible polymer that has been activated to react with polypeptides at substantially only reduced cysteine residues such that the conjugate is formed; and purifying the conjugate. In another embodiment, the invention provides a method for site-directed PEGylation of a factor VIII mutein comprising: (a) expressing a site-directed factor VIII mutein wherein the mutein has a cysteine replacement for an amino acid residue on the exposed surface of the factor VIII mutein and that cysteine is capped; (b) contacting the cysteine mutein with a reductant under conditions to mildly reduce the cysteine mutein and to release the cap; (c) removing the cap and the reductant from the cysteine mutein; and (d) at least about 5 minutes, and preferably at least 15 minutes, still more preferably at least 30 minutes after the removal of the reductant, treating the cysteine mutein with PEG comprising a sulfhydryl coupling moiety under conditions such that PEGylated factor VIII mutein is produced. The sulfhydryl coupling moiety of the PEG is selected from the group consisting of thiol, triflate, tresylate, aziridine, oxirane, S-pyridyl and maleimide moieties, preferably maleimide.

The invention also concerns pharmaceutical compositions for parenteral administration comprising therapeutically effective amounts of the conjugates of the invention and a pharmaceutically acceptable adjuvant. Pharmaceutically acceptable adjuvants are substances that may be added to the active ingredient to help formulate or stabilize the preparation and cause no significant adverse toxicological effects to the patient. Examples of such adjuvants are well known to those skilled in the art and include water, sugars such as maltose or sucrose, albumin, salts, etc. Other adjuvants are described for example in Remington's Pharmaceutical Sciences by E. W. Martin. Such compositions will contain an effective amount of the conjugate hereof together with a suitable amount of vehicle in order to prepare pharmaceutically acceptable compositions suitable for effective administration to the host. For example, the conjugate may be parenterally administered to subjects suffering from hemophilia A at a dosage that may vary with the severity of the bleeding episode. The average doses administered intraveneously are in the range of 40 units per kilogram for pre-operative indications, 15 to 20 units per kilogram for minor hemorrhaging, and 20 to 40 units per kilogram administered over an 8-hours period for a maintenance dose.

In one embodiment the inventive method involves replacing one or more surface BDD amino acids with a cysteine, producing the cysteine mutein in a mammalian expression system, reducing a cysteine which has been capped during expression by cysteine from growth media, removing the reductant to allow BDD disulfides to reform, and reacting with a cysteine-specific biocompatible polymer reagent, such as such as PEG-maleimide. Examples of such reagents are PEG-maleimide with PEG sizes such as 5, 22, or 43 kD available from Nektar Therapeutics of San Carlos, Calif. under Nektar catalog numbers 2D2M0H01 mPEG-MAL MW 5,000 Da, 2D2M0P01 mPEG-MAL MW 20 kD, 2D3X0P01 mPEG2-MAL MW 40 kD, respectively, or 12 or 33 kD available from NOF Corporation, Tokyo, Japan under NOF catalog number Sunbright ME-120MA and Sunbright ME-300MA, respectively. The PEGylated product is purified using ion-exchange chromatography to remove unreacted PEG and using size-exclusion chromatography to remove unreacted BDD. This method can be used to identify and selectively shield any unfavorable interactions with FVIII such as receptor-mediated clearance, inhibitory antibody binding, and degradation by proteolytic enzymes. We noted that the PEG reagent supplied by Nektar or NOF as 5 kD tested as 6 kD in our laboratory, and similarly the PEG reagent supplied as linear 20 kD tested as 22 kD, that supplied as 40 kD tested as 43 kD and that supplied as 60 kD tested as 64 kD in our laboratory. To avoid confusion, we use the molecular weight as tested in our laboratory in the discussion herein, except for the 5 kD PEG, which we report as 5 kD as the manufacturer identified it.

In addition to cysteine mutations at positions 491 and 1808 of BDD (disclosed above), positions 487, 496, 504, 468, 1810, 1812, 1813, 1815, 1795, 1796, 1803, and 1804 were mutated to cysteine to potentially allow blockage of LRP binding upon PEGylation. Also, positions 377, 378, and 556 were mutated to cysteine to allow blockage of both LRP and HSPG binding upon PEGylation. Positions 81, 129, 422, 523, 570, 1864, 1911, 2091, and 2284 were selected to be equally spaced on BDD so that site-directed PEGylation with large PEGs (>40 kD) at these positions together with PEGylation at the native glycosylation sites (41, 239, and 2118) and LRP binding sites should completely cover the surface of BDD and identify novel clearance mechanism for BDD.

In one embodiment, the cell culture medium contains cysteines that "cap" the cysteine residues on the mutein by forming disulfide bonds. In the preparation of the conjugate, the cysteine mutein produced in the recombinant system is capped with a cysteine from the medium and this cap is removed by mild reduction that releases the cap before adding the cysteine-specific polymer reagent. Other methods known in the art for site-specific mutation of FVIII may also be used, as would be apparent to one of skill in the art.

EXAMPLES

Structure Activity Relationship Analysis of FVIII

FVIII and BDD FVIII are very large complex molecules with many different sites involved in biological reactions. Previous attempts to covalently modify them to improve pharmacokinetic properties had mixed results. That the molecules could be specifically mutated and then a polymer added in a site-specific manner was surprising. Furthermore, the results of improved pharmacokinetic properties and retained activity were surprising also, given the problems with past polymeric conjugates causing nonspecific addition and reduced activity.

In one embodiment, the invention concerns site-directed mutagenesis using cysteine-specific ligands such as PEG-maleimide. A non-mutated BDD does not have any available cysteines to react with a PEG-maleimide, so only the mutated cysteine position will be the site of PEGylation. More specifically, BDD FVIII has 19 cysteines, 16 of which form disulfides and the other 3 of which are free cysteines (McMullen et al., 1995, Protein Sci. 4, pp. 740-746). The structural model of BDD suggests that all 3 free cysteines are buried (Stoliova-McPhie et al., 2002, Blood 99, pp. 1215-1223). Because oxidized cysteines cannot be PEGylated by PEG-maleimides, the 16 cysteines that form disulfides in BDD cannot be PEGylated without being first reduced. Based on the structural models of BDD, the 3 free cysteines in BDD may not be PEGylated without first denaturing the protein to expose these cysteines to the PEG reagent. Thus, it does not appear feasible to achieve specific PEGylation of BDD by PEGylation at native cysteine residues without dramatically altering the BDD structure, which will most likely destroy its function.

The redox state of the 4 cysteines in the B domain of full-length FVIII is unknown. PEGylation of the 4 cysteines in the B domain may be possible if they do not form disulfides and are surface exposed. However, because full-length FVIII and BDD have a similar pharmacokinetic (PK) profile and similar half-lives in vivo (Gruppo et al., 2003, Haemophilia 9, pp. 251-260), B domain PEGylation is unlikely to result in improved plasma half-life unless the PEG happens to also protect non-B domain regions.

To determine the predefined site on a polypeptide having FVIII activity for polymer attachment that will retain factor VIII activity and improve pharmacokinetics, the following guidelines are presented based on BDD FVIII. Modifications should be targeted toward clearance, inactivation, and immunogenic mechanisms such as LRP, HSPG, APC, and inhibitory antibody binding sites. Stoilova-McPhie, S. et al., 2002, Blood 99(4), pp. 1215-23 shows the structure of BDD. For example, to prolong half-life, a single PEG can be introduced at a specific site at or near LRP binding sites in A2 residues 484-509 and A3 residues 1811-1818. Introduction of the bulky PEG at these sites should disrupt FVIII's ability to bind LRP and reduce the clearance of FVIII from circulation. It is also believed that to prolong half-life without significantly affecting activity that a PEG can be introduced at residue 1648, which is at the junction of the B domain and the A3 domain in the full-length molecule and in the 14-amino acid liker I the BDD between the A2 and A3 domains.

Specificity of PEGylation can be achieved by engineering single cysteine residues into the A2 or A3 domains using recombinant DNA mutagenesis techniques followed by site-specific PEGylation of the introduced cysteine with a cysteine-specific PEG reagent such as PEG-maleimide. Another advantage of PEGylating at 484-509 and 1811-1818 is that these two epitopes represent two of the three major classes of inhibitory antigenic sites in patients. To achieve maximal effect of improved circulating half-life and reduction of immunogenic response, both A2 and A3 LRP binding sites can be PEGylated to yield a diPEGylated product. It should be noted that PEGylation within the 1811-1818 region may lead to significant loss of activity since this region is also involved in FIX binding. Site-directed PEGylation within 558-565 should abolish HSPG binding, but may also reduce activity as this region also binds to FIX.

Additional surface sites can be PEGylated to identify novel clearance mechanism of FVIII. PEGylation of the A2 domain may offer additional advantage in that the A2 domain dissociates from FVIII upon activation and is presumably removed from circulation faster than the rest of FVIII molecule because of its smaller size. PEGylated A2, on the other hand, may be big enough to escape kidney clearance and have a comparable plasma half-life to the rest of FVIII and thus can reconstitute the activated FVIII in vivo.

Identification of Pegylation Sites in A2 and A3 Regions.

Five positions (Y487, L491, K496, L504 and Q468 corresponding to PEG1-5 positions) at or near the putative A2 LRP binding region were selected as examples for site-directed PEGylation based on the high surface exposure and outward direction of their Cα to Cβ trajectory. Furthermore, these residues are roughly equidistant from each other in the three-dimensional structure of the molecule, so that together they can represent this entire region. Eight positions (1808, 1810, 1812, 1813, 1815, 1795, 1796, 1803, 1804 corresponding to PEG6-14) at or near the putative A3 LRP binding region were selected as examples for site-directed PEGylation. PEG6 (K1808) is adjacent to 1811-1818 and the natural N-linked glycosylation site at 1810. PEGylation at position 1810 (PEG7) will replace the sugar with a PEG. Mutation at the PEG8 position T1812 will also abolish the glycosylation site. Although the PEG9 position (K1813) was predicted to be pointing inward, it was selected in case the structure model is not correct. PEG10 (Y1815) is a bulky hydrophobic amino acid within the LRP binding loop, and may be a critical interacting residue since hydrophobic amino acids are typically found at the center of protein-protein interactions. Because the 1811-1818 region has been reported to be involved in both LRP and FIX binding, PEGylation within this loop was thought possibly to result in reduced activity. Thus, PEG11-PEG14 (1795, 1796, 1803, 1804) were designed to be near the 1811-1818 loop but not within the loop so that one can dissociate LRP and FIX binding with different PEG sizes.

To block both LRP binding sites simultaneously, double PEGylation at, for example, the PEG2 and PEG6 position, can be generated.

Since the 558-565 region has been shown to bind to both HSPG and FIX, no sites were designed within this region. Instead, PEG15-PEG17 (377, 378, and 556) were designed in between the A2 LRP and HSPG binding regions so that an attached PEG may interfere both interactions and disrupt possible interactions between them. Additional sites that are surface exposed and outwardly pointing could also be selected within or near the LRP and HPSG binding regions. To identify novel clearance mechanisms, FVIII can be systematically PEGylated. In addition to PEG1-17, the three other natural glycosylation sites, namely, N41, N239, and N2118 corresponding to PEG18-20 can be used as tethering points for PEGylation since they should be surface exposed. Surface areas within a 20 angstrom radius from the C13 atoms of PEG2, PEG6, and the four glycosylation sites were mapped onto the BDD model in addition to functional interaction sites for vWF, FIX, FX, phospholipid, and thrombin.

PEG21-29 corresponding to Y81, F129, K422, K523, K570, N1864, T1911, Q2091, and Q2284 were then selected based on their ability to cover nearly the entire remaining BDD surface with a 20 angstrom radius from each of their Cβ atoms. These positions were also selected because they are fully exposed, outwardly pointing, and far away from natural cysteines to minimize possible incorrect disulfide formation. The 20 angstrom radius is chosen because a large PEG, such as a 64 kD branched PEG, is expected to have the potential to cover a sphere with about a 20 angstrom radius. PEGylation of PEG21-29 together with PEG2 and PEG6 and glycosylation sites PEG18, 19, and 20 is likely to protect nearly the entire non-functional surface of FVIII.

PEGylation positions that lead to enhanced properties such as improved PK profile, greater stability, or reduced immunogenicity can be combined to generate multi-PEGylated product with maximally enhanced properties. PEG30 and PEG31 were designed by removing the exposed disulfides in A2 and A3 domain, respectively. PEG30, or C630A, should free up its disulfide partner C711 for PEGylation. Likewise, PEG31, C1899A should allow C1903 to be PEGylated.

Mutagenesis.

Substrates for site-directed PEGylation of FVIII may be generated by introducing a cysteine codon at the site chosen for PEGylation. The Stratagene cQuickChange™ II site-directed mutagenesis kit was used to make all of the PEG mutants (Stratagene kit 200523 from Stratagene Corporation, La Jolla, Calif.). The cQuikChange™ site-directed mutagenesis method is performed using PfuTurbo® DNA polymerase and a temperature cycler. Two complimentary oligonucleotide primers, containing the desired mutation, are elongated using PfuTurbo, which will not displace the primers. dsDNA containing the wildtype FVIII gene is used as a template. Following multiple elongation cycles, the product is digested with Dpnl endonuclease, which is specific for methylated DNA. The newly synthesized DNA, containing the mutation, is not methylated, whereas the parental wild-type DNA is methylated. The digested DNA is then used to transform XL-1 Blue super-competent cells.

Figure 1B:
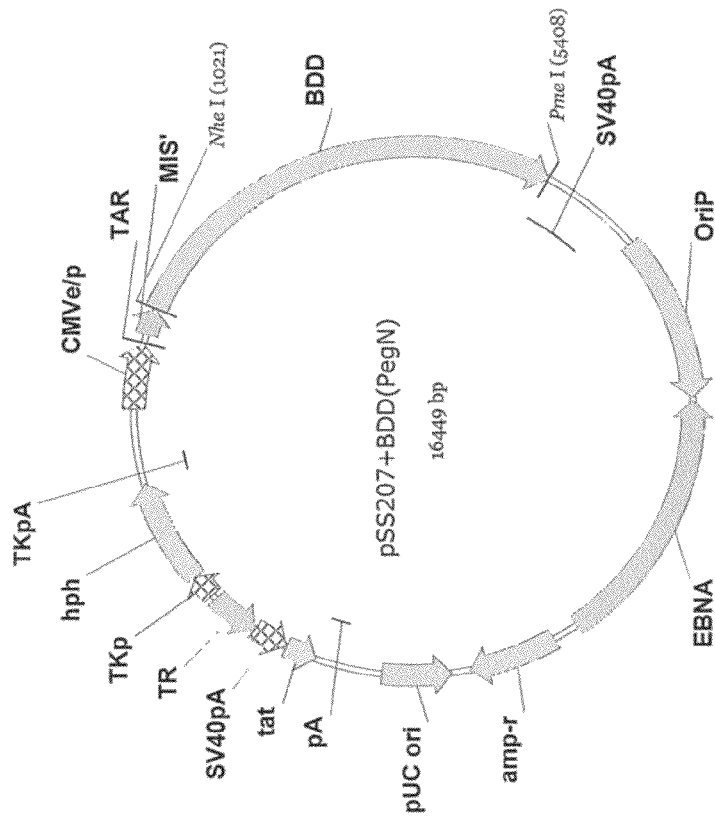

The mutagenesis efficiency is almost 80%. The mutagenesis reactions were performed in either pSK207+BDD C2.6 or pSK207+BDD (FIG. 1). Successful mutagenesis was confirmed by DNA sequencing and appropriate fragments, containing the mutation, were transferred into the FVIII backbone in the mammalian expression vector pSS207+BDD. After transfer, all of the mutations were again sequence-confirmed. For A3 muteins PEG 6, 7, 8, 9, and 10, mutagenesis was done in the vector pSK207+BDD C2.6. After being confirmed by sequencing, the mutant fragment, KpnI/Pme was subcloned into pSK207+BDD. The BDD mutein was then subcloned into the pSS207+BDD expression vector. For A3 muteins PEG 11, 12, 13, 14, the mutagenesis was done directly in the vector pSK207+BDD and sequence-confirmed mutant BDD were then subcloned into pSS207+BDD. For A2 muteins PEG 1, 2, 3, 4, 5, the mutagenesis was done in the pSK207+BDD C2.6vector. The sequence confirmed mutant was subcloned into pSK207+BDD and then to pSS207+BDD.

The Primers (Sense Stand Only) Used for Mutagenesis are Listed for Each Reaction

PEG1, Y487C:
(SEQ ID NO: 5)
GATGTCCGTCCTTTGTGCTCAAGGAGATTACCA

PEG2, L491C:
(SEQ ID NO: 6)
TTGTATTCAAGGAGATGCCCAAAAGGTGTAAAAC

PEG3, K496C:
(SEQ ID NO: 7)
TTACCAAAAGGTGTATGCCATTTGAAGGATTTTC

PEG4, L504C:
(SEQ ID NO: 8)
AAGGATTTTCCAATTTGCCCAGGAGAAATATTC

PEG5, Q468C:
(SEQ ID NO: 9)
GATTATATTTAAGAATTGCGCAAGCAGACCATAT

PEG6, K1808C:
(SEQ ID NO: 10)
TAGAAAAACTTTGTCTGCCCTAATGAAACCAAAAC

PEG7, N1810C:
(SEQ ID NO: 11)
AACTTTGTCAAGCCTTGCGAAACCAAAACTTAC

PEG8, T1812C:
(SEQ ID NO: 12)
GTCAAGCCTAATGAATGCAAAACTTACTTTTGGA

PEG9, K1813C:
(SEQ ID NO: 13)
CAAGCCTAATGAAACCTGCACTTACTTTTGGAAAG

PEG10, Y1815C:
(SEQ ID NO: 14)
CTAATGAAACCAAAACTTGCTTTTGGAAAGTGCAAC

PEG11, D1795C:
(SEQ ID NO: 15)
ATTTCTTATGAGGAATGCCAGAGGCAAGGAGCA

PEG12, Q1796C:
(SEQ ID NO: 16)
TCTTATGAGGAAGATTGCAGGCAAGGAGCAGAA

PEG13, R1803C:
(SEQ ID NO: 17)
CAAGGAGCAGAACCTTGCAAAAACTTTGTCAAGCCT

PEG14, K1804C:
(SEQ ID NO: 18)
GGAGCAGAACCTAGATGCAACTTTGTCAAGCCT

PEG15, K377C:
(SEQ ID NO: 19)
CGCTCAGTTGCCAAGTGTCATCCTAAAACTTGG

PEG16, H378C:
(SEQ ID NO: 20)
TCAGTTGCCAAGAAGTGTCCTAAAACTTGGGTA

PEG17, K556C:
(SEQ ID NO: 21)
CTCCTCATCTGCTACTGCGAATCTGTAGATCAA

PEG18, N41C:
(SEQ ID NO: 22)
CAAAATCTTTTCCATTCTGCACCTCAGTCGTGTAC

-continued

PEG19, N239C:
(SEQ ID NO: 23)
GTCAATGGTTATGTATGCAGGTCTCTGCCAGGT

PEG20, N2118C:
(SEQ ID NO: 24)
CAGACTTATCGAGGATGTTCCACTGGAACCTTA

PEG21, Y81C:
(SEQ ID NO: 25)
ATCCAGGCTGAGGTTTGTGATACAGTGGTCATT

PEG22, F129C:
(SEQ ID NO: 26)
GAAGATGATAAAGTCTGTCCTGGTGGAAGCCAT

PEG23, K422C:
(SEQ ID NO: 27)
CAGCGGATTGGTAGGTGTTACAAAAAAGTCCGA

PEG24, K523C:
(SEQ ID NO: 28)
GAAGATGGGCCAACTTGCTCAGATCCTCGGTGC

PEG25, K570C:
(SEQ ID NO: 29)
CAGATAATGTCAGACTGCAGGAATGTCATCCTG

PEG26, N1864C:
(SEQ ID NO: 30)
CACACTAACACACTGTGTCCTGCTCATGGGAGA

PEG27, T1911C,
(SEQ ID NO: 31)
CAGATGGAAGATCCCTGCTTTAAAGAGAATTAT

PEG28, Q2091C:
(SEQ ID NO: 32)
ACCCAGGGTGCCCGTTGCAAGTTCTCCAGCCTC

PEG29, Q2284C:
(SEQ ID NO: 33)
AAAGTAAAGGTTTTTTGCGGAAATCAAGACTCC

PEG30, C630A:
(SEQ ID NO: 34)
TTGCAGTTGTCAGTTGCTTTGCATGAGGTGGCA

PEG31, C1899A:
(SEQ ID NO: 35)
AATATGGAAAGAAACGCTAGGGCTCCCTGCAAT

Mutein Expression.

After insertion in a vector that confers resistance to Hygromycin B, the PEG muteins were transfected into HKB11 cells (U.S. Pat. No. 6,136,599) complexed with 293 Fectin Transfection Reagent (Invitrogen Corp. Cat#12347-019) per the manufacturer's instructions. FVIII expression at three days post-transfection was assessed by Coatest chromogenic assay (Chromogenix Corp. Cat#821033, see Example 12 Chromogenic Assay) (Table 1). The transfected cells were then placed under selective pressure with 50 μg/ml of Hyg B in a growth medium supplemented with 5% FBS. When Hyg B-resistant colonies appeared, they were manually picked and screened for FVIII expression by Coatest chromogenic assay. The FVIII expressing stable cells were then adapted to a medium containing HPPS supplement. The cells were expanded and seeded at 1×106 cells/ml in shaking flasks with fresh media. Tissue culture fluid (TCF), harvested after 3 days, was used for purification of FVIII BDD muteins. The FVIII activity of the TCF was assayed by Coatest (Table 1).

Summary of PEG Mutein Titers

TABLE 1

Expression level of PEG Muteins from transient and stable transfections.

| | | Titer (IU/ml) | |
|---|---|---|---|
| Mutation | Mutein ID | Transient | Stable Cells |
| Y487C | PEG1 | 0.07 | N/A |
| L491C | PEG2 | 0.60 | 1.96 |
| K496C | PEG3 | 0.45 | N/A |
| L504C | PEG4 | 0.38 | 5.57 |
| Q468C | PEG5 | 0.69 | 8.14 |
| K1808C | PEG6 | 0.54 | 2.73 |
| N1810C | PEG7 | 0.21 | 0.5 |
| T1812C | PEG8 | 0.16 | N/A |
| K1813C | PEG9 | 0.35 | 7.74 |
| Y1815C | PEG10 | 0.09 | N/A |
| D1795C | PEG11 | 0.27 | N/A |
| Q1796C | PEG12 | 0.29 | N/A |
| R1803C | PEG13 | 0.11 | N/A |
| K1804C | PEG14 | 0.18 | 1.14 |
| L491C/K1808C | PEG2 + 6 | 0.11 | 2.48 |
| L491C/K1804C | PEG2 + 14 | 0.13 | 7.19 |
| K377C | PEG15 | 0.11 | 12.58 |
| H378C | PEG16 | 0.15 | 0.97 |
| K556C | PEG17 | 0.09 | 0.15 |
| N41C | PEG18 | 0.05 | N/A |
| N239C | PEG19 | 0.16 | N/A |
| N2118C | PEG20 | 0.13 | N/A |
| Y81C | PEG21 | 0.36 | N/A |
| F129C | PEG22 | 0.25 | 2.55 |
| K422C | PEG23 | 0.28 | N/A |
| K523C | PEG24 | <0.05 | N/A |
| K570C | PEG25 | <0.05 | N/A |
| N1864C | PEG26 | 0.15 | N/A |
| T1911C | PEG27 | 0.28 | N/A |
| Q2091C | PEG28 | 0.20 | N/A |
| Q2284C | PEG29 | 0.17 | N/A |
| C630A | PEG30 | <0.05 | 0.20 |
| C1899A | PEG31 | 0.30 | 1.80 |

Mutein Purification.

Upon collecting the cell culture supernatant containing the secreted mutein FVIII protein, the supernatant is filtered through a 0.2 micron membrane filter to remove any remaining cells. The supernatant is then concentrated by either ultrafiltration or anion exchange. It is then applied to an immunoaffinity column where the cell culture media components and the majority of the host cell protein impurities are removed. The immunoaffinity column eluate is then buffer exchanged by diafiltration into a formulation buffer containing sucrose and frozen. Yield and recovery of protein across a monoclonal FVIII antibody column was assessed by chromogenic assay. Samples of load, flow through, various eluate fractions, strip, and the diafiltered eluate of a chromatography run were assayed for FVIII activity (Table 2). Table 2 shows the recovery of the PEG2 mutein from a monoclonal antibody column. The antibodies are C7F7 antibodies. The percent recovery in Table 2 is determined by the chromogenic assay. The final yield was 73%. Shown in FIG. 2 is a plot of the UV absorbance at 280 nm with respect to time for the PEG2 protein purified over a monoclonal FVIII antibody chromatography column. The chromatography was performed using an AKTA® Explorer 100 chromatography system from Amersham Bioscience. This instrument employs a multi-wavelength UV-Visible monitor and a 2 mm flow cell. The PEG2 mutein is eluted from the column in the presence of high salt and elution peak is indicated by both the absorbance at 280 nm and FVIII activity assay.

TABLE 2

Recovery of PEG2 mutein from monoclonal FVIII antibody column.

| Step | % Recovery |
|---|---|
| C7F7 Load | 100 |
| C7F7 Flow through | 1.1 |
| C7F7 Wash | 0.2 |
| C7F7 Eluate | 86 |
| C7F7 Strip | 0.0 |
| Post UF/DF | 73 |

Pegylation.

Native full-length FVIII or BDD cannot be PEGylated by cysteine-specific PEGs without reduction and denaturation at over 100-fold excess PEG: protein ratio (data not shown), confirming the hypothesis based on the BDD structure model that all native cysteines form disulfides or are buried within FVIII. FVIII cysteine muteins expressed and purified using the standard protocols listed above could not be PEGylated with a cysteine-specific PEG maleimide reagent, presumably because the introduced FVIII cysteine is "capped" by reacting with sulfhydryl groups such as cysteine and β-mecaptoethanol present in the cell growth media. This issue can potentially be resolved by eliminating cysteines and β-mecaptoethanol from the culture media, but this may lead to lower FVIII production and would not prevent sulfhydryls released by the cells from blocking the introduced FVIII cysteine.

Figure 3:
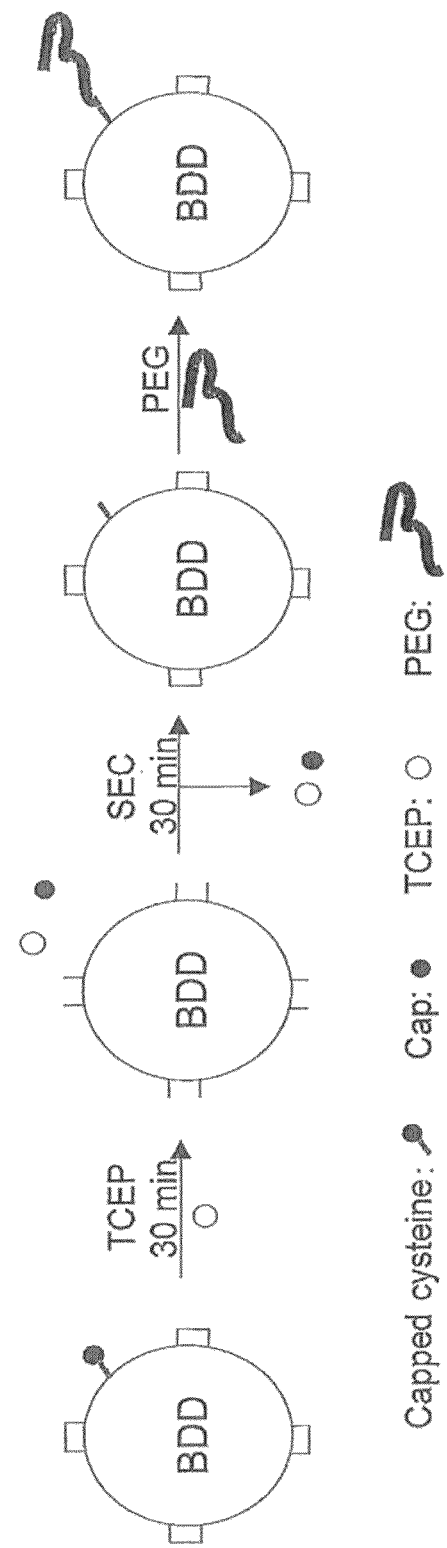
FIG. 3 Three-step site-directed PEGylation method. PEG represents a cysteine-reactive PEG such as PEG-maleimide. Closed bars represent disulfide formation while open bars represent reduced cysteines.

In another aspect of the invention, a three-step method was developed to allow site-specific PEGylation of FVIII (FIG. 3). In step 1, the purified FVIII cysteine mutein at about 1 µM is mildly reduced with reductants such as about 0.7 mM Tris(2-carboxyethyl)phosphine (TCEP) or 0.07 mM dithiothreitol (DTT) for 30 minutes at 4° C. to release the "cap." In step 2, the reductant is removed along with the "cap" by a size-exclusion chromatography (SEC) method such as running the sample through a spin column (BioRad®) to allow FVIII disulfides to reform while leaving the introduced cysteine free and reduced. In step 3, at least 30 minutes after the removal of the reductant, the freed FVIII cysteine mutein is treated with at least 10-fold molar excess of PEG-maleimide with sizes ranging from 5 to 64 kD (Nektar Therapeutics and N.O.F. Corporation) for at least 1 hour at 4° C. This method yields highly consistent product profile with reproducible data for dozens of reactions repeated by different individuals.

Because the spin column method for removal of TCEP is not scaleable, gel filtration desalting chromatography was selected. However, upon testing this method using a TCEP spike sample, it was shown that the TCEP eluted at measurable levels in the column void and not just in the salt fraction as would be expected from a molecule with its low molecular weight. Western Blot assays showed significant background PEGylation probably due to incomplete removal of TCEP. In the meantime separate experiments showed that C7F7 purified material could be significantly purified further from other protein impurities using an anion exchange chromatography media combined with a salt gradient. It was then decided to reduce the C7F7 material with TCEP as described above and then process the material over the anion exchange column. Because of charge difference the FVIII protein would be retained while the TCEP would flow through the column and not be retained. At the same time during the gradient salt elution the FVIII protein would be purified away from the majority of remaining protein impurities. This meant that the later occurring PEGylation would be theoretically more homogeneous with purer starting material. However, upon testing with a spike sample of TCEP, it was shown that measurable levels of TCEP were found eluting in the gradient with the FVIII. Therefore it was decided to implement gel filtration desalting chromatography after anion exchange chromatography so these two steps when used in sequence would result in complete removal of TCEP and elimination of non-specific PEGylation.

Pegylation Analysis by SDS Page and Western Blot.

The PEGylated product can be analyzed by electrophoresis on a reducing 6% TrisGlycine SDS polyacrylamide gel (Invitrogen). Following electrophoresis, the gel can be stained with Coomassie Blue to identify all the proteins or subjected to a standard Western Blot protocol to identify PEGylation pattern on different regions of FVIII. Staining of the blot with a mouse monoclonal R8B12 or C7F7 antibody raised against the C-terminal region of the FVIII heavy chain or the N-terminal region of the VIII light chain, respectively, should identify PEGylation of the respective chains. Staining with the 413 antibody against the 484-509 region of FVIII will determine whether PEGylation is indeed site-specific or not for muteins such as PEG1-4. Likewise, staining with the CLB-CAg A antibody that recognizes the 1801-1823 region of FVIII will determine if PEGylation is site-specific or not for muteins such as PEG6-10.

Figure 4:
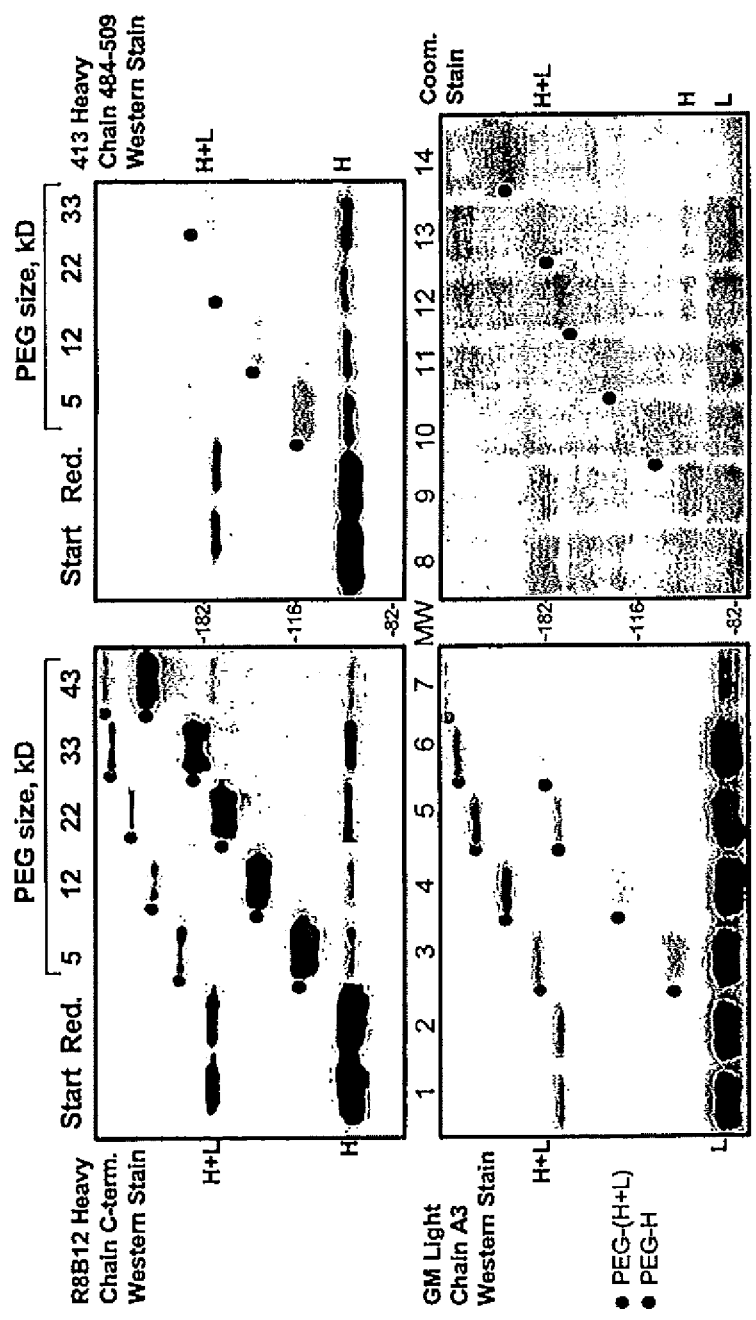
FIG. 4. Site-directed PEGylation of PEG2.
Figure 5:
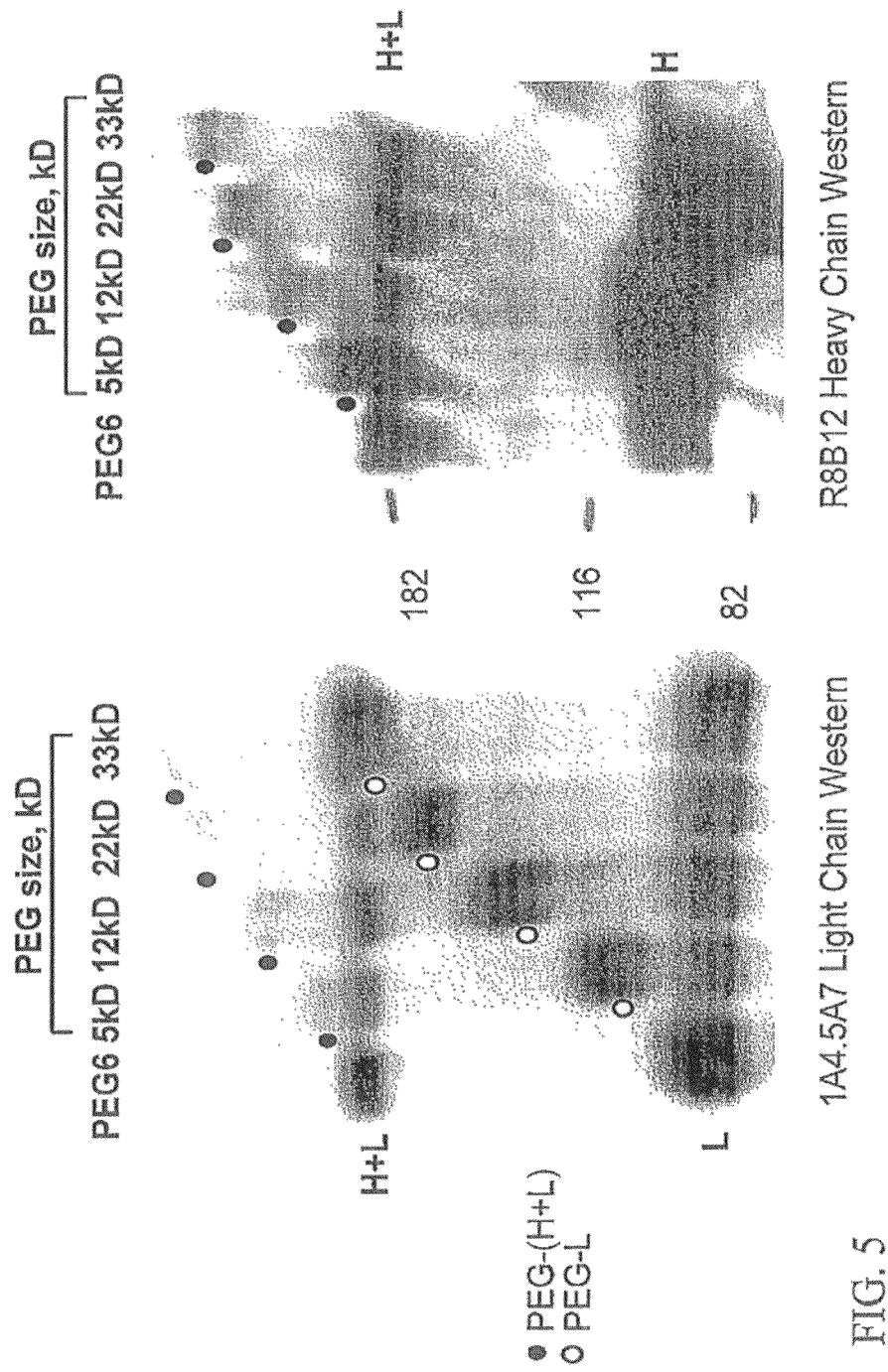
FIG. 5. Site-directed PEGylation of PEG6.

PEG2 (L491C) PEGylation was shown to be selective for the heavy chain over light chain and particularly selective for the 484-509 region (FIG. 4) while PEG6 (K1808C) was shown to be selective for the light chain over the heavy chain (FIG. 5).

For the study depicted in FIG. 4, the PEG2 mutein (lanes 1 and 8) is reduced with TCEP followed by TCEP removal (lanes 2 and 9) and treatment with 5, 12, 22, 33, or 43 kD PEG-maleimide (lanes 3-7 and 10-14). UnPEGylated FVIII runs as unprocessed (H+L) and processed heavy (H) and light (L) chain bands. All three bands are detectable on the Coomassie Blue stained gel (lower right) whereas Western Staining with chain-specific antibodies reveal only the unprocessed and the corresponding chain. Using R8B12 staining (upper left), the heavy chain (H) band is dramatically reduced in intensity when PEG2 is treated with PEG-maleimide and a new band is created that runs higher than the parent H band proportional to the size of the PEG. Using C7F7 staining (lower left), the light chain (L) bands (multiple bands due to heterogenous glycosylation) do not change intensity. The unprocessed H+L band for both stains are shifted because the H chain is part of the unprocessed FVIII. Coomassie staining also confirms much more PEGylation of the heavy chain, i.e. reduction of H band intensity, than of the light chain. Finally, the PEGylated bands lose relatively more intensity on the 413 antibody stain (upper right) than R8B12 stain in a PEG size-dependent fashion presumably due to site-specific PEGylation of 491, which blocks the binding of 413 antibody to 484-509. Quantities of FVIII loaded per lane are about 30 ng for the two left gels, about 1000 ng for the upper right gel, and about 2000 ng for the lower right gel.

Reduction followed by removal of reductant does not change the migration of FVIII (lane 1 vs. 2 and 8 vs. 9). Addition of 22 kD PEG to PEG2 blocks the binding of the 413 antibody, consistent with specific PEGylation at the 491 position (FIG. 4 upper right gel). This also suggests that PEGylated PEG2 will have lower immunogenicity in man because the 413 antibody has been shown to share the same epitope as human A2 inhibitory antibodies (Scandella et al., 1992, Thromb. Haemost. 67, pp. 665-71).

For the study depicted in FIG. 5, the PEG6 mutein is reduced with TCEP followed by TCEP removal (lanes 1 and 6) and treatment with 5, 12, 22, or 33 kD PEG-maleimide (lanes 2-5 and 7-10). UnPEGylated FVIII runs as unprocessed (H+L) and processed heavy (H) and light (L) chain bands. Because the PEG6 (K1808) mutation resides on the light chain, PEGylation was detected only on the light chain and not the heavy chain. Amount of FVIII loaded per lane is about 100 ng for the left gel and about 30 ng for the right gel.

Figure 6A:
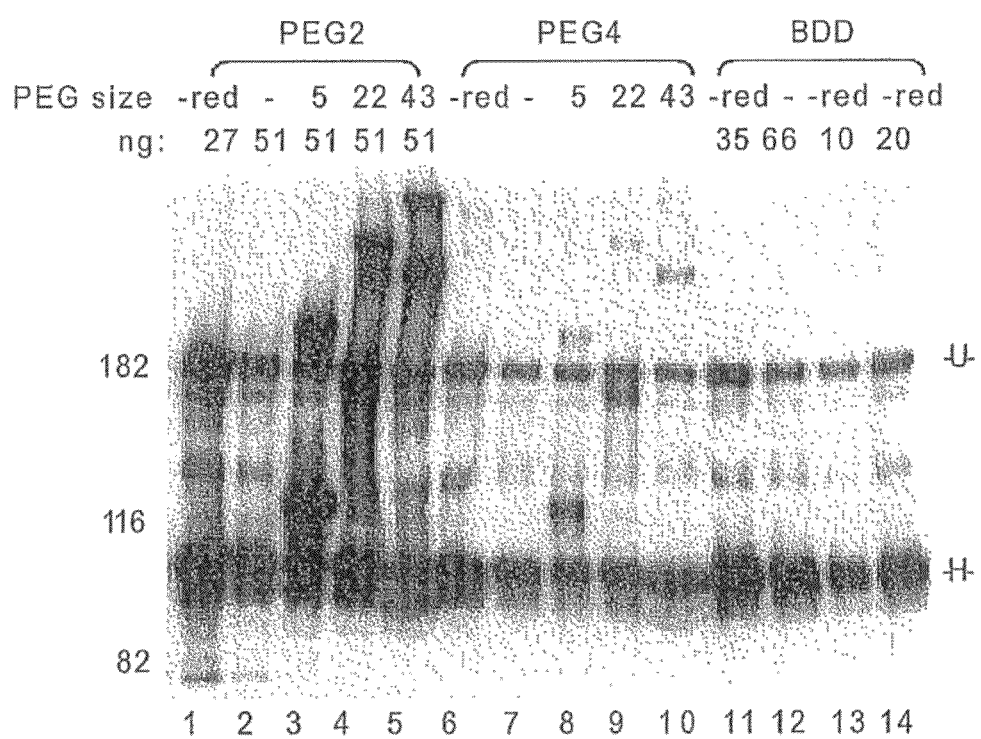
FIG. 6A-6D. Site-directed PEGylation of BDD, PEG2, 4, 5, and 6.
Figure 6B:
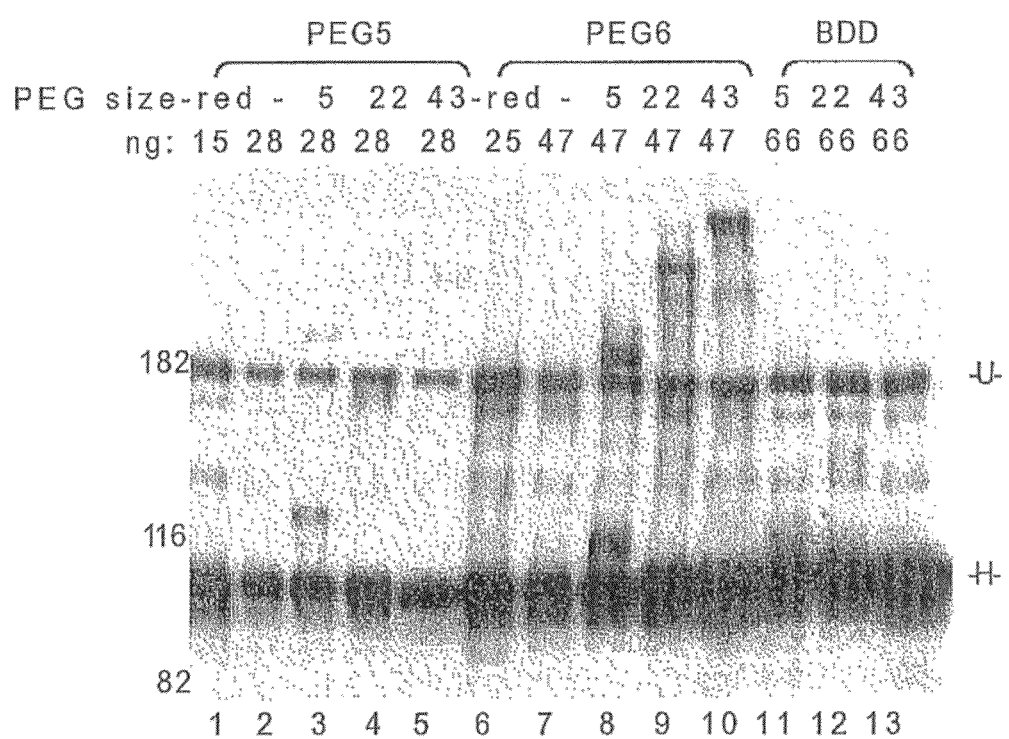
Figure 6C:
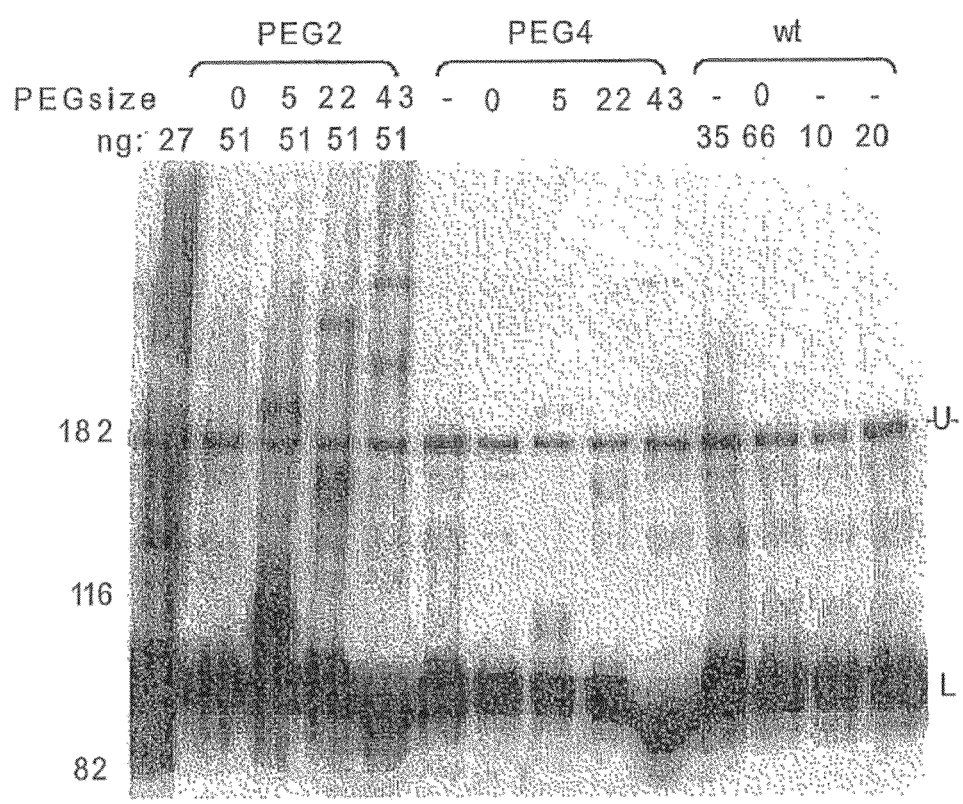
Figure 6D:
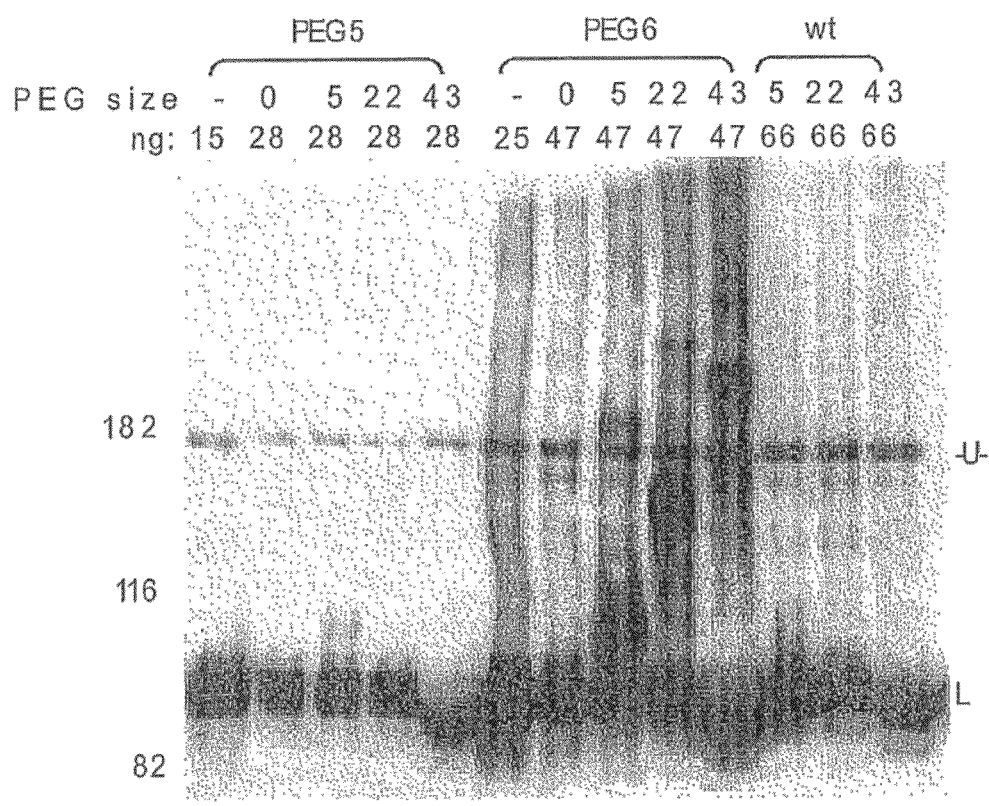
Figure 6E:
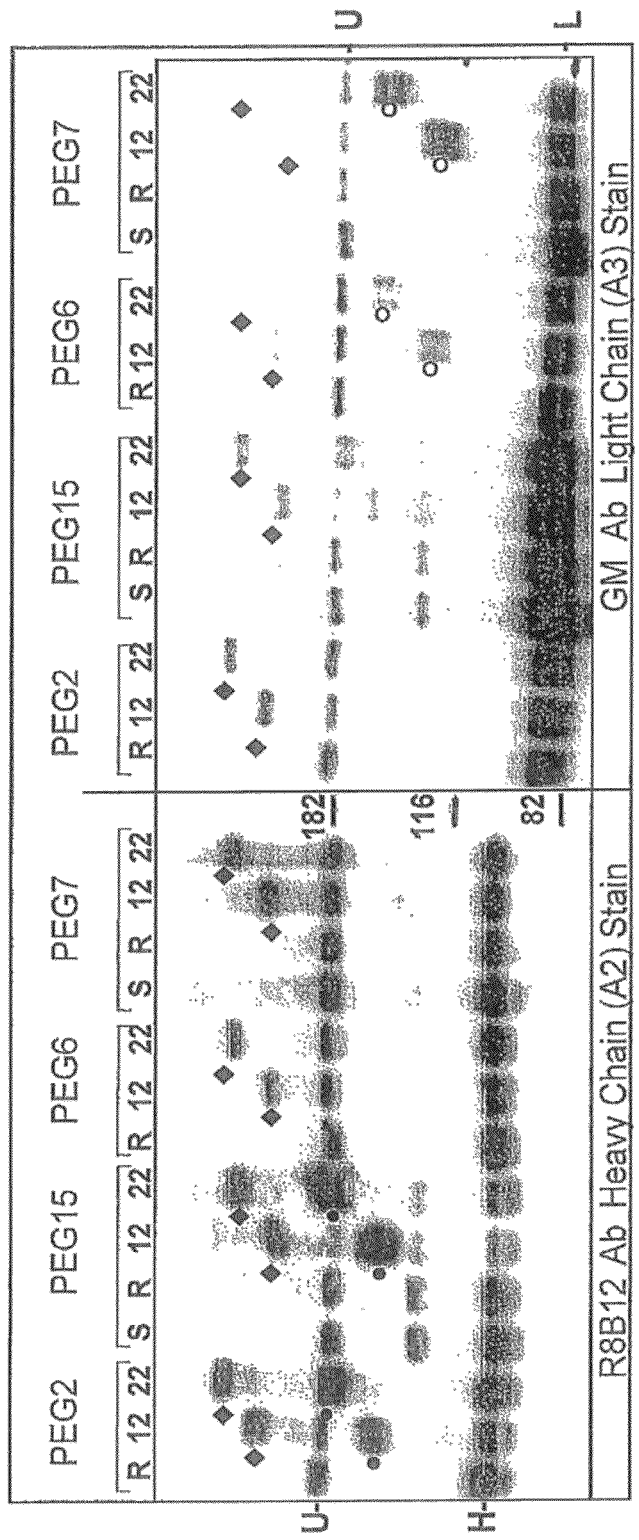
FIG. 6E. PEGylation of PEG15 and PEG7 with PEG2 and PEG6 as controls. Start purified PEG muteins ("S") are reduced with TCEP and PEGylated with a 12 kD ("12") or a 22 kD ("22") PEG after removal of the reductant ("R"). Samples were run on 6% Tris-glycine SDS PAGE and stained with a heavy chain ("NC") antibody on left panel or light chain ("LC") antibody on right panel. "U" is unprocessed material containing both HC & LC. PEGylated bands are highlighted by dots.
Figure 6F:
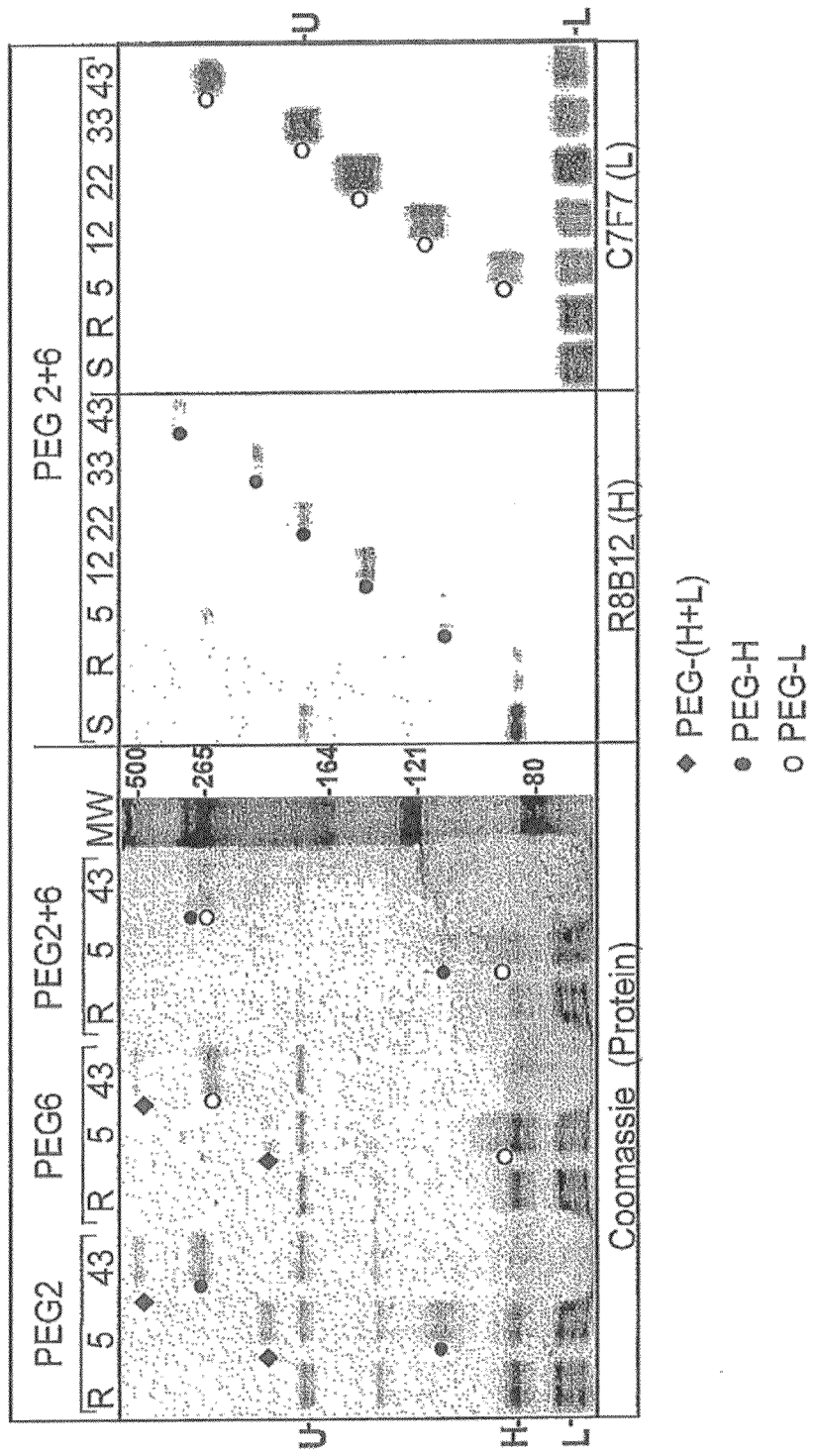
FIG. 6F. PEGylation of PEG2+6 with PEG2 and PEG6 as controls. PEG2, PEG6, or PEG2+6 is reduced with TCEP and PEGylated with a 5 kD ("5") or a 43 kD ("43") PEG after removal of the reductant ("R"). PEG2+6 was also PEGylated with 12, 22, and 33 kD PEGs. Samples were run on 6% Tris-glycine SDS PAGE and stained with coomassie for proteins on the left or heavy chain (H) or light chain (L) antibody. "U" is unprocessed material containing both H & L. PEGylated bands are highlighted by dots.
Figure 6G:
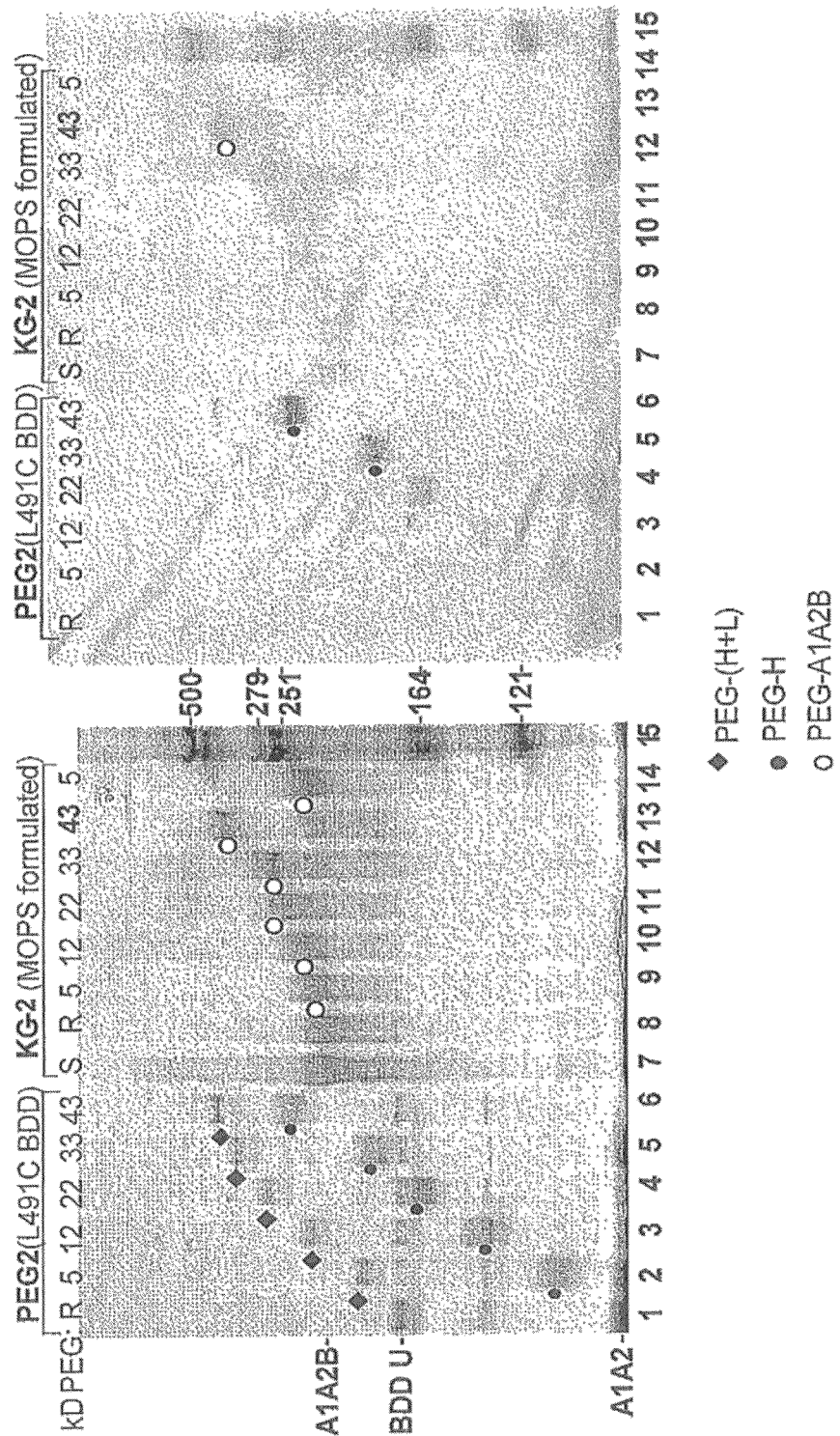
FIG. 6G. PEGylation of wildtype full length FVIII (KG-2) with PEG2 as a control. Left gel stained with coomassie stain for proteins and right gel with iodine for PEG. "BDD U" is unprocessed BDD material containing both H & L. PEGylated bands are highlighted by dots.

The BDD that was run as a control did not show any significant PEGylation upon treatment with greater than 100-fold molar excess of PEG-maleimide even after the reduction and reductant removal procedure described above (FIGS. 6A-6D). The same method was also applied to PEG4 and PEG5 (FIG. 6A-6D). Compared to PEG2, these muteins were not PEGylated as efficiently, but they were selective for the heavy chain similar to PEG2 (L491C). PEG6 (K1808C) PEGylation efficiency is relatively low, perhaps because it is very close to the N-linked glycosylation site at N1810, which may block PEGylation at position 1808. Thus, we designed PEG7 (N1810C) to remove the native glycosylation site at 1810. PEG7 shows improved PEGylation efficiency compared to PEG6 in a head-to-head comparison (FIG. 6E). Similarly PEG15 shows slightly better PEGylation efficiency than PEG2. PEG2+6, a double mutant of BDD, can be PEGylated on both heavy and light chains since PEG2 is a heavy chain cysteine mutation while PEG6 is a light chain mutation (FIG. 6F). This method was also applied to wildtype full-length FVIII (FIG. 6G). PEGylation was detected for the largest fragment of heavy chain that includes A1, A2, and most of the B domain. The PEGylation pattern suggests monoPEGylation and that there is only a single cysteine PEGylated.

Pegylation Analysis by Thrombin Cleavage and Western Blot.

Figure 7:
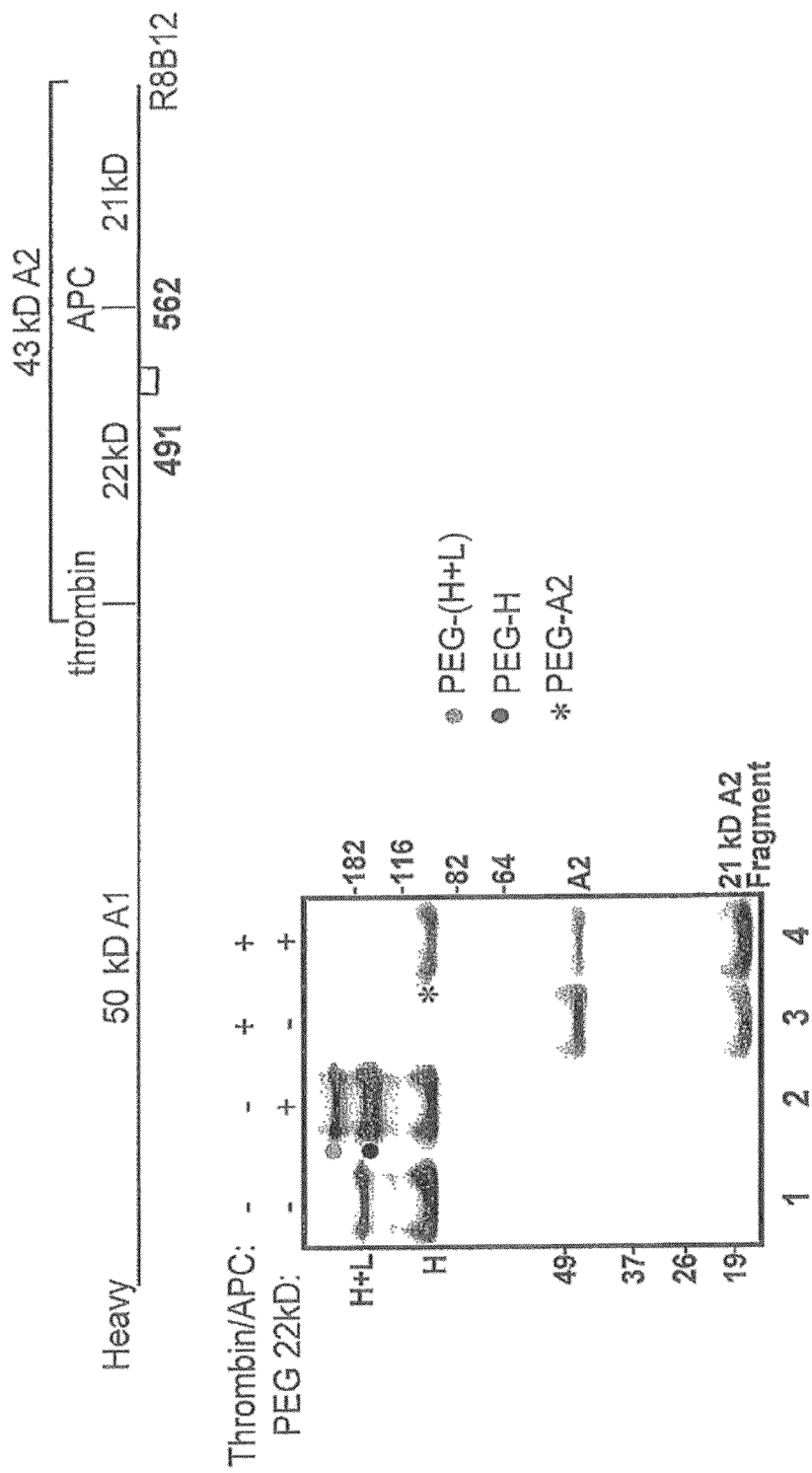
FIG. 7. Thrombin cleavage of PEGylated PEG2. The N-terminal half of A2 domain is colored in blue and C-terminal half in green, with the R8B12 antibody epitope highlighted in dark green (right FVIII model). PEG2 (lane 1) and 22 kD PEGylated PEG2 (lane2) were treated with thrombin (lanes 3 and 4, respectively) and then run on a 7% Tris-Acetate gel (Invitrogen) and stained with the R8B12 antibody. Each lane contains about 50 ng of FVIII.
Figure 8:
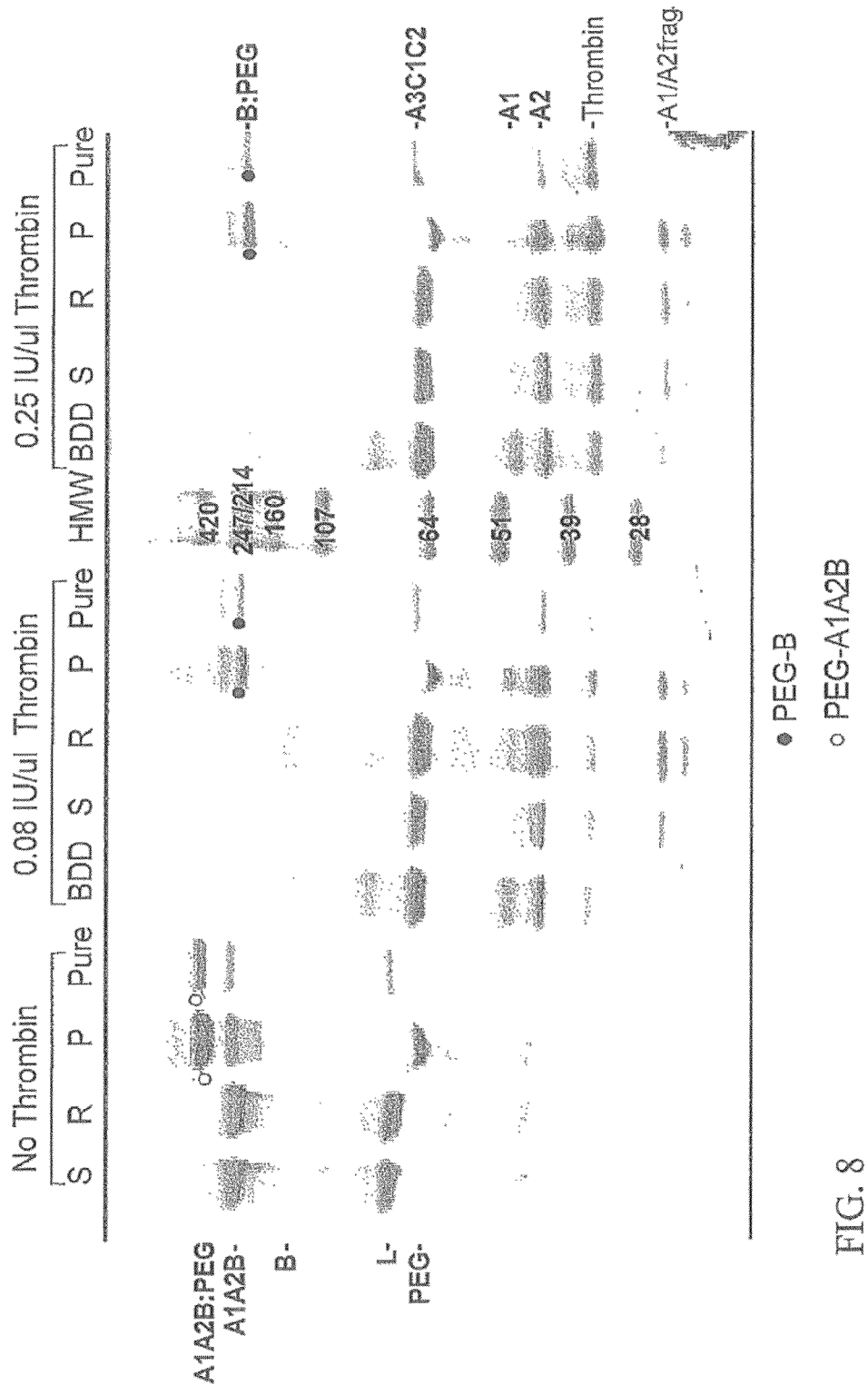
FIG. 8. Thrombin cleavage of PEGylated wildtype full-length FVIII (KG-2). "S"=starting KG-2 material. "R"=reduced KG-2 and reductant removed. "P"="R" PEGylated with 43 kD PEG. "Pure"="P" purified away from excess PEG. "L"=light chain. PEGylated bands are highlighted by dots.

The PEGylated product can be treated with thrombin (40 IU/ug FVIII) at 37° C. for 30 minutes. The thrombin used also contains APC as a contaminant. Thrombin cleavage will generate the 50 kD A1 and 43 kD A2 domains from the heavy chain while the APC cleavage will split the A2 domain further into the 21 and 22 kD fragments (FIG. 7). Staining with the R8B12 antibody, which recognizes the C-terminus of the heavy chain, will identify only the intact A2 domain and the 21 kD C-terminal fragment (FVIII 562-740). Thus, if PEG2 PEGylation was specific for position 491, the 43 kD A2 domain should be PEGylated but not the 21 kD C-terminal fragment. This was indeed confirmed by the Western blot for the 22 kD PEGylated PEG2 shown on FIG. 7. Thus, by elimination, PEG2 PEGylation has been localized to the N-terminal 22 kD fragment (FVIII 373-561) of A2 domain. Since PEG-maleimide is completely selective for cysteines at pH 6.8 and the only native FVIII cysteines within 373-561 come from a buried disulfide between 528 and 554, PEG2 is very likely PEGylated on the introduced cysteine at position 491. Western staining of thrombin-treated PEGylated PEG2 with a FVIII heavy chain N-terminal antibody showed no PEGylation of the A1 domain (data not shown). Selective PEGylation of PEG2 using thrombin cleavage method has also been confirmed for PEGs of 5, 12, 33, and 43 kDs (data not shown). Thrombin cleavage of PEGylated wildtype full-length FVIII shows that only B domain is PEGylated (FIG. 8)

Pegylation Analysis by Iodine Staining.

Figure 9:
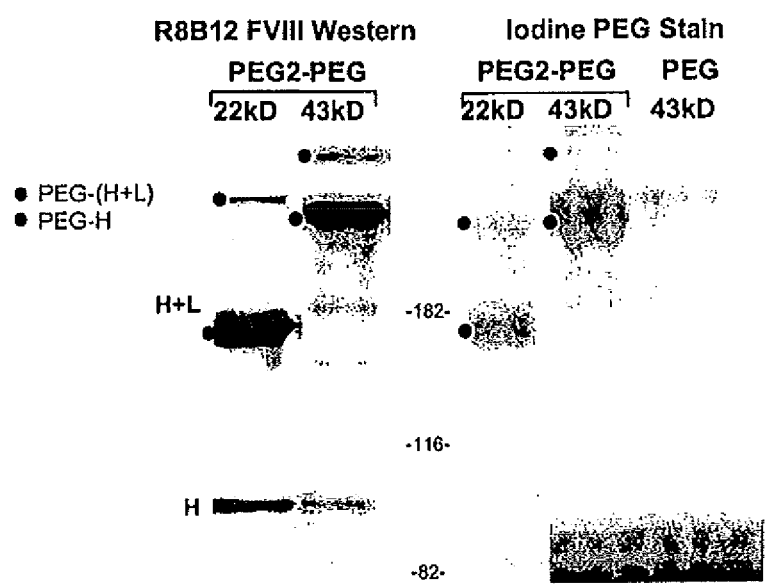
FIG. 9. Iodine Staining of PEGylated PEG2. 22 or 43 kD PEGylated PEG2 was run on a 6% TrisGlycine gel and stained with the R8B12 FVIII antibody (lanes 1 and 2) or iodine (lanes 3 and 4). The two stains were lined up according to their molecular weight marker lanes. Lanes 1 and 2 each contains about 30 ng of FVIII while lanes 3 and 4 contain about 2 µg.

To confirm that the newly created bands on Coomassie Blue and Western staining were indeed PEGylated bands, barium-iodine staining, which is specific for PEG, was used (FIG. 9). PEGylated PEG2 was run on a 6% TrisGlycine gel (Invitrogen) and stained with the R8B12 heavy chain antibody or a barium-iodine solution (Lee et al, Pharm Dev Technol. 1999 4:269-275). The PEGylated bands matched between the two stains using the molecular weight marker to line them up, thus confirming FVIII heavy chain PEGylation.

Pegylation Analysis by MALDI-Mass Spec.

Figure 10A:
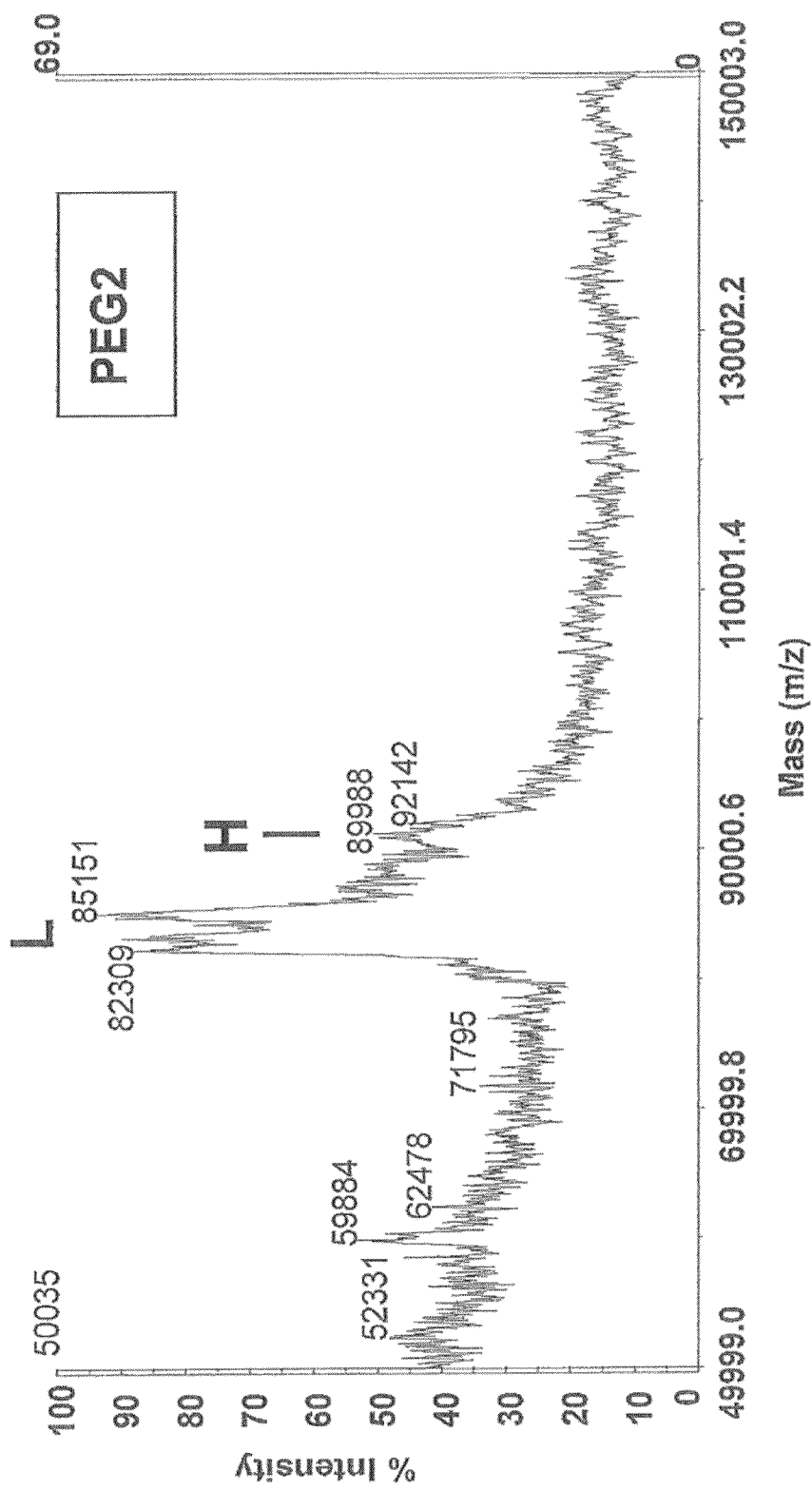
FIG. 10A-10B. MALDI Mass Spectrometry analysis of PEGylated and UnPEGylated PEG2. MALDI Mass Spectrometry was performed on PEG2 (FIG. 10A) or 22 kD PEGylated PEG2 (FIG. 10B). Upon PEGylation, the heavy (H) chain peak of PEG2 is greatly reduced and a new peak (H+PEG), centered at 111 kD (22 kD PEG+89 kD heavy chain), appears. No PEGylated light (L) chain peak, expected to be centered at 100 kD (22 kD PEG+83 kD light chain) is detected.
Figure 10B:
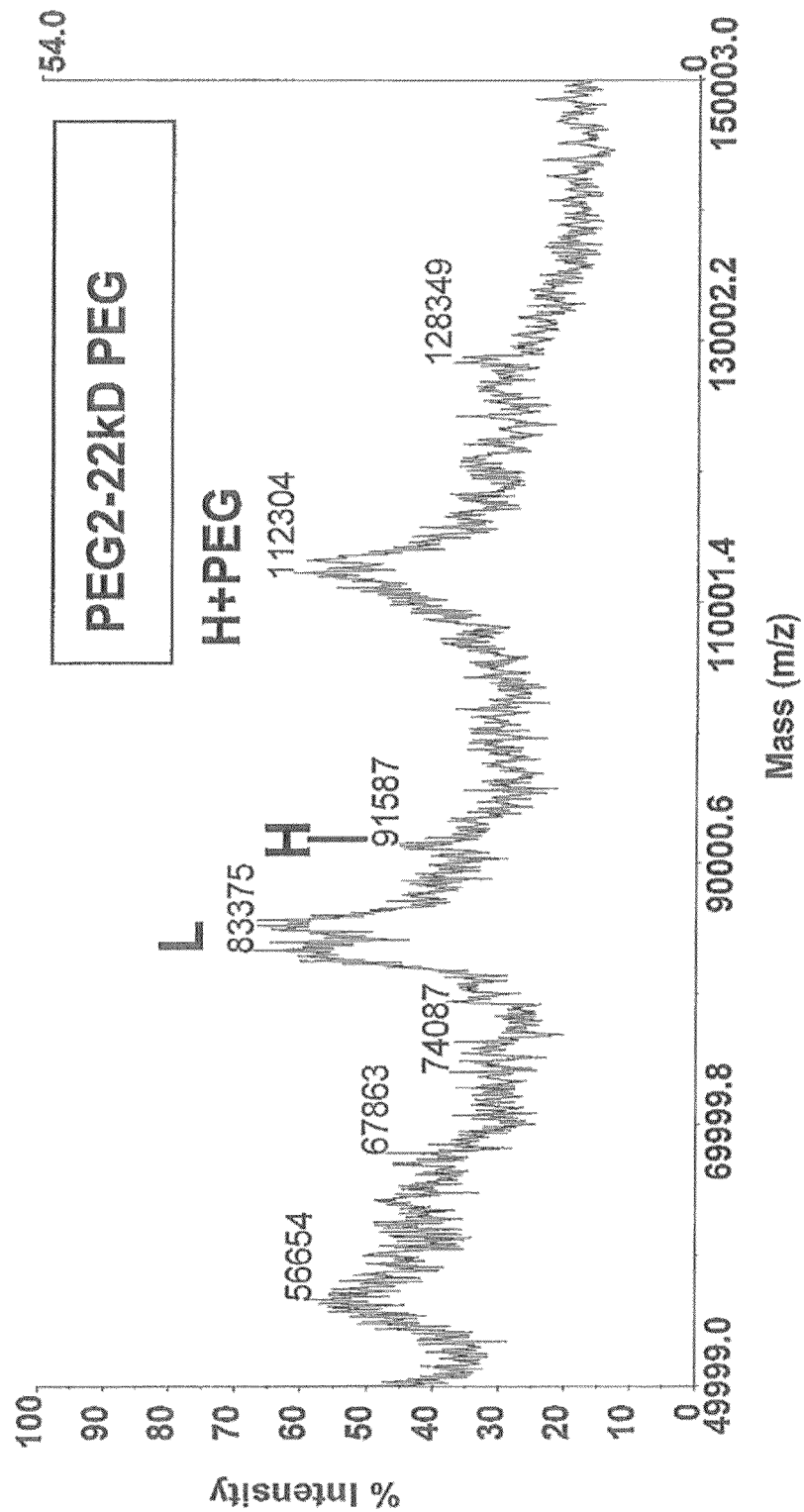

To confirm the PEGylation of the A2 domain in the heavy chain, the rFVIII sample, before and after PEGylation was analyzed by matrix-assisted laser desorption/ionization (MALDI) mass spectrometry. The samples were mixed and crystallized on the MALDI target plate with a sinapinic acid matrix in 30% acetonitrile, 0.1% TFA. They were then analyzed in a Voyager DE-PRO spectrometer in positive, linear mode. The results, shown in FIG. 10, showed the light chain of PEG2 centered at 83 kD and the heavy chain (HC) at 89 kD. The spectrum acquired for the PEGylated sample showed a drop in the HC peak and a new peak, centered at 111 kD, to form. This confirms PEGylation of the heavy chain. No PEGylated light chain (at 105 kD) was observed above detection limit.

Figure 11A:
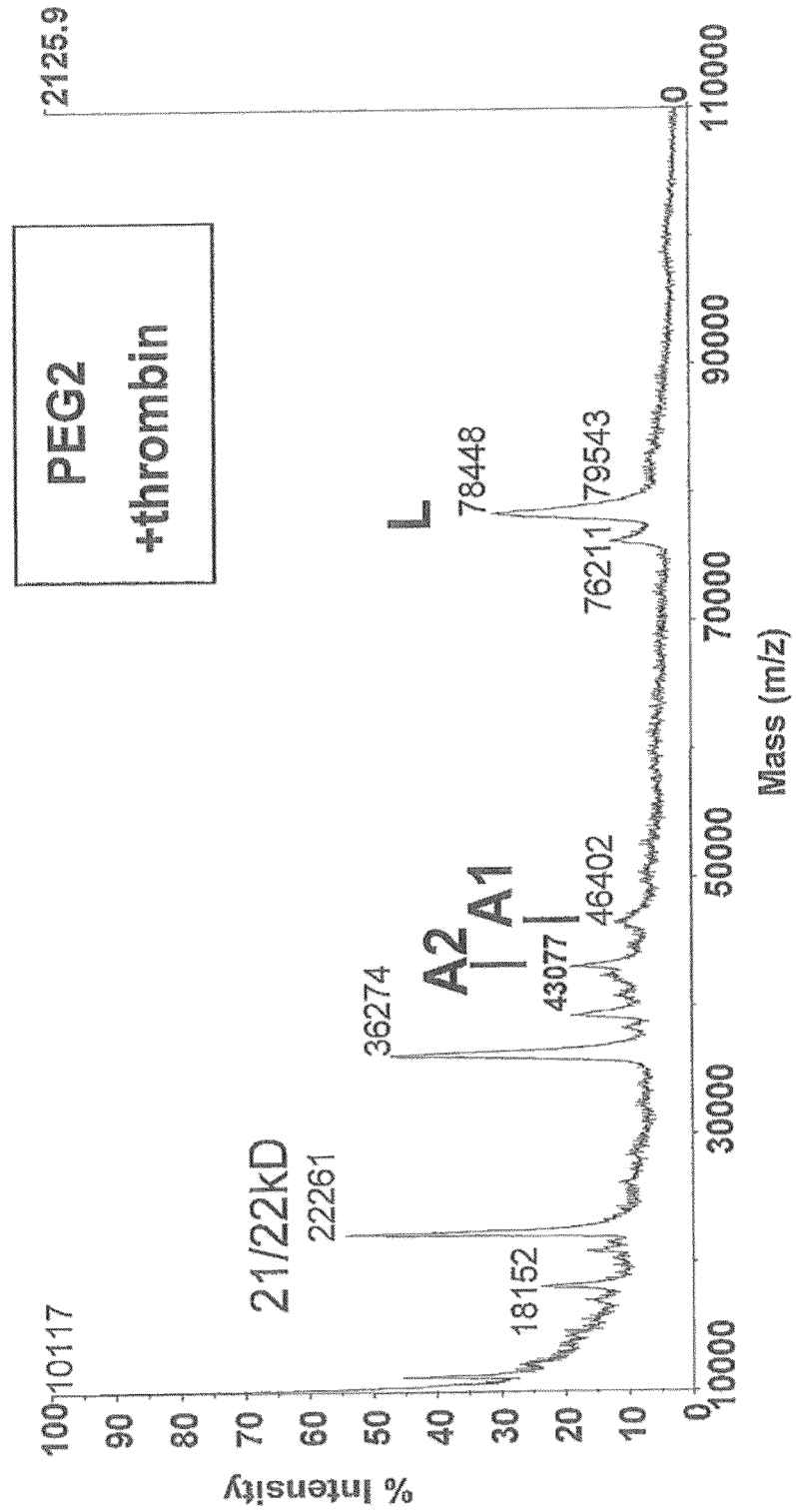
FIG. 11A-11B. MALDI Mass Spectrometry of PEGylated and unPEGylated PEG2 after thrombin cleavage.
Figure 11B:
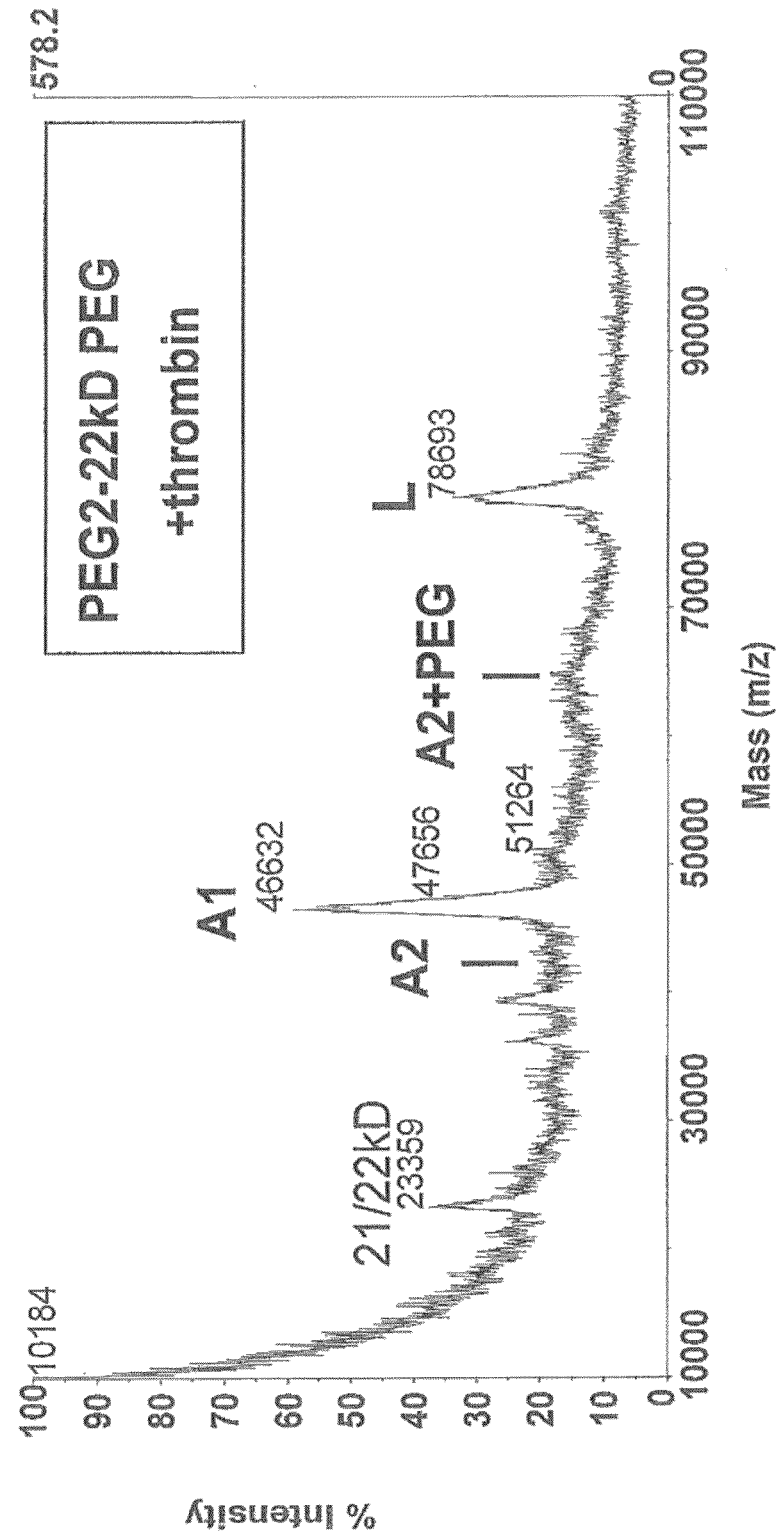
Figure 12A:
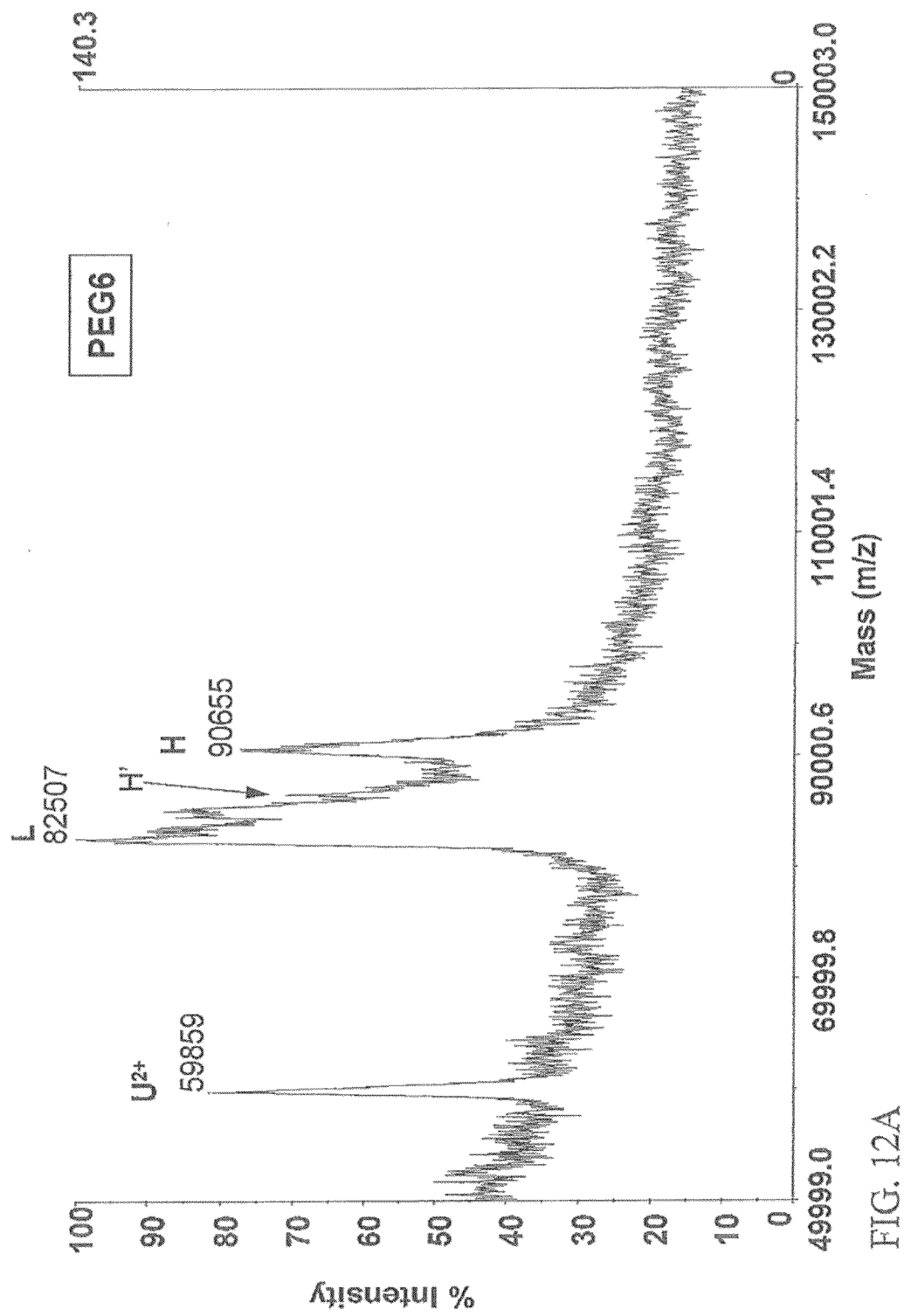
FIG. 12A-12D. MALDI Mass Spectrometry analysis of PEGylated PEG6 before and after thrombin cleavage.
Figure 12B:
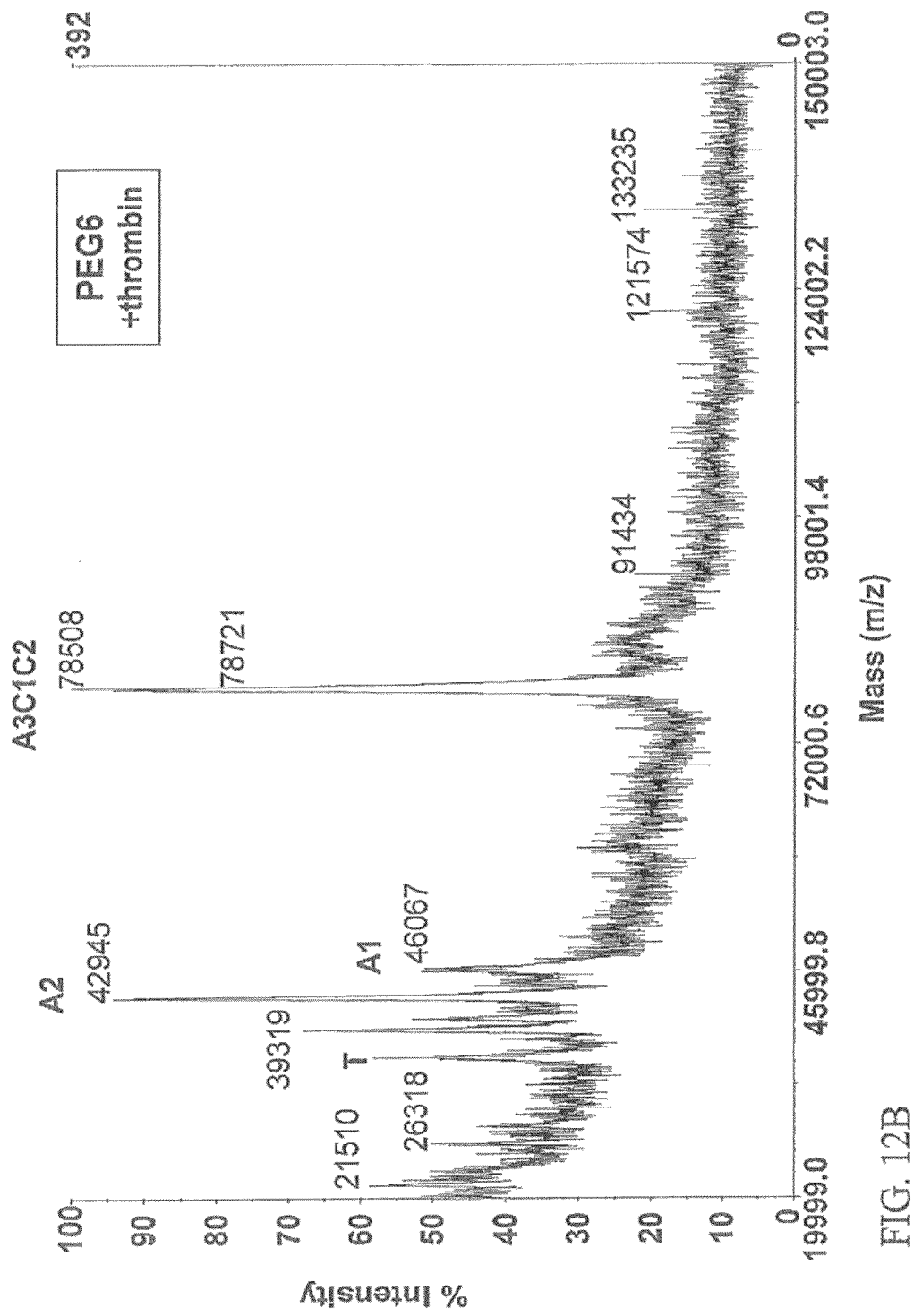
Figure 12C:
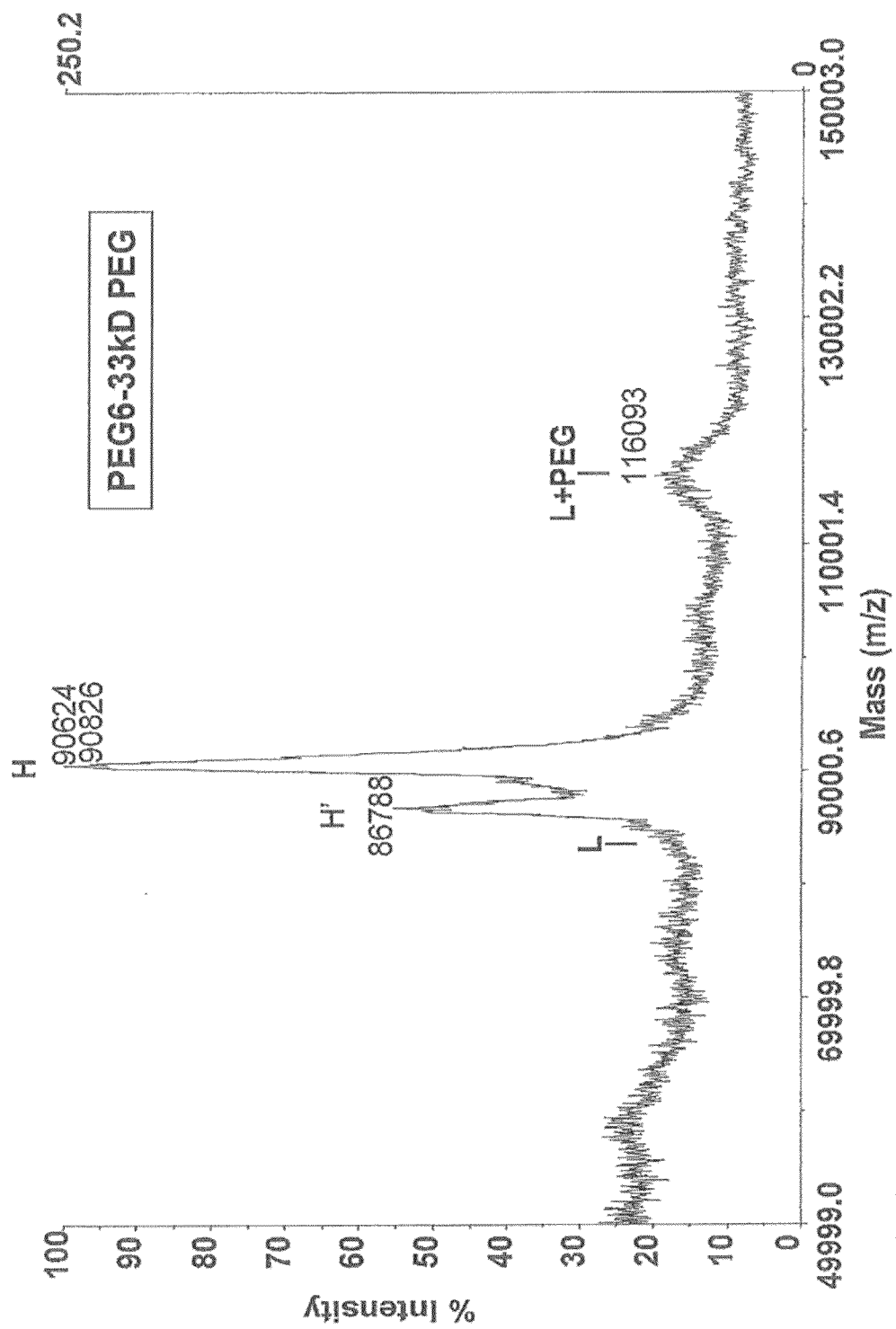
Figure 12D:
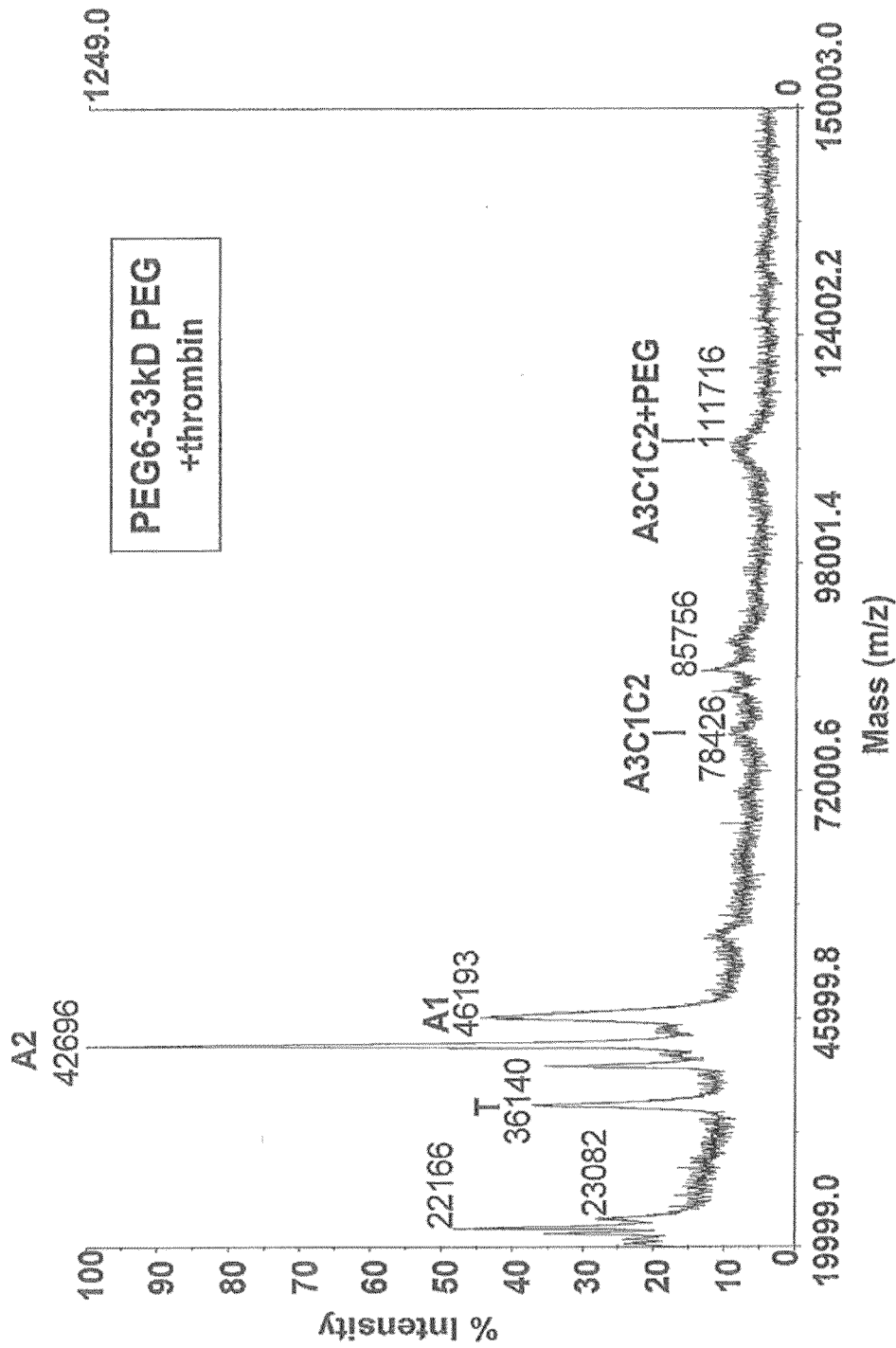

The samples were then both subjected to thrombin digestion at 20 units of thrombin/mg FVIII at 37° C. for 30 minutes, following FVIII concentration determination by amino acid analysis (Commonwealth Biotechnologies, Inc). The heavy chain was cleaved into a 46 kD (A1) N-terminal fraction and a 43 kD (A2) fraction. The MALDI spectrum acquired for the PEGylated sample (FIG. 11) shows the loss of the 43 kD peak and the development of a new 65 kD peak, due to the PEGylated A2 domain. PEGylation of the LC is again not observed above the detection limit. These results again confirm PEGylation of the A2 domain of FVIII. The same analysis was applied to PEGylated PEG6, confirming PEGylation of the light chain A3C1C2 fragment (FIG. 12).

Activity Measurement

Coagulation Assay.

The clotting FVIII:C test method is a one-stage assay based upon the activated partial thromboplastin time (aPTT). FVIII acts as a cofactor in the presence of Factor IXa, calcium, and phospholipid in the enzymatic conversion of Factor X to Xa. In this assay, the diluted test samples are incubated at 37° C. with a mixture of FVIII deficient plasma substrate and aPTT reagent. Calcium chloride is added to the incubated mixture and clotting is initiated. An inverse relationship exists between the time (seconds) it takes for a clot to form and logarithm of the concentration of FVIII:C. Activity levels for unknown samples are interpolated by comparing the clotting times of various dilutions of test material with a curve constructed from a series of dilutions of standard material of known activity and are reported in International Units per mL (IU/mL).

Chromogenic Assay.

The chromogenic assay method consists of two consecutive steps where the intensity of color is proportional to the FVIII activity. In the first step, Factor X is activated to FXa by FIXa with its cofactor, FVIIIa, in the presence of optimal amounts of calcium ions and phospholipids. Excess amounts of Factor X are present such that the rate of activation of Factor X is solely dependent on the amount of FVIII. In the second step, Factor Xa hydrolyzes the chromogenic substrate to yield a chromophore and the color intensity is read photometrically at 405 nm. Potency of an unknown is calculated and the validity of the assay is checked with the slope-ratio statistical method. Activity is reported in International Units per mL (IU/mL).

The 1811-1818 loop is involved in binding to FIX, but the importance of individual positions within this loop has not been determined. PEG7-10 muteins display nearly identical specific chromogenic activity relative to native FVIII (Table 3). Table 3 shows the percent specific activity (S.A.) of PEG muteins and PEGylated PEG2 or PEG6 relative to BDD. S.A. was determined by dividing the chromogenic, coagulation, or vWF binding activity by the total antigen ELISA (TAE) value. The S.A. of PEGylated muteins was then divided by the S.A. of BDD (8 IU/ug chromogenic, 5 IU/ug coagulation, and 1 vWF/TAE) and multiplied by 100 to obtain the percent S.A. listed in Table 3 under the headings chromogenic, coagulation and vWF/TAE.

TABLE 3

Percent specific activity (S.A.) of PEG muteins and PEGylated PEG2 and PEG6 relative to BDD.

| | Mutation | Chromogenic | Coagulation | vWF/TAE |
|---|---|---|---|---|
| BDD | | 100 | 100 | 100 |
| PEG1 | Y487C | | | |
| PEG2 | L491C | 125 | 130 | 138 |
| PEG2 red | L491C | 137 | 141 | 98 |
| PEG2-5 kD PEG | L491C | 124 | 93 | 125 |
| PEG2-12 kD PEG | L491C | 118 | 25 | 71 |
| PEG2-22 kD PEG | L491C | 103 | 13 | 87 |
| PEG2-33 kD PEG | L491C | 130 | 17 | 59 |
| PEG2-43 kD PEG | L491C | 91 | 9 | 57 |
| PEG3 | K496C | | | |
| PEG4 | L504C | | | |
| PEG5 | Q468C | 92 | | |
| PEG6 | K1808C | 83 | 60 | 100 |
| PEG6-33 kD PEG | K1808C | 42 | 6 | 90 |
| PEG7 | N1810C | 100 | | |
| PEG8 | T1812C | 100 | | |
| PEG9 | K1813C | 83 | | |
| PEG10 | Y1815C | 75 | | |
| PEG11 | D1795C | | | |
| PEG12 | Q1796C | | | |
| PEG13 | R1803C | | | |
| PEG14 | K1804C | | | |
| PEG2 + 6 | 491C/1808C | | | |
| PEG15 | K377C | 82 | | |
| PEG16 | H378C | 126 | | |
| PEG17 | K556C | 43 | | |
| PEG18 | N41C | 80 | | |
| PEG19 | N239C | | | |
| PEG20 | N2118C | 127 | | |
| PEG21 | Y81C | | | |
| PEG22 | F129C | 83 | | |
| PEG23 | K422C | | | |
| PEG24 | K523C | | | |
| PEG25 | K570C | | | |
| PEG26 | N1864C | | | |
| PEG27 | T1911C | | | |
| PEG28 | Q2091C | | | |
| PEG29 | Q2284C | | | | increases beyond 5 kD. There may be a modest reduction in vWF binding for larger size PEGylated PEG2 also.

Total Antigen ELISA (TAE).

FVIII is captured on a microtiter plate that has been coated with a polyclonal FVIII antibody. The FVIII bound is detected with a biotinylated polyclonal rFVIII antibody and streptavidin horseradish peroxidase (HRP) conjugate. The peroxidase-streptavidin complex produces a color reaction upon addition of the tetramethylbenzidine (TMB) substrate. Sample concentrations are interpolated from a standard curve using four parameter fit models. FVIII results are reported in µg/mL.

vWF Binding Elisa.

FVIII is allowed to bind to vWf in Severe Hemophilic Plasma in solution. The FVIII-vWf complex is then captured on a microtiter plate that has been coated with a vWf-specific monoclonal antibody. The FVIII bound to the vWf is detected with a FVIII polyclonal antibody and a horseradish peroxidase-anti-rabbit conjugate. The peroxidase-conjugated antibody complex produces a color reaction upon addition of the substrate. Sample concentrations are interpolated from a standard curve using four parameter fit model. FVIII binding results are reported in µg/mL. There was no significant impact on any of the activities upon PEGylation, which would be consistent with PEGylation at the B domain.

TABLE 4

Specific activity (S.A.) of wildtype full length FVIII (KG-2) before and after PEGylation with different sizes of PEG.

| | TAE | Coagulation Assay | | | Chromogenic Assay | | | vWF ELISA | | |
|---|---|---|---|---|---|---|---|---|---|---|
| Sample | ug/mL | IU/mL | IU/ug | % Start | IU/mL | IU/ug | % Start | ug/mL | vWF/TAE | % Start |
| KG-2 start | 1.31 | 4.8 | 3.6 | 100 | 5.60 | 4.3 | 100 | 0.42 | 0.32 | 100 |
| Reduced only | 0.93 | 3.1 | 3.4 | 93 | 4.08 | 4.4 | 103 | | | |
| KG-2-5 kD PEG | 0.71 | 2.5 | 3.5 | 96 | 3.09 | 4.3 | 102 | | | |
| KG-2-12 kD PEG | 0.59 | 2.3 | 3.9 | 107 | 2.99 | 5.0 | 118 | | | |
| KG-2-22 kD PEG | 0.63 | 2.5 | 3.9 | 108 | 3.06 | 4.8 | 113 | 0.19 | 0.30 | 94 |
| KG-2-30 kD PEG | 0.59 | 2.5 | 4.1 | 114 | 3.01 | 5.1 | 119 | 0.19 | 0.32 | 100 |
| KG-2-43 kD PEG | 0.52 | 2.4 | 4.6 | 128 | 2.86 | 5.5 | 129 | | | |

As used in Table 3, "PEG2 red" is PEG2 mutein that has been treated with reductant followed by the removal of reductant. This reduction procedure did not significantly alter the three functional activities of FVIII. PEG2 mutein conjugated to PEGs ranging from 5 kD (PEG2-5 kD) to 43 kD (PEG2-43 kD) did not lose a significant amount of chromogenic activity, but had greatly lower coagulation activity as the PEG size Purification of Pegylated FVIII by Ion-Exchange Chromatography.

PEGylated FVIII is applied to an anion exchange column or cation exchange column where the protein binds to the column while any excess free PEG reagent does not bind and is removed in the flow through. The PEG mutein is then eluted from the column with a sodium chloride gradient. A barium-iodine stained 4-12% Bis-Tris gel of load, flow through, and gradient fractions was used to confirm that the column elution fractions have PEGylated mutein.

Purification of Pegylated FVIII by Size-Exclusion Chromatography.

Figure 13:
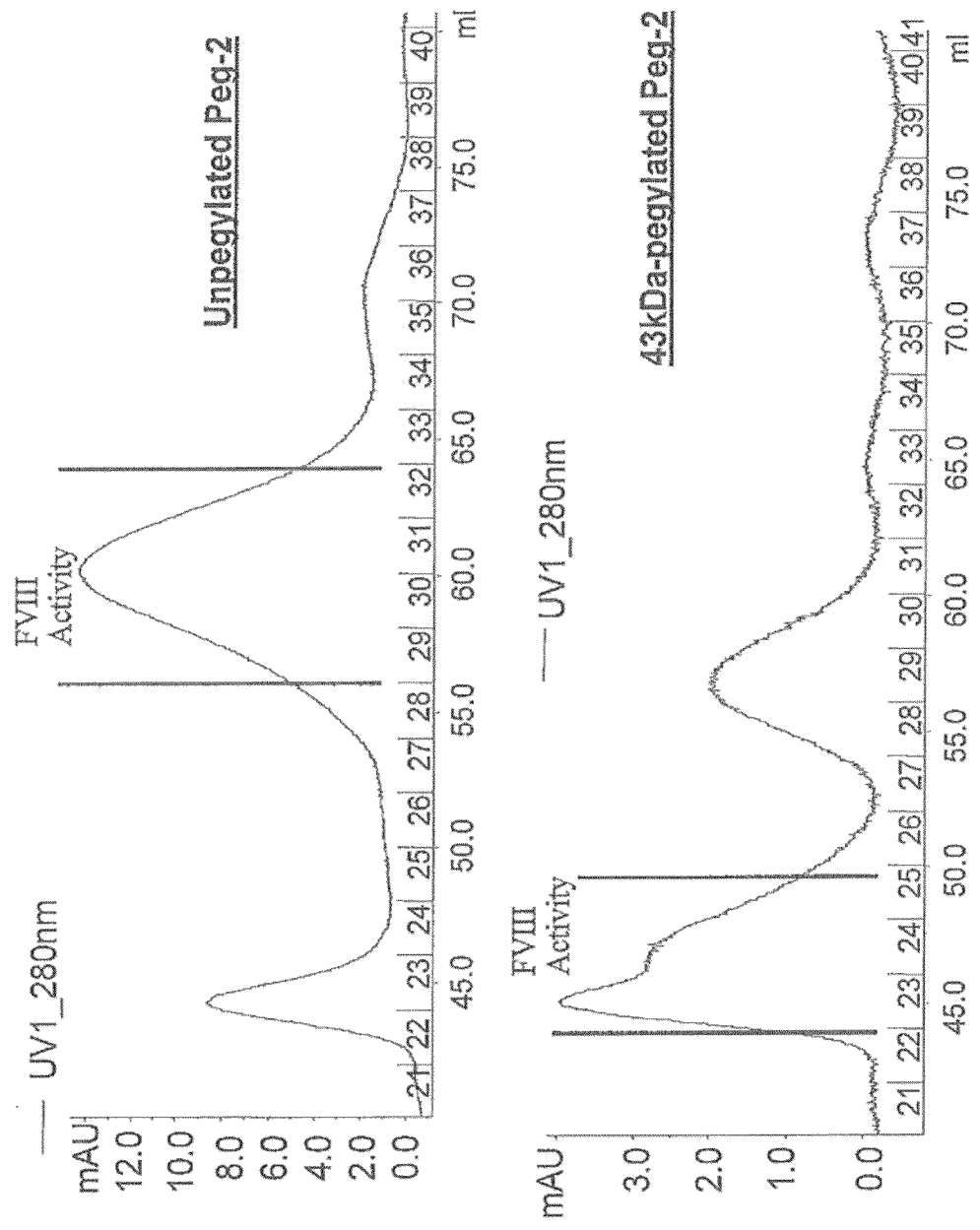
FIG. 13. The UV absorption profile at 280 nm of PEGylated PEG2 purified on size-exclusion column.

The anion exchange fractions containing the majority of PEG2 mutein are pooled and concentrated by ultrafiltration then applied to a size exclusion column. The column is then eluted using the formulation buffer. Because of the difference in the size and shape of the protein depends on whether PEG is bound to the protein, this column separates the PEGylated PEG2 mutein from that of any remaining PEG2, which is not PEGylated. The PEGylated mutein FVIII fractions are pooled based on having the most FVIII activity then frozen for subsequent animal studies and molecular characterization. FIG. 13 compares the elution of non-PEGylated PEG2 mutein versus that of the 43 kD PEGylated PEG2 mutein. The PEGylated PEG2 elutes significantly earlier, which indicates an increase in its size and shape from the covalently attached PEG.

Figure 14:
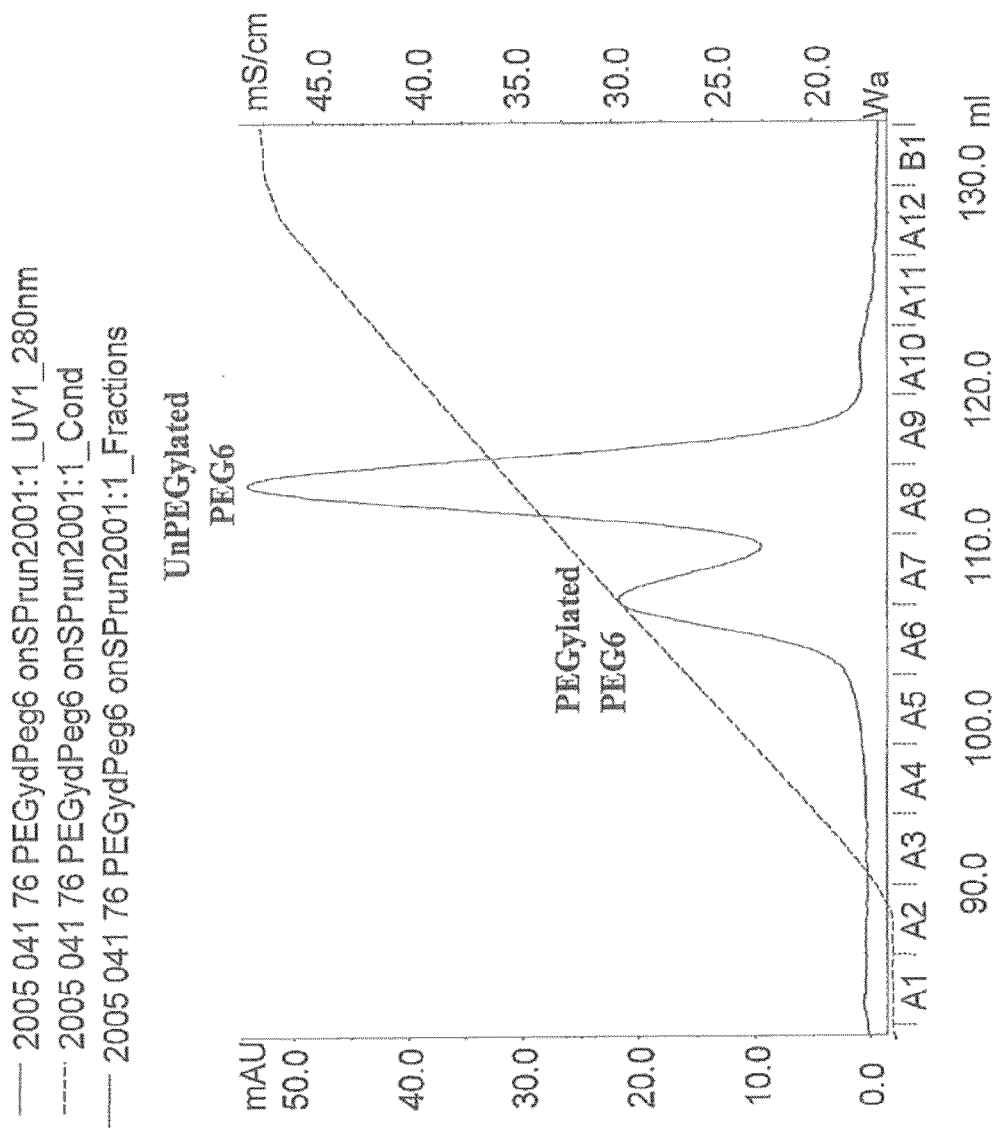
FIG. 14. The UV absorption profile at 280 nm of PEGylated and UnPEGylated PEG6 purified on cation exchange column.
Figure 15:
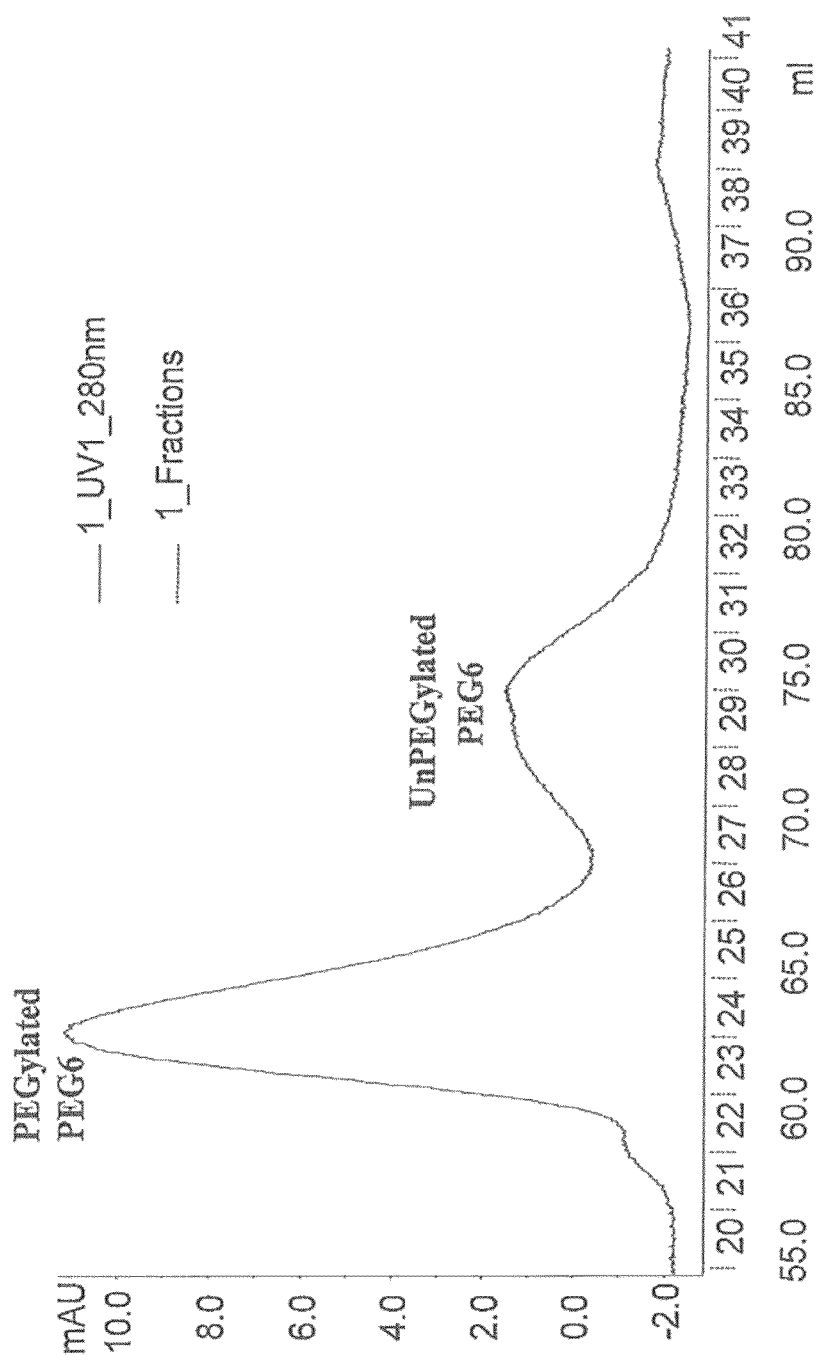
FIG. 15. The UV absorption profile at 280 nm of PEGylated and UnPEGylated PEG6 purified on size-exclusion column.

With muteins such as PEG6 that show lower efficiencies of PEGylation, i.e. less than 50%, the most effective purification scheme to yield highly pure mono-PEGylated product is to use a combination of cation exchange chromatography followed by size exclusion chromatography. For example, with PEG6, the cation exchange chromatography purifies the PEGylated PEG6 (earlier eluting fraction, FIG. 14) away from the majority of un-PEGylated PEG6 (later eluting fraction, FIG. 15). The size exclusion chromatography then polishes the PEGylated protein (earlier eluting fraction, FIG. 15) from the remainder of un-PEGylated protein (later eluting fraction FIG. 15).

Effect of Peg Size on Activity.

To test whether PEG sizes have an effect on both coagulation and chromogenic activities of FVIII upon PEGylation, purified full-length FVIII, PEG2, PEG6, and PEG14 were reduced by TCEP followed by reductant removal and reaction with a buffer control or PEGs ranging from 6 kD to 64 kD. The resulting PEGylated FVIII was directly assayed without removal of excess PEG or unPEGylated FVIII. Control experiments showed that the excess PEG has no effect on FVIII activity.

Figure 16:
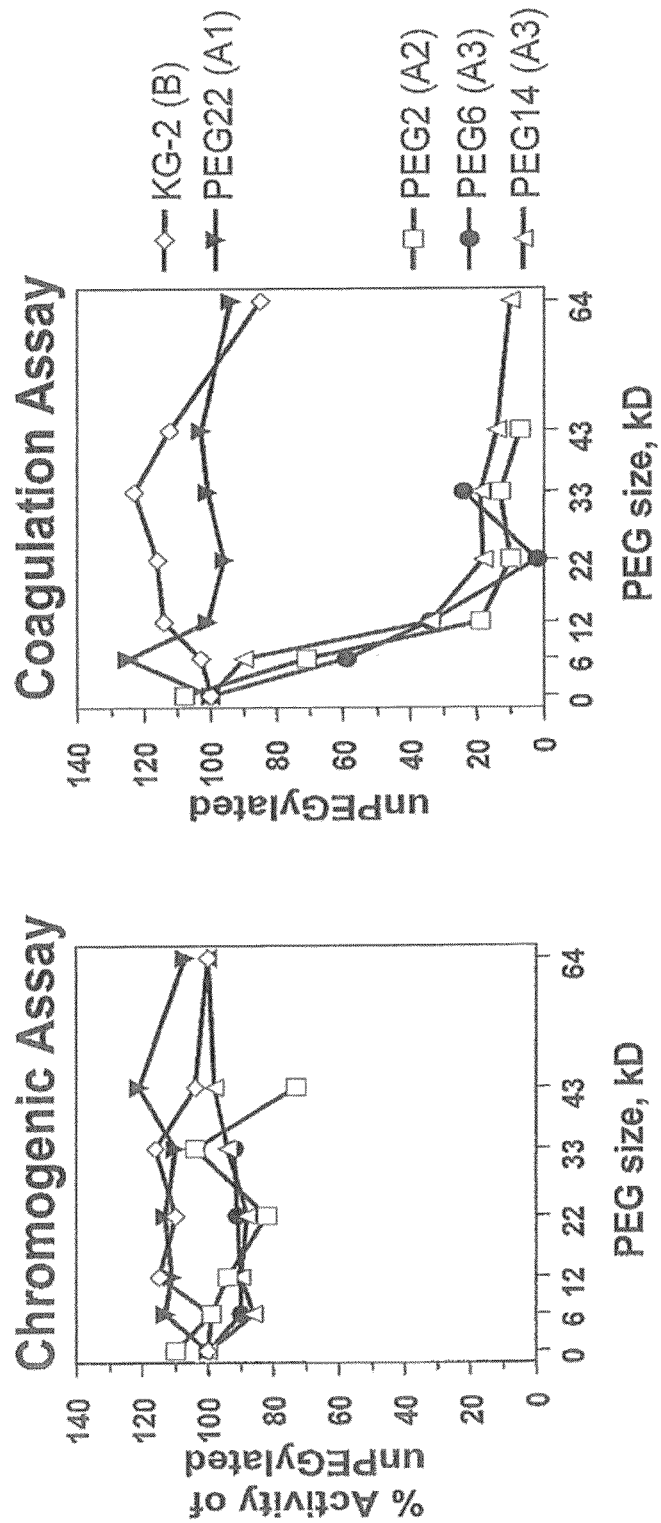
FIG. 16. Activity of PEGylated protein is compared to activity of the unPEGylated protein as measured by a chromogenic assay and a coagulation assay. Purified full-length FVIII is represented as KG-2. The percent activity reported was determined by dividing the value of sample treated with PEG after reduction and reductant removal by that of the sample treated with buffer control taking into consideration the PEGylation yield.

FIG. 16 shows the results of this study. Purified full-length FVIII is represented as KG-2 in FIG. 16. The percent activity reported in FIG. 16 was determined by dividing the value of sample treated with PEG after reduction and reductant removal by that of the sample treated with buffer control taking into consideration the PEGylation yield. PEGylation yields were comparable across all PEGs for any given FVIII construct. They are about 80% for KG-2, PEG2, and PEG14 and about 40% for PEG6. For example, PEG14 buffer control treated has a coagulation activity of 6.8 IU/mL vs. 3.2 IU/mL for the 12 kD PEGylated PEG14 sample. However, the PEGylation efficiency was about 80%, meaning the 3.2 IU/mL represents the aggregate activity of about 80% PEGylated and about 20% unPEGylated. Assuming the unPEGylated sample has the same activity as the buffer control treated PEG14, the percent activity of unPEGylated for the PEGylated PEG14 works out to be 34%=(3.2-6.8 times 20%)/(6.8 times 80%).

PEGylation within the A2 or A3 domain at PEG2, PEG6, or PEG14 position of BDD led to dramatic losses of coagulation activity when PEG size increases beyond 6 kD. However, PEGylation within the B domain at a native B-domain cysteine of the full-length FVIII had no effect on the coagulation activity. Interestingly, the chromogenic activity is not affected for all PEGylated constructs. This may be due to assay differences. It is possible that the small chromogenic peptide substrate has an easier access to a PEGylated FVIII/FIX/FX complex than the larger protein substrate used in the coagulation assay. Alternatively, PEG may affect activation of the mutein. This would be more readily detected by the one-stage coagulation assay than the two-stage chromogenic assay.

To confirm the observation of PEG effects on the coagulation activity of PEG2, 6, and 14, several PEGylated contructs were purified away from excess PEG and unPEGylated. Since PEG does not have any effect on the chromogenic activity, the chromogenic to coagulation activity ratio is a good estimate on the relative effect of PEG on coagulation activity (Table 5). Larger PEGs at a given position such as PEG2 and a higher number of PEGs as in the case with the PEG2+6 construct induce a greater loss of coagulation activity.

TABLE 5

Ratio of Chromogenic to Coagulation for Purified PEGylated BDD.

| PEGylated BDD | | Chromogenic IU/mL/Coagulation IU/mL | |
|---|---|---|---|
| Sample ID | PEG | Raw Ratio | Ratio relative to BDD |
| BDD | no PEG | 1.7 | 1 |
| PEG2 (pool2) | 22 kD 491 | 9 | 5 |
| PEG2 | 43 kD* 491 | 25 | 15 |
| PEG6 | 12 kD 1808 | 5 | 3 |
| PEG6 (old) | 33 kD 1808 | 13 | 7 |
| PEG6 (new) | 33 kD 1808 | 8 | 5 |
| PEG2 + 6 (LSP25) | 33 kD at 491, Mono | 10 | 6 |
| PEG2 + 6 (LSP22) | 33 kD at 491/1808, Di | 24 | 14 |
| PEG2 + 6 (ESP) | 33 kD at 491/1808/A3, Tri | 60 | 35 |
| PEG22 | 64 kD* 129 | 14 | 8 |
| PEG14 | 12 kD 1804 | 3.2 | 1.9 |
| PEG14 | 20 kD* 1804 | 4.2 | 2.5 |
| PEG14 | 33 kD 1804 | 5 | 2.9 |
| PEG2 + 14 (ESP19) | 33 kD at 491/1804, Di | 21 | 12 |

*branched PEG

Rabbit PK Study.

Figure 17:
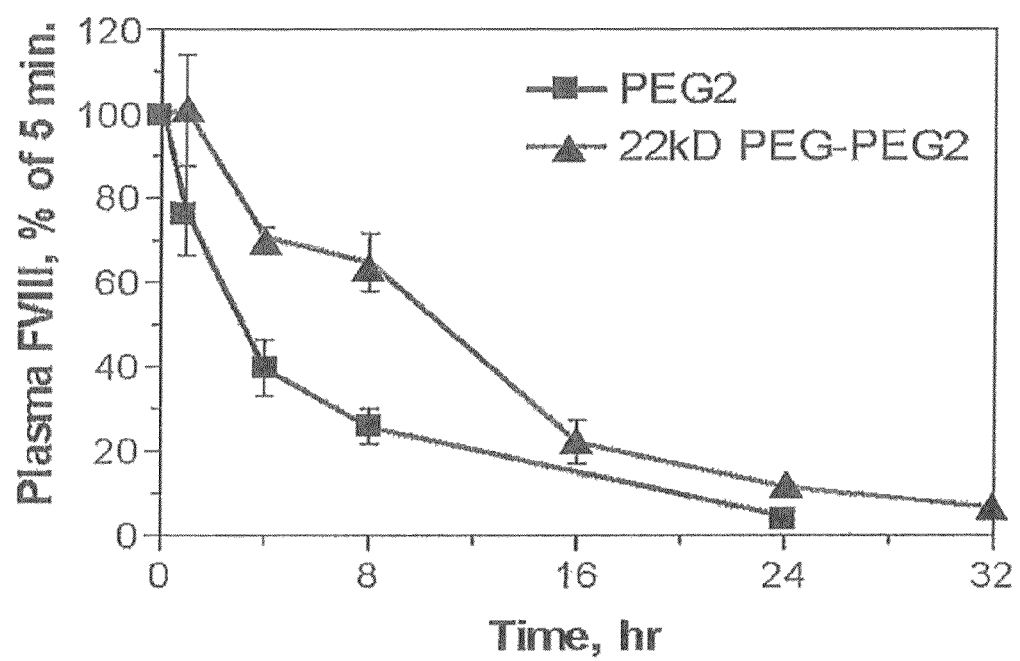
FIG. 17. Rabbit PK study of PEGylated PEG2 compared to PEG2.
Figure 18:
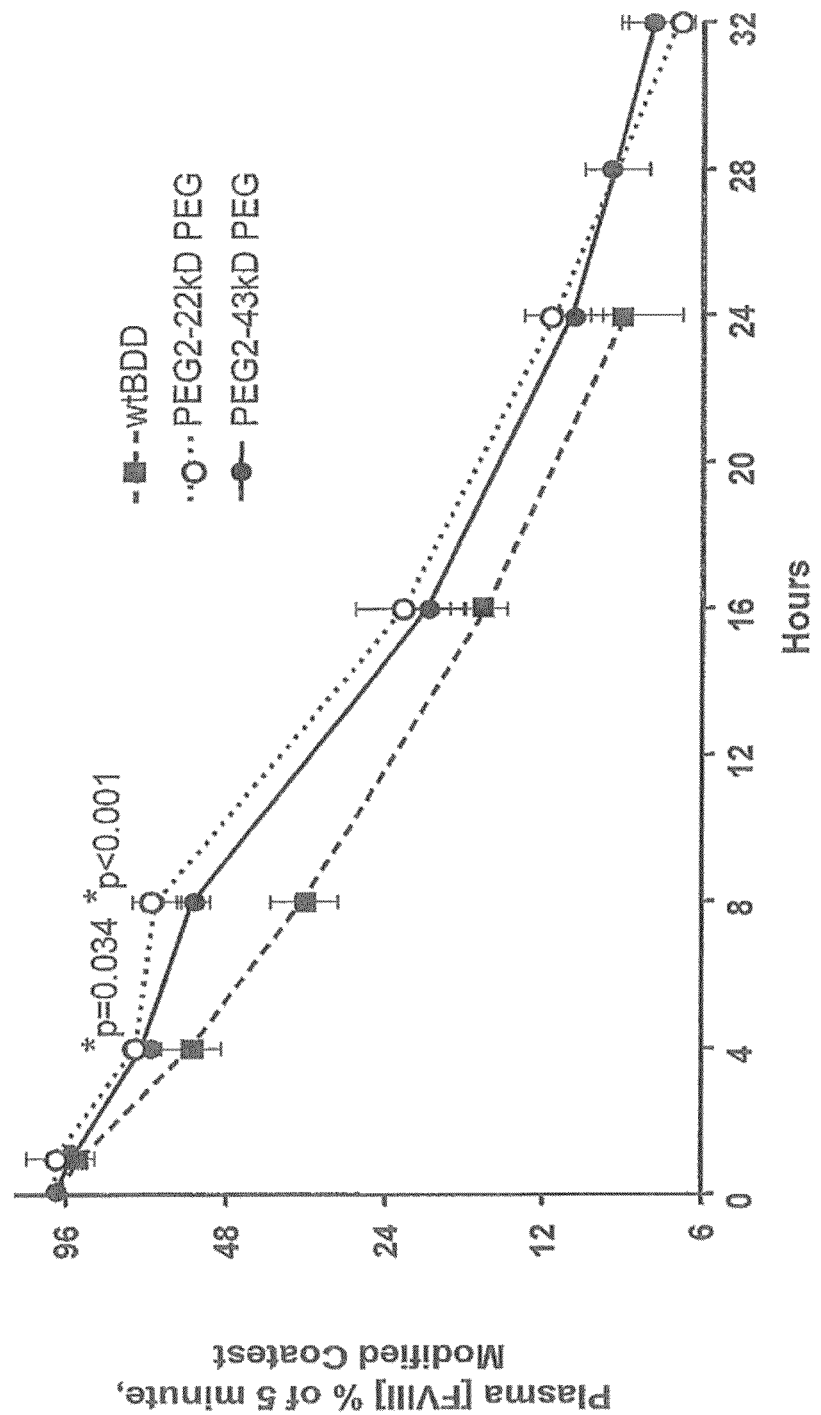
FIG. 18. Rabbit PK study of PEGylated PEG2 compared to BDD and PEG2. P-values are comparisons between PEGylated PEG2 and BDD.
Figure 19:
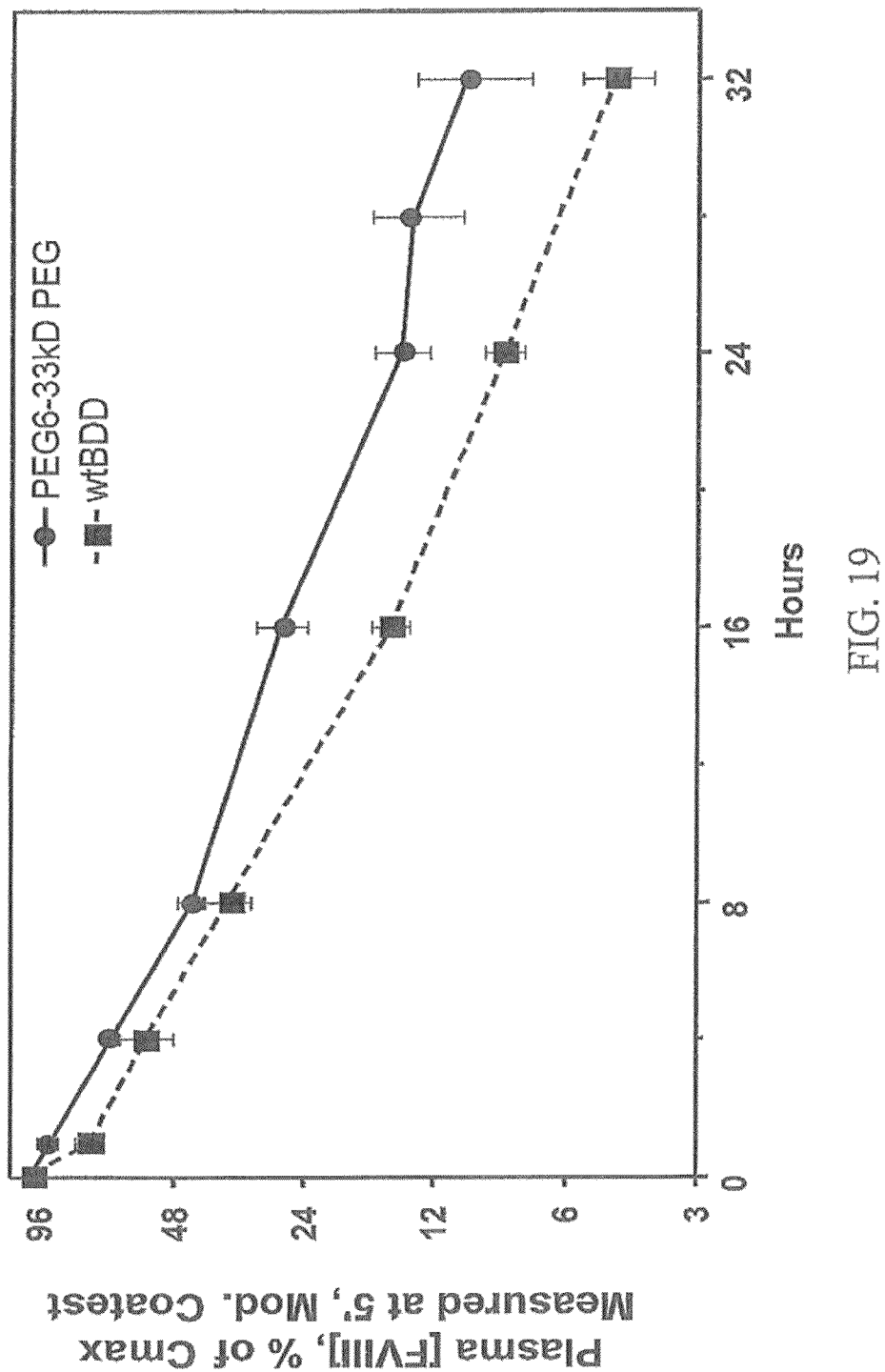
FIG. 19. Rabbit PK study of PEGylated PEG6 compared to BDD and PEG6.
Figure 20:
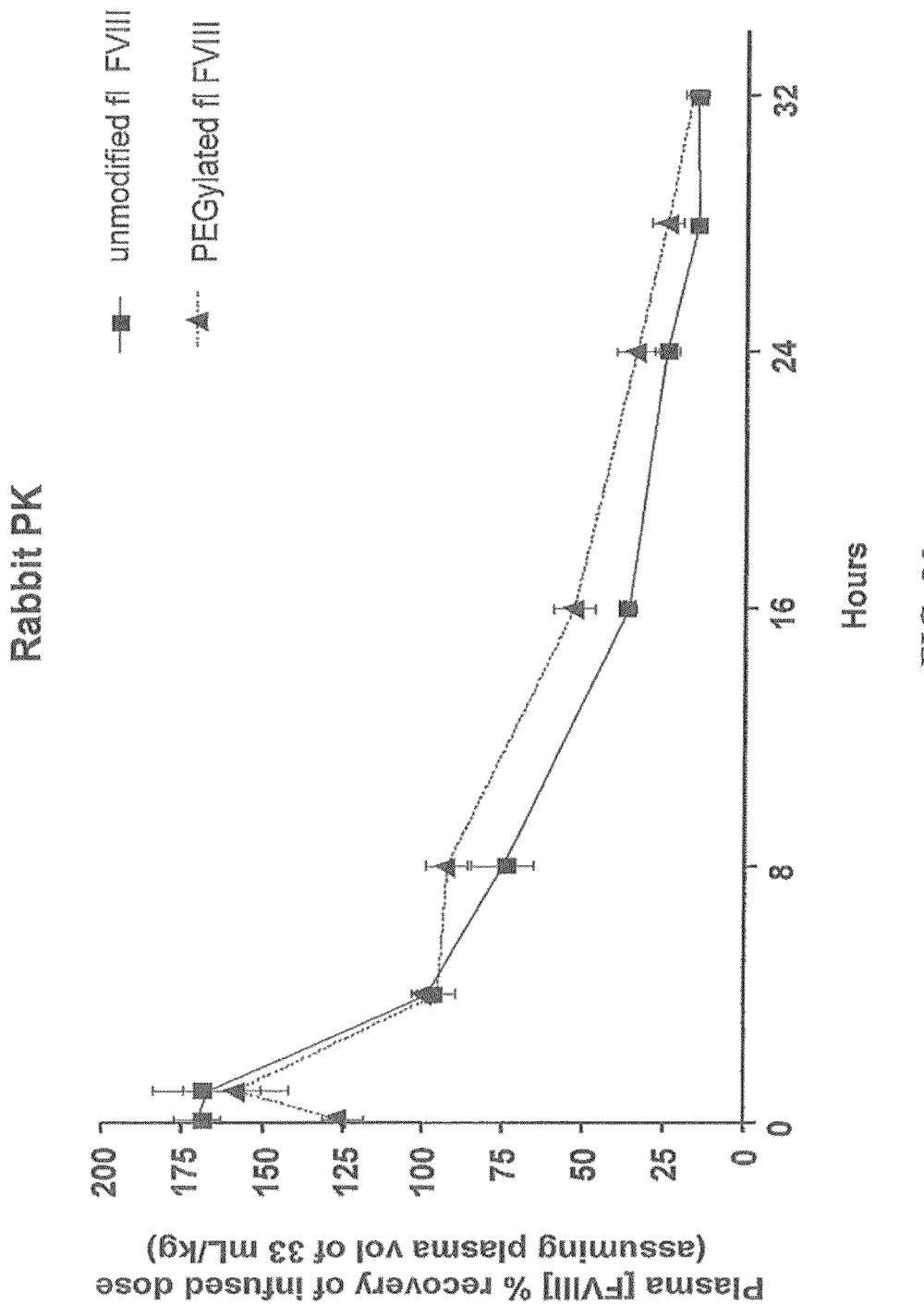
FIG. 20. Rabbit PK study of PEGylated wildtype full-length ("fl") FVIII compared to unmodified fl FVIII.

To understand the effects of PEGylation on the pharmacokinetics (PK) of FVIII, PK studies were performed in a number of species. NZW SPF rabbits were used for the study: 10 females, 5 rabbits per group, 2 groups (PEG2 FVIII and 22 kD PEGylated PEG2). Samples were diluted into sterile PBS with a final concentration of 100 IU/mL (chromogenic units). Each rabbit received a dose of 1 ml/kg (100 IU/kg) of the diluted test or control substance via marginal ear vein. At various times post-injection, blood samples (1 mL) were drawn into a 1 mL syringe (charged with 100 µL of 3.8% Na-Citrate) from the central ear artery at defined time points after dosing. Plasma samples were incubated with R8B12 heavy chain antibody coated on a 96-well plate to specifically capture the dosed human FVIII. The activity of the captured FVIII was determined by the chromogenic assay (FIG. 17). PEGylated PEG2 and PEGylated PEG6 were also compared with BDD (FIGS. 18 and 19), with PEGylated muteins showing an improvement in plasma recovery compared to BDD. PEGylated wildtype full-length FVIII did not appear to show much improvement (FIG. 20).

Mouse PK Study.

Figure 21:
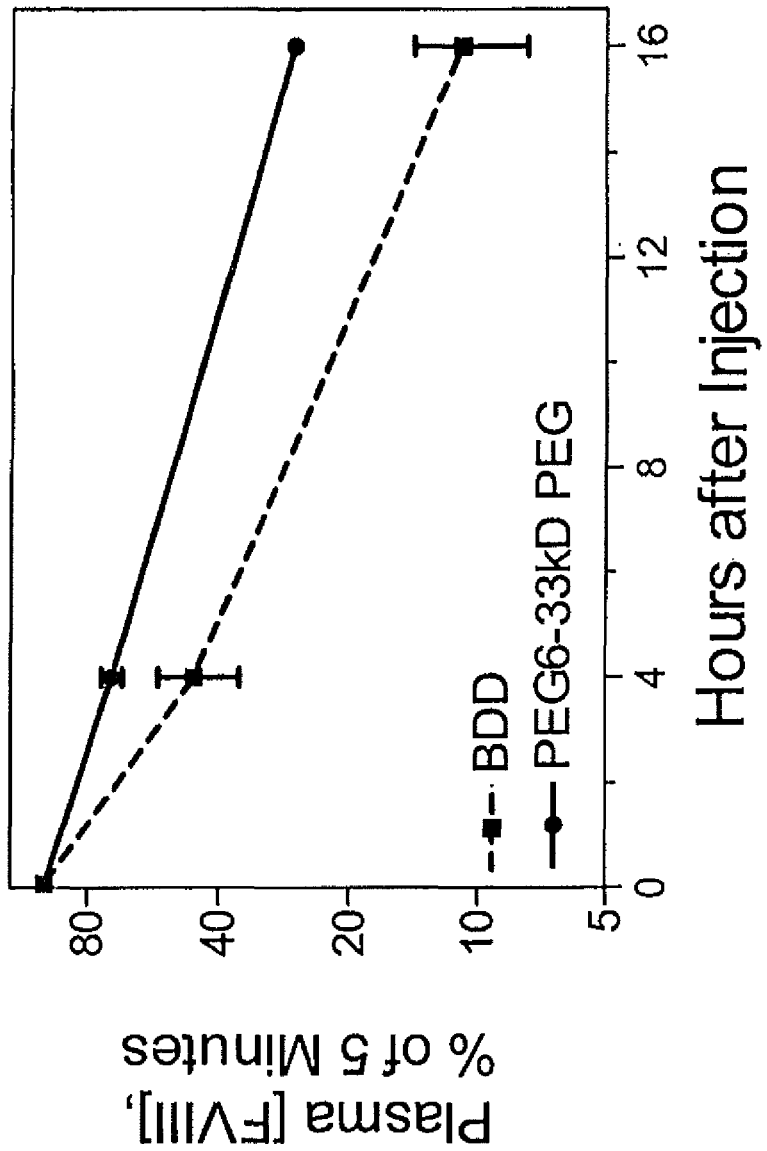
FIG. 21. Hemophilic mouse PK study of PEGylated PEG6 compared to PEG6 and BDD.
Figure 22:
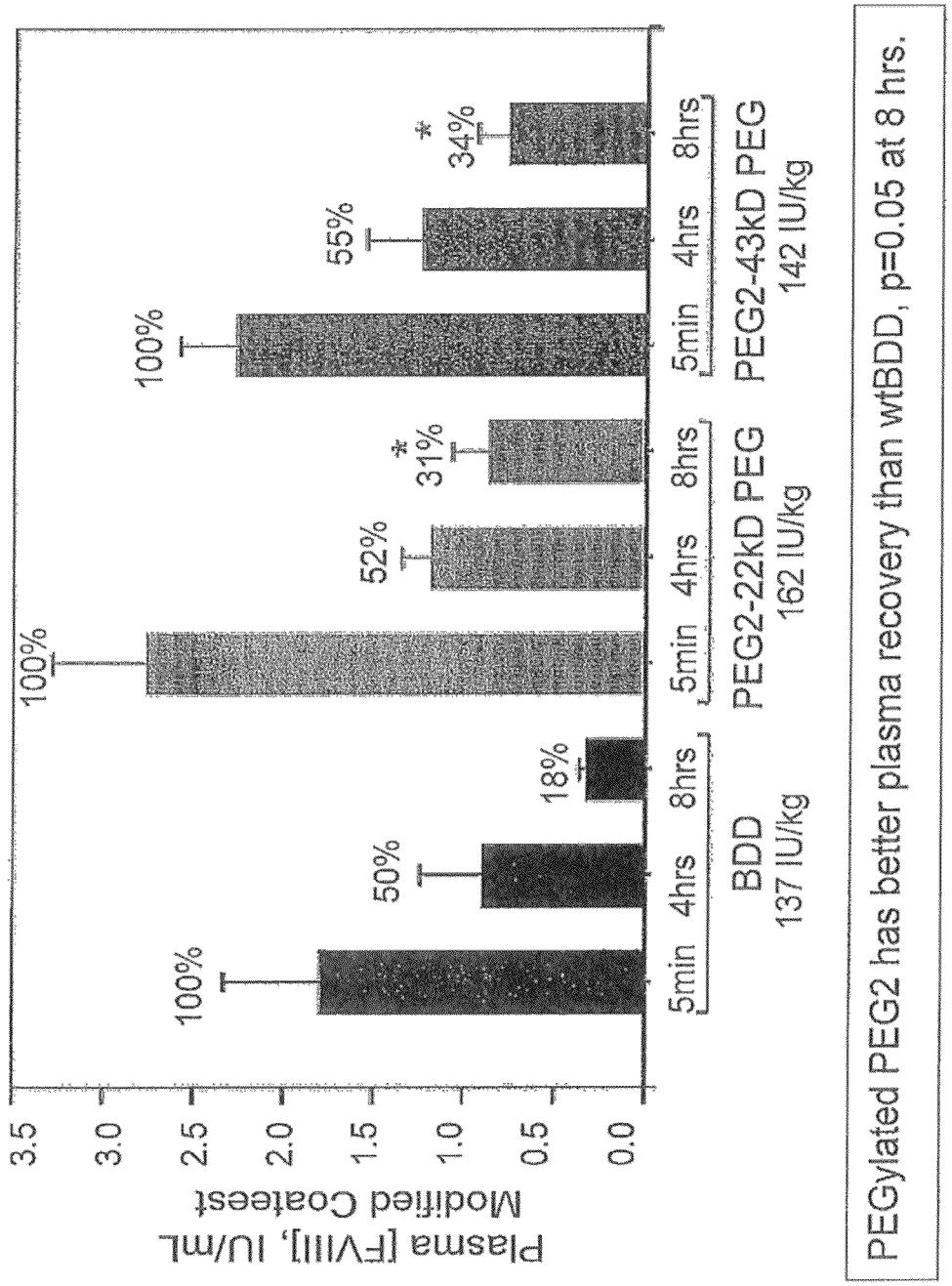
FIG. 22. Normal mouse PK study of 22 and 43 kD PEGylated PEG2 compared to BDD.
Figure 23:
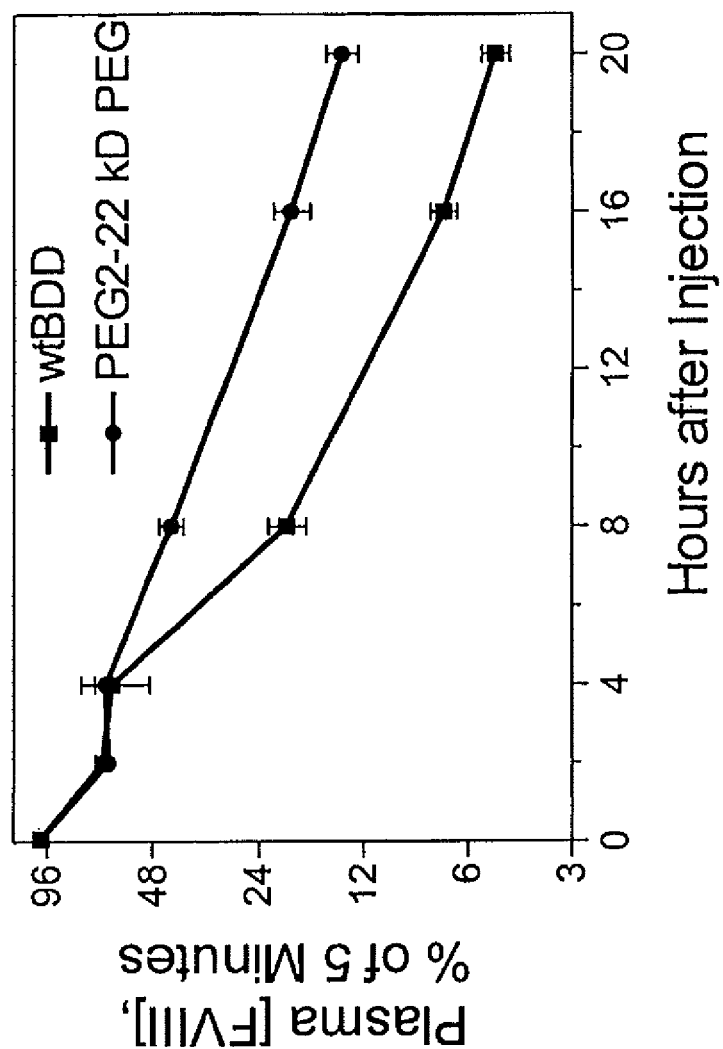
FIG. 23. Normal mouse PK study of 22 kD PEGylated PEG2 compared to BDD, full time course.

As a second species, ICR normal or hemophilic, FVIII deficient, mice (Taconic, Hudson, N.Y.) were used in PK studies. Normal mice were used for the study, 5 mice per group per time point. Test materials were diluted into formulation buffer to a nominal final concentration of 25 IU/mL. Each mouse can be administered 4 mL/kg (~0.1 mL total volume) of the dilute test material via tail vein. Blood samples (0.45 or 0.3 mL for normal or hemophilic mouse study, respectively) are drawn into a 1 mL syringe (charged with 50 or 30 μL of 3.8% Na-Citrate for normal or hemophilic mouse study, respectively) from the inferior vena cava at the indicated time point (one animal per sample). Plasma samples are assayed for FVIII concentration using the chromogenic assay method described above. PEGylated PEG6 shows greater plasma recovery compared to BDD or PEG6 (FIG. 21). PEGylated PEG2 shows greater plasma recovery compared to BDD (FIGS. 22 and 23).

TABLE 6

PK study summary of PEGylated FVIII showing plasma half-lives in hours.

| Construct | Half-life, hr | Species |
|---|---|---|
| BDD | 6.6 | Normal Rabbit |
| PEG2 | 4.8 | Normal Rabbit |
| PEG2-22 kD PEG | 7.5 | Normal Rabbit |
| PEG2-43 kD PEG | 8.0 | Normal Rabbit |
| PEG6-12 kD PEG | 8.2 | Normal Rabbit |
| PEG6-33 kD PEG* | 9.6 | Normal Rabbit |
| PEG6-33 kD PEG | 17.4 | Normal Rabbit |
| BDD | 4.5 | Normal Mouse |
| PEG2-22 kD PEG | 7.3 | Normal Mouse |
| PEG6-12 kD | 5.3 | Normal Mouse |
| PEG14-33 kD PEG | 7.3 | Normal Mouse |
| PEG14-12 kD PEG | 5.5 | Normal Mouse |
| PEG22-64 kD | 9.2 | Normal Mouse |

*Initial prep of 33 kD PEGylated PEG6 with half-life of 9.6 hr in rabbits was not as pure as a later prep that yielded 17.4 hr.

TABLE 7

Plasma recovery of PEGylated PEG muteins in hemophilic mice. Fold-improvement in plasma recovery at 16 hours post-injection compared to the BDD control performed on the same date is reported.

| Mutein | PEG | Fold |
|---|---|---|
| PEG 6 | 12 kD | 2.9 |
| PEG 6 | 33 kD | 2.9 |
| PEG 2 + 6 | 33 kD | 3.3 |
| PEG 14 | 33 kD | 2.5 |
| PEG 2 + 6 | 33 kD | 4.4 |
| PEG 2 + 14 | 33 kD | 2.1 |
| PEG22 | 64 kD | 3.2 |

Hemophilic Mouse (BDD) Factor VIII Recovery.

Figure 24:
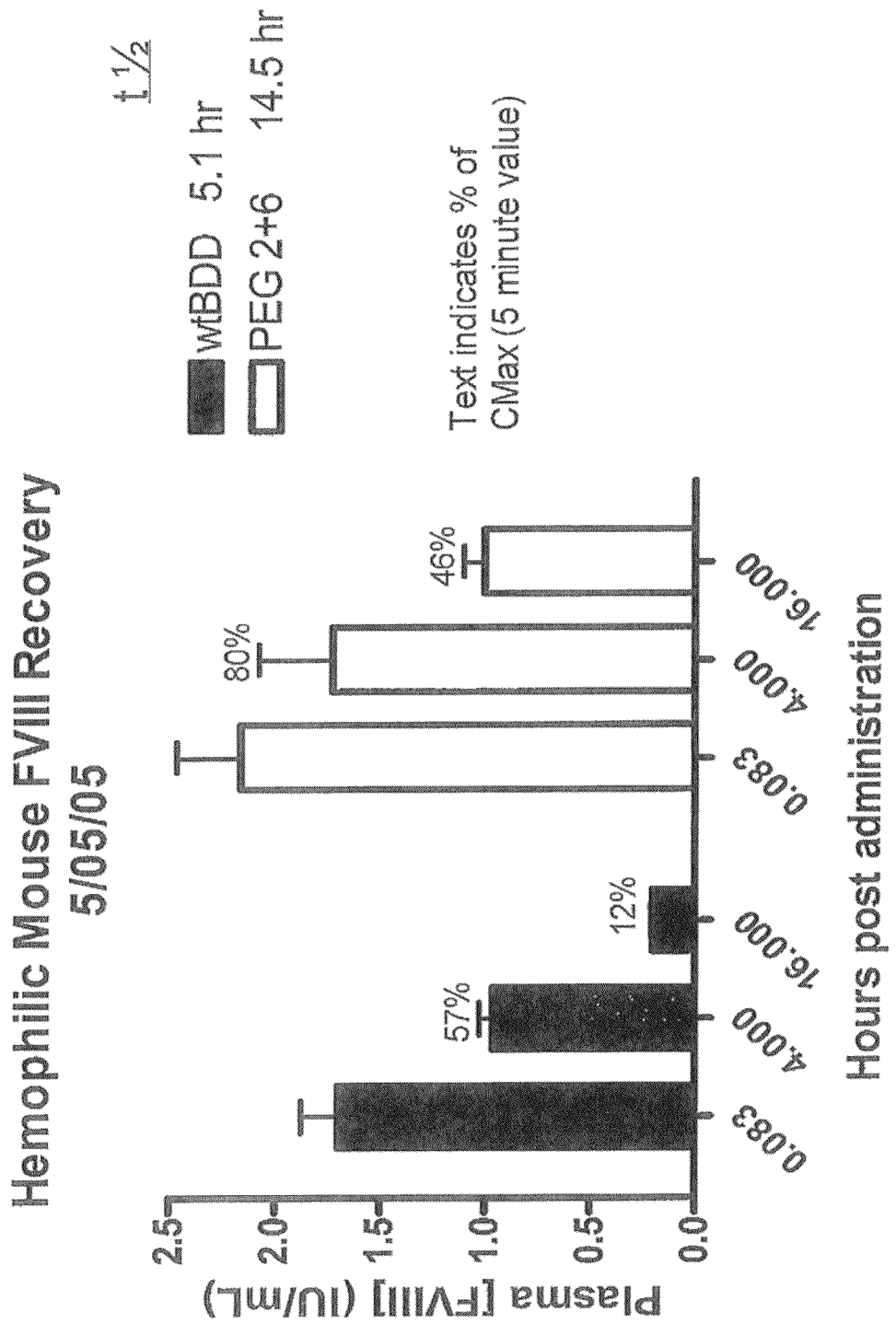
FIG. 24. The Hemophilic Mouse (BDD) Factor VIII recovery histogram depicting a pharmacokinetic (PK) assessment of the half-life of two species of BDD Factor VIII in a hemophilic mouse assay.

The Hemophilic Mouse (BDD) Factor VIII recovery histogram shown in FIG. 24 depicts a pharmacokinetic (PK) assessment of the half-life of two species of BDD Factor VIII in a hemophilic mouse assay. This assay was designed to measure plasma concentrations of both BDD Factor VIII (referred to in FIG. 24 as "wt" or wild type BDD Factor VIII) and the PEG 2+6 double PEGylated variant of BDD Factor VIII (and identified elsewhere herein as the L491C, K1808C double variant of BDD Factor VIII) at three time points post intravenous administration in a mouse model. While the PK assessments at both the 0.8 and 4 hour time points were comparable, the 16 hour assessment is particularly note worthy. At 16 hours, approximately four times (400%) as much of the doubly PEGylated BDD Factor VIII variant (PEG 2+6) remained in the mouse plasma 16 hours after administration as compared to the un-PEGylated molecule.

Kidney Laceration Model.

Figure 25:
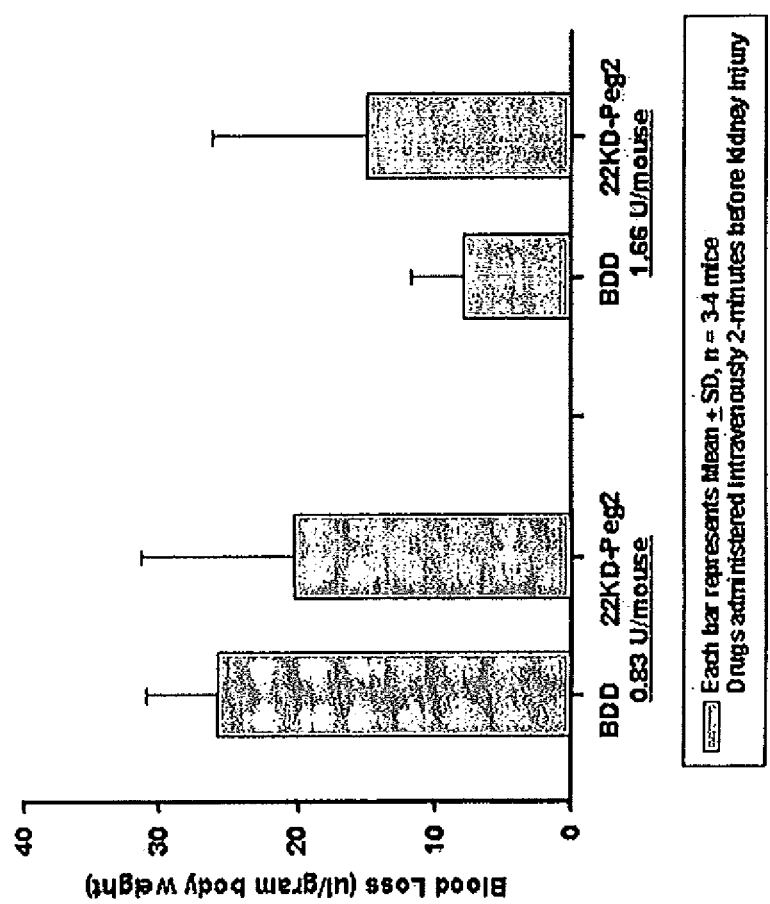
FIG. 25. Hemophilic mouse kidney laceration study of 22 kD PEGylated PEG2 compared to BDD. Vehicle treated mice have a blood loss of 25 uL/gram body weight.

To determine if PEGylated FVIII muteins were efficacious at stopping a bleed in a hemophilic mouse, the kidney laceration model was employed. Hemophilic mice (C57/BL6 with a disrupted FVIII gene) are anesthetized under isofluorane and weighed. The inferior vena cava was exposed and 100 ul of either saline or FVIII were injected using a 31 gauge needle. The needle was carefully removed and pressure applied at the sight of injection for 30-45 seconds to prevent bleeding. After two minutes, the right kidney was exposed and held between the forceps along the vertical axis. Using a #15 scalpel, the kidney was cut horizontally to a depth of 3 mm. To insure a uniform depth of the lesion, kidney was lightly held in the middle to expose equal tissue on either side of the forceps. The exposed surface of the kidney was cut to the depth of the forceps. Blood loss was quantified as described above. Different doses of FVIII were tested on mice to characterize the dose response relationship of FVIII on kidney bleeding. PEGylated PEG2 shows comparable potency to BDD in reducing blood loss after mouse kidney injury (FIG. 25). Thus, although the coagulation activity of PEGylated PEG2 is lower than that of BDD, this kidney laceration model shows that the in vivo efficacy of PEGylated PEG2 was not measurably reduced compared to BDD, consistent with the chromogenic assay data.

Antibody Inhibition Assay.

Figure 26:
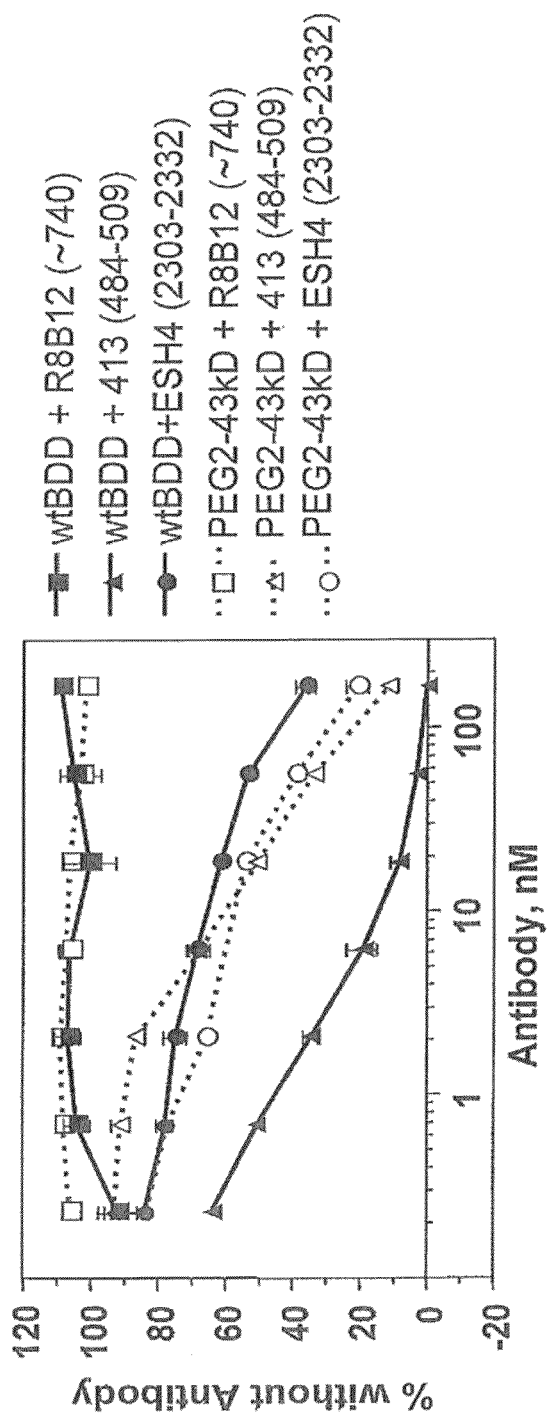
FIG. 26. Chromogenic Activity of PEGylated PEG2 and BDD in the presence of increasing amounts of FVIII antibodies. Antibody epitope is denoted in parenthesis.
Figure 27:
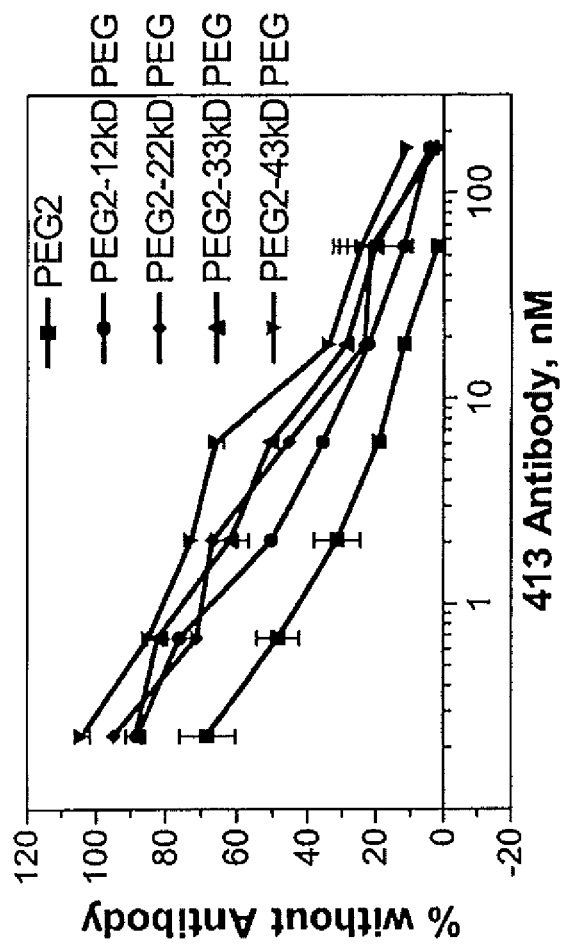
FIG. 27. Chromogenic Activity of PEGylated PEG2 in the presence of increasing amounts of FVIII mAB 413 antibodies.
Figure 28A:
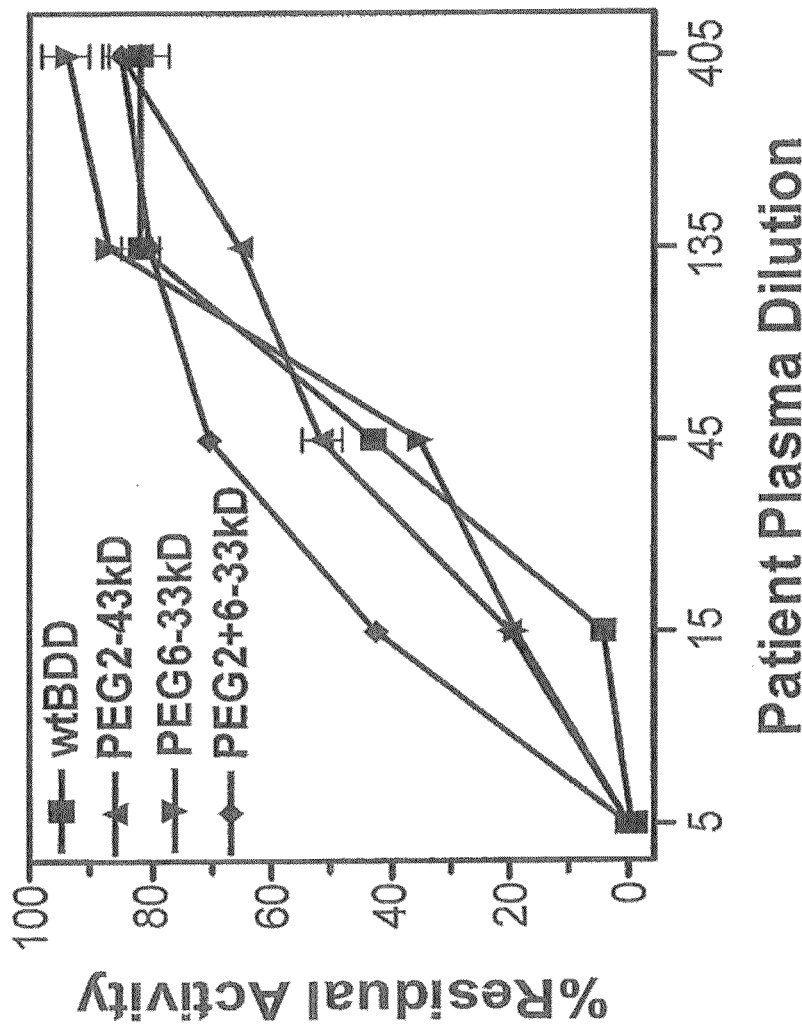
FIG. 28A-28D. Chromogenic activity of BDD, 43 kD PEGylated PEG2, 33 kD PEGylated PEG6, and 33 kD diPEGylated PEG2+6 in the presence of human plasma derived from patients that have developed inhibitors to FVIII. The inhibitor titer and date of blood collection were noted at the top.
Figure 28B:
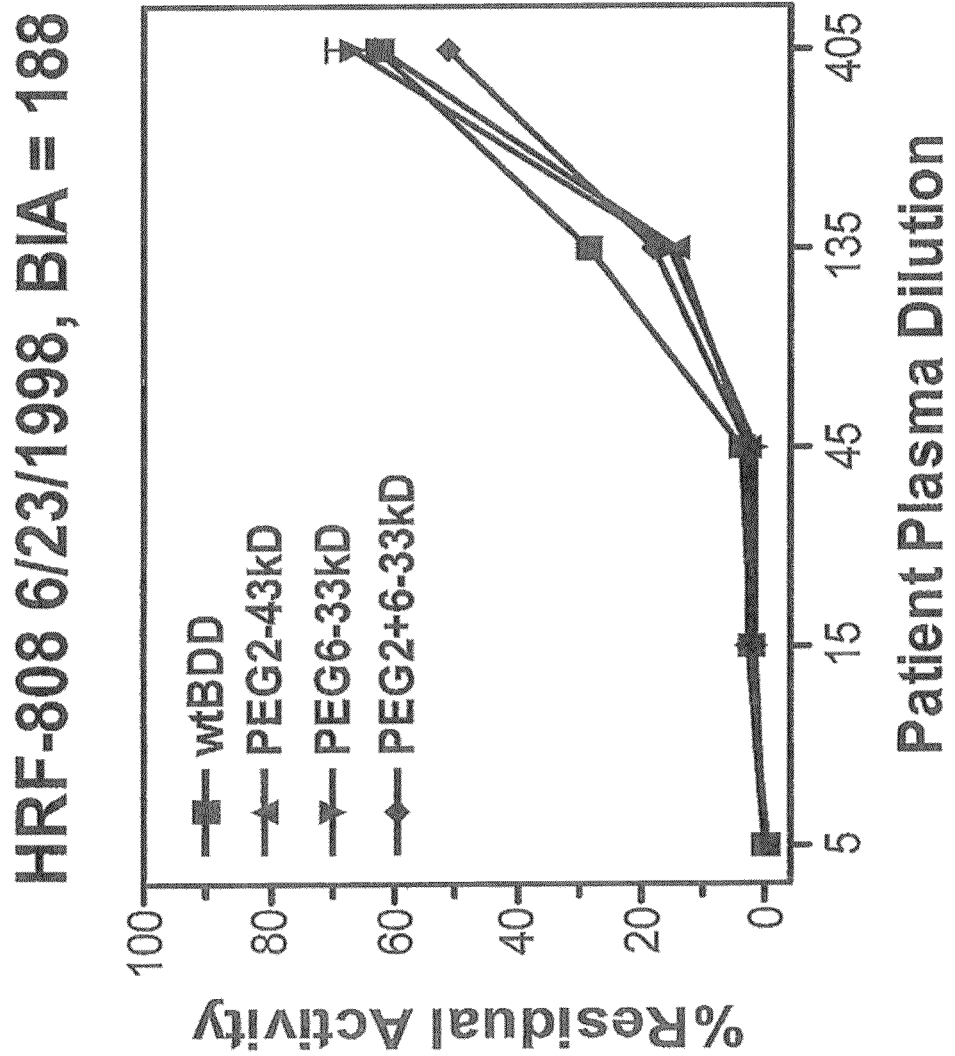
Figure 28C:
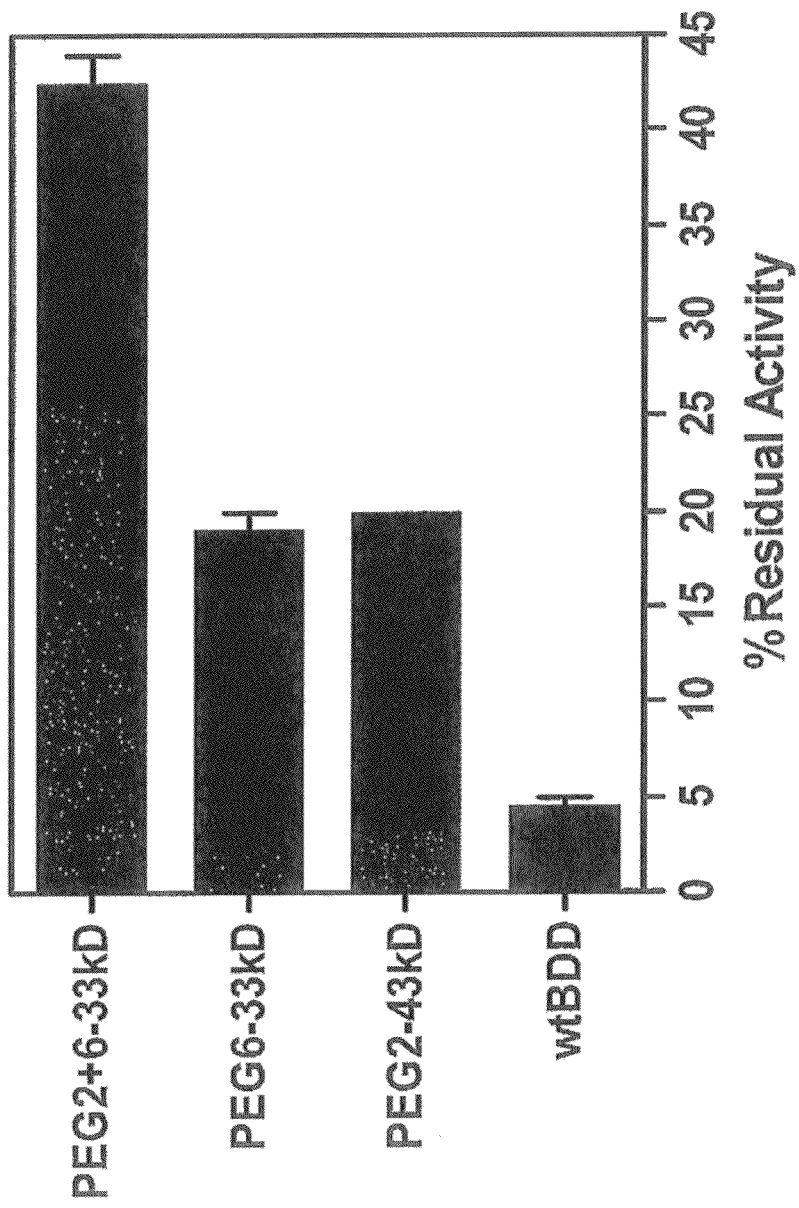
Figure 28D:
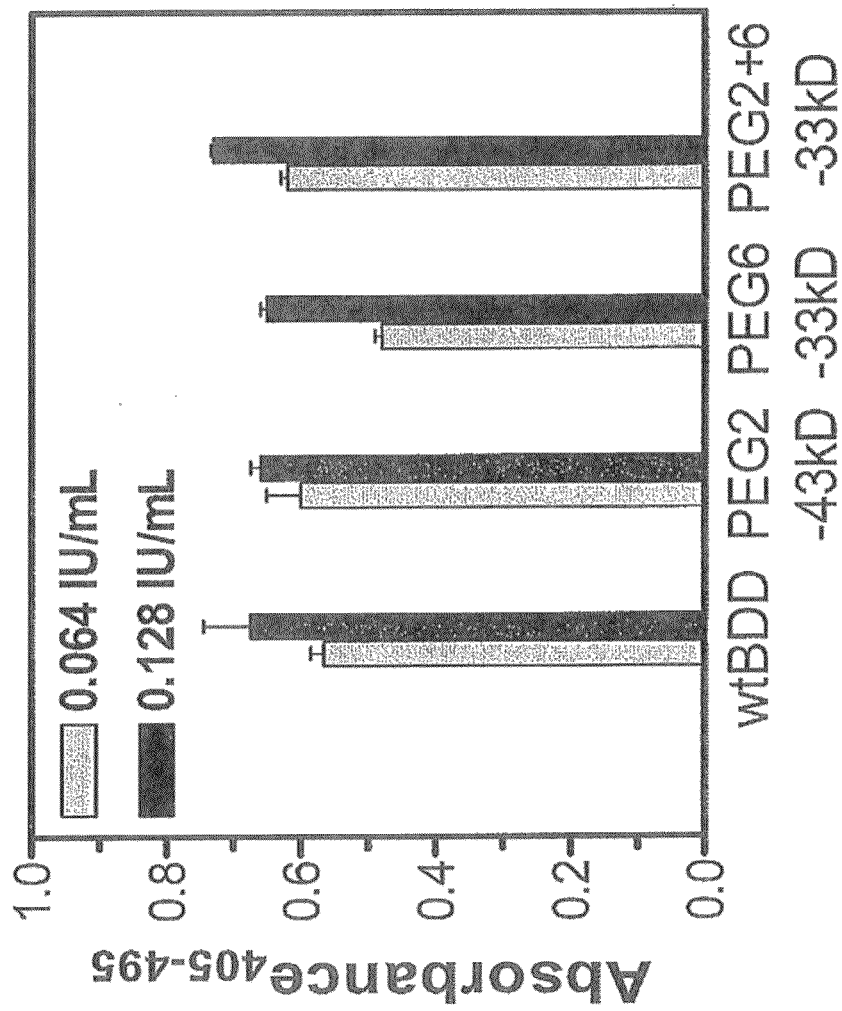

Adding a high molecular weight polymer such as polyethylene glycol (PEG) specifically at position 491 (i.e. PEG2) should reduce binding and sensitivity to mAB 413, and by extension to a large proportion of patient inhibitory antibodies since many patients develop inhibitor antibodies against the same mAB 413 epitope. To test this, increasing amounts of mAB 413 was incubated with non-saturating amounts (0.003 IU/mL) of BDD or 43 kD PEGylated PEG2 and tested for functional activity in a chromogenic assay (FIG. 26). R8B12, a non-inhibitory antibody, and ESH4, an inhibitory antibody that targets the C2 domain were used as controls. PEGylated PEG2 is indeed more resistant to mAB 413 inhibition than BDD and shows a similar inhibition pattern in the presence of the control antibodies that do not bind near the 491 position. Furthermore, the protection effect of PEG against mAB 413 inhibition is dependent on PEG size, with larger PEGs having a greater effect (FIG. 27). To test whether PEGylated FVIII is more resistant to inhibitor antibodies from patients, chromogenic activity was measured in the presence of a panel of plasma derived from hemophilia A patients who have developed inhibitors to FVIII. Of the 8 patient plasma tested, 43 kD PEGylated PEG2 was more resistant to patient plasma inhibition than BDD in 4 patient plasma samples. For example, PEGylated PEG2, PEG6, or PEG2+6 showed greater residual activity than BDD in one patient plasma but not in another plasma (FIG. 28). The diPEGylated PEG2+6 appears to be more resistant than monoPEGylated PEG2 or PEG6. These results suggest that PEGylated PEG muteins can be more effective in treating patients that develop inhibitors to FVIII.

High Throughput Pegylation Screening.

PEGylation efficiency of a particular PEG mutein is unpredictable, especially since there is no direct structural information of BDD. For example, based on the structure model of BDD, one would predict the PEGylation efficiency of PEG4 and PEG8 should be very high, similar to that of PEG2 and PEG15 since all three positions are surface exposed and point outwardly according to the structure. Thus, to use PEG to search for novel clearance mechanism via systematic PEGylation will require a large number of muteins to be screened.

Figure 29:
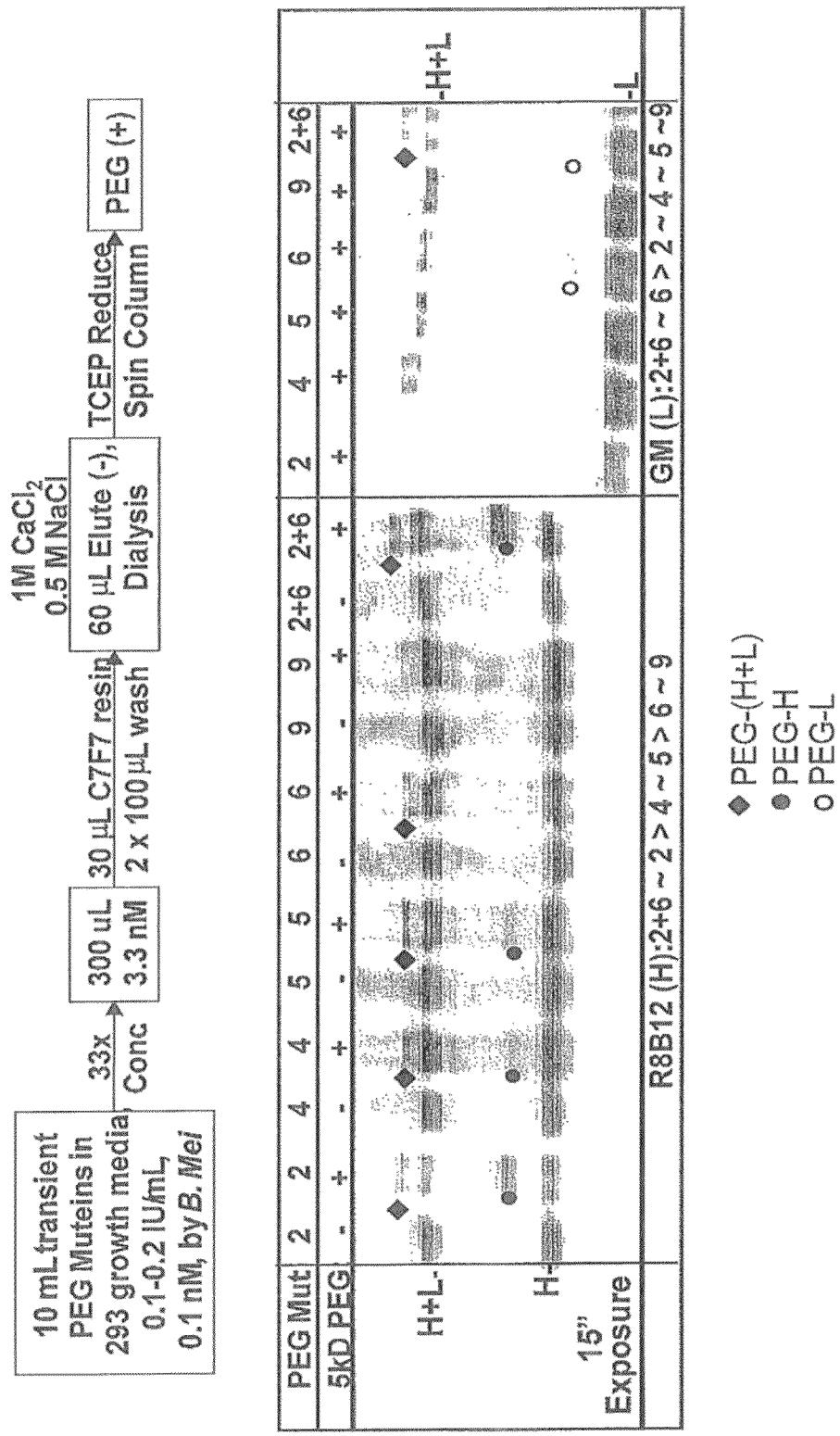
FIG. 29. PEGylation screening method and validation. Top panel shows a schematic of PEGylation screening of transiently expressed PEG muteins. Bottom panel shows a Western analysis of PEGylated products using a heavy chain ("H")-specific antibody (left) or a light-chain ("L") specific antibody (right). PEGylated bands are highlighted by dots. "U" is unprocessed material containing both H and L.
Figure 30:
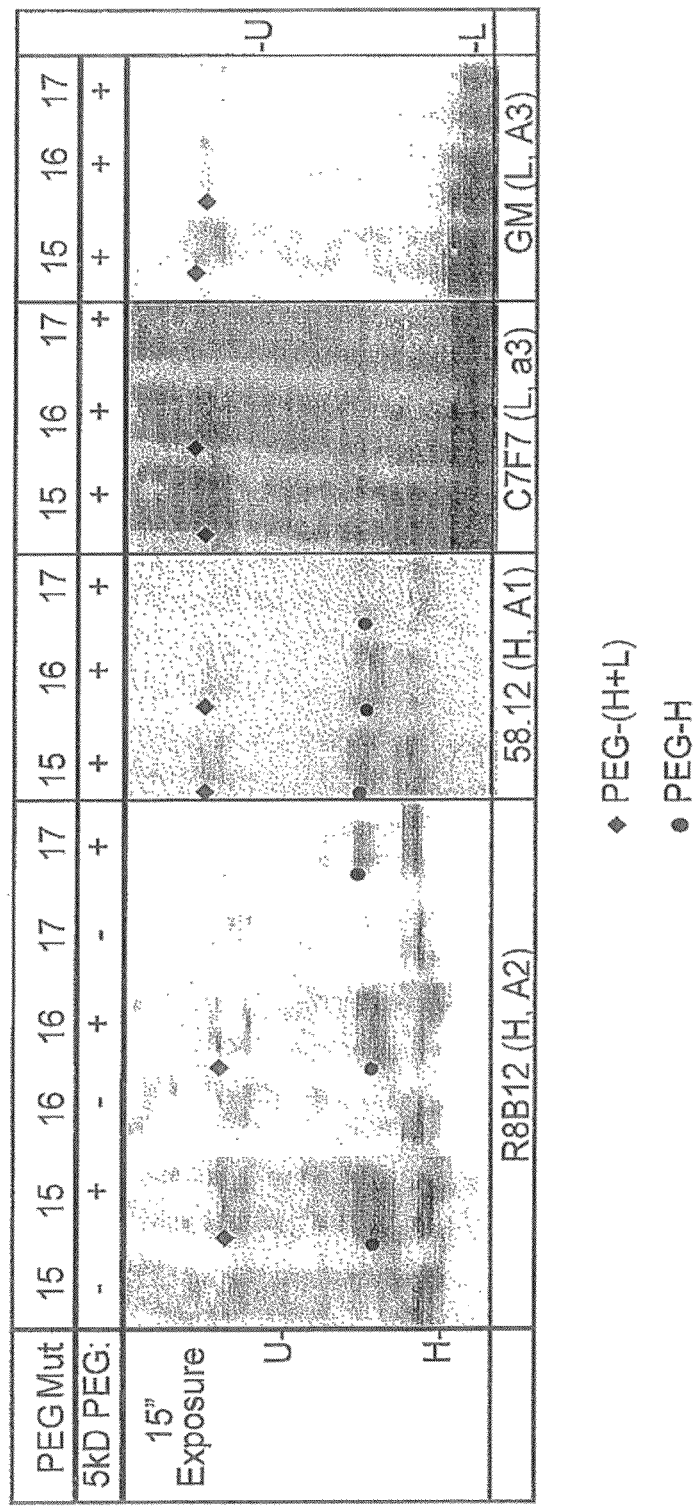
FIG. 30. PEGylation screening of PEG15-17. Western analysis of PEGylated products using heavy chain ("H")-specific antibodies (R8B12 and 58.12) or light-chain ("L") specific antibodies (C7F7 and GM). All 3 muteins are selective for the heavy chain, with relative PEGylation efficiency of PEG15~PEG16>PEG17. PEGylated bands are highlighted by dots. "U" is unprocessed material containing both H and L.

To rapidly screen a large number of PEG muteins, a novel high throughput method has been developed that can test PEGylation efficiency and functional activity of PEGylated products from transiently transfected muteins. As little as 5-10 mL of transiently expressed PEG muteins with an FVIII chromogenic value of as low as 0.1-0.2 IU/mL is concentrated by about 50-fold using Amicon-centra Ultra device MWCO 30K so that the concentration of FVIII reaches above 1 nM, near the affinity range of antibody to FVIII interaction. The concentrated PEG mutein (~300 uL) is incubated with ~30 uL of C7F7 FVIII antibody resin overnight at 4° C., washed, eluted, dialyzed, and reduced. The reductant is removed and the reduced PEG muteins is PEGylated and run on a Western analysis as described above (FIGS. 29 and 30). Relative PEGylation efficiency of transiently expressed PEG muteins matches exactly to that of purified PEG muteins.

Dozens of PEG muteins can be screened by this method in one to two months. For example, PEG14 (K1804C BDD) had at least about 80% PEGylation of light chain with a 12 kD PEG and no PEGylation of heavy chain (data not shown), consistent with the K1804C mutation located on the light chain. The Cα to Cβ distance between K1804 and K1808 (PEG6 position) is only 8.4 angstrom based on the BDD structure, suggesting that the introduction of a 43 kD PEG at this position will have similar improvement in PK as the 33 kD PEGylated PEG6, with the advantage of much higher PEGylation yield. Relative PEGylation yield for all PEG muteins tested are summarized in Table 8. PEGylation was highly selective for the particular FVIII chain where the cysteine mutation was introduced, in that every mutein with the cysteine in the heavy chain only gets PEGylated on the heavy chain while every mutein with the cysteine in the light chain gets PEGylated on the light chain. Mutein numbers 2 to 31 represent cysteine mutations of BDD replacing the native amino acid at the position listed with a cysteine. PEG2+6 is a double mutein of BDD where position 491 and 1808 were substituted with cysteines. A1 and A2, (and B domain for KG-2, the full-length FVIII) belong to the heavy chain while A3, C1, and C2 belong to the light chain. PEGylation efficiency was estimated from running the PEGylated products on a SDS PAGE comparing the intensities of the PEGylated band with unPEGylated band: +++~>80% PEGylation yield, ++~30-70% yield, +~10-30% yield, and −~<10% yield.

TABLE 8

PEGylation efficiency for various PEGylated FVIII.

| PEG Mutein | Position | Domain | H-PEG | L-PEG |
|---|---|---|---|---|
| 2 | 491 | A2 | +++ | − |
| 4 | 504 | A2 | + | − |
| 5 | 468 | A2 | + | − |
| 6 | 1808 | A3 | − | ++ |
| 7 | 1810 | A3 | − | ++ |
| 8 | 1812 | A3 | − | − |
| 9 | 1815 | A3 | − | − |
| 11 | 1795 | A3 | − | + |
| 12 | 1796 | A3 | − | + |
| 13 | 1803 | A3 | − | ++ |
| 14 | 1804 | A3 | − | +++ |
| 15 | 377 | A2 | +++ | − |
| 16 | 378 | A2 | +++ | − |
| 17 | 556 | A2 | ++ | − |
| 20 | 2118 | A3 | − | + |
| 21 | 81 | A1 | ++ | − |
| 22 | 129 | A1 | ++ | − |
| 23 | 422 | A2 | − | − |
| 25 | 570 | A2 | − | − |
| 26 | 1864 | A3 | − | ++ |
| 27 | 1911 | A3 | − | +++ |
| 28 | 2091 | C1 | − | ++ |
| 29 | 2284 | C2 | − | + |
| 30 | 711 | A2 | + | − |
| 31 | 1903 | A3 | − | ++ |
| 2 + 6 | 490/1808 | A2/A3 | +++ | ++ |
| 2 + 14 | 490/1804 | A2/A3 | +++ | +++ |
| KG-2 | | B | +++ | − |

Mass Spectrometry Analysis of Reduced PEG Muteins.

Figure 31:
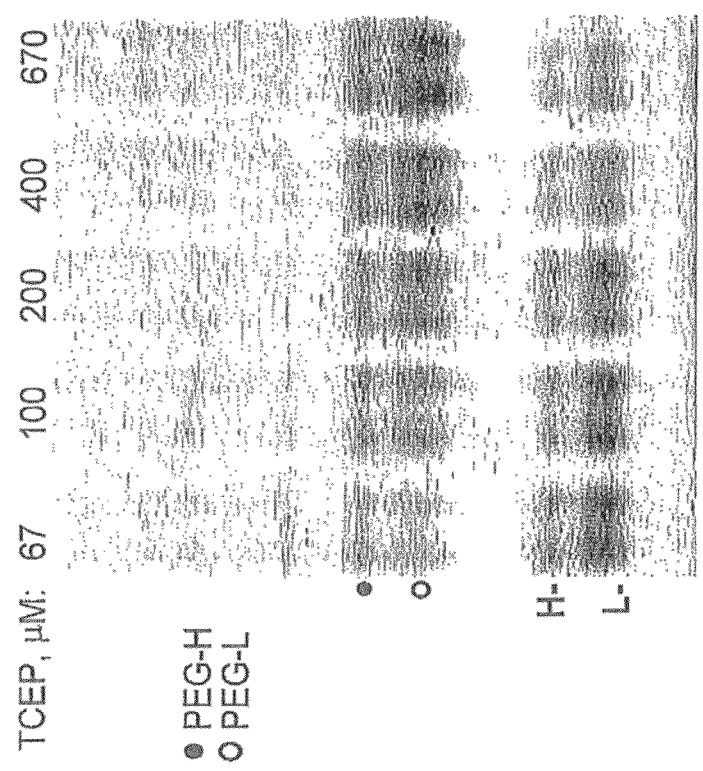
FIG. 31. Gel showing PEGylation of PEG2+14 as a function of reductant concentration. PEG2+14 was treated with 67 to 670 uM of TCEP for 30 minutes at 4° C. The reductant was removed by spin-column followed by PEGylation with a 12 kD PEG. Heavy and light chains of FVIII are highlighted by "H" and "L," respectively. The two dots point to the PEGylated heavy and light chains.
Figure 32A:
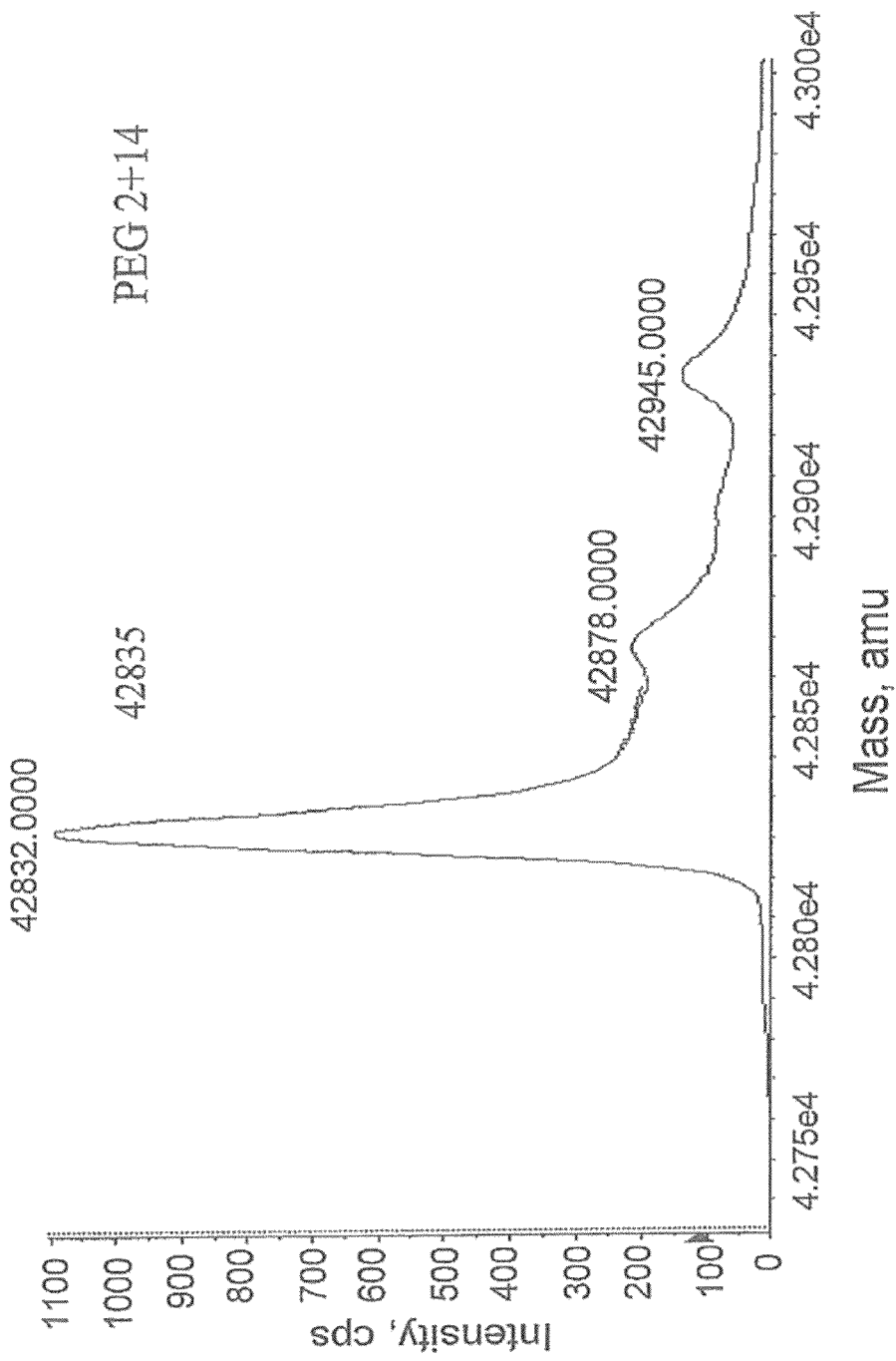
FIG. 32A-32F. Deconvoluted Mass Spectra of PEG2+14 treated with 67 to 670 uM of TCEP followed by reductant removal.
Figure 32B:
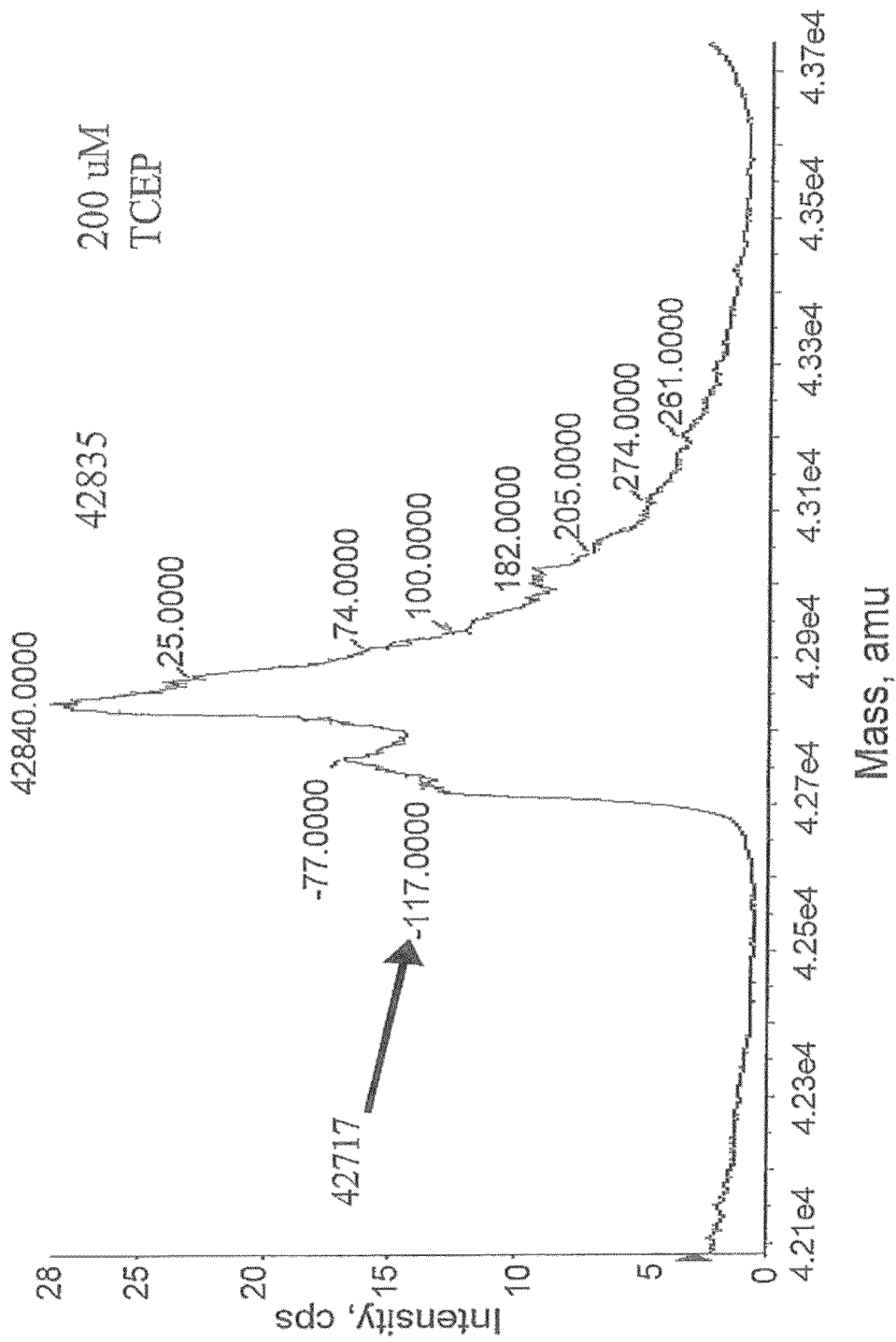
Figure 32C:
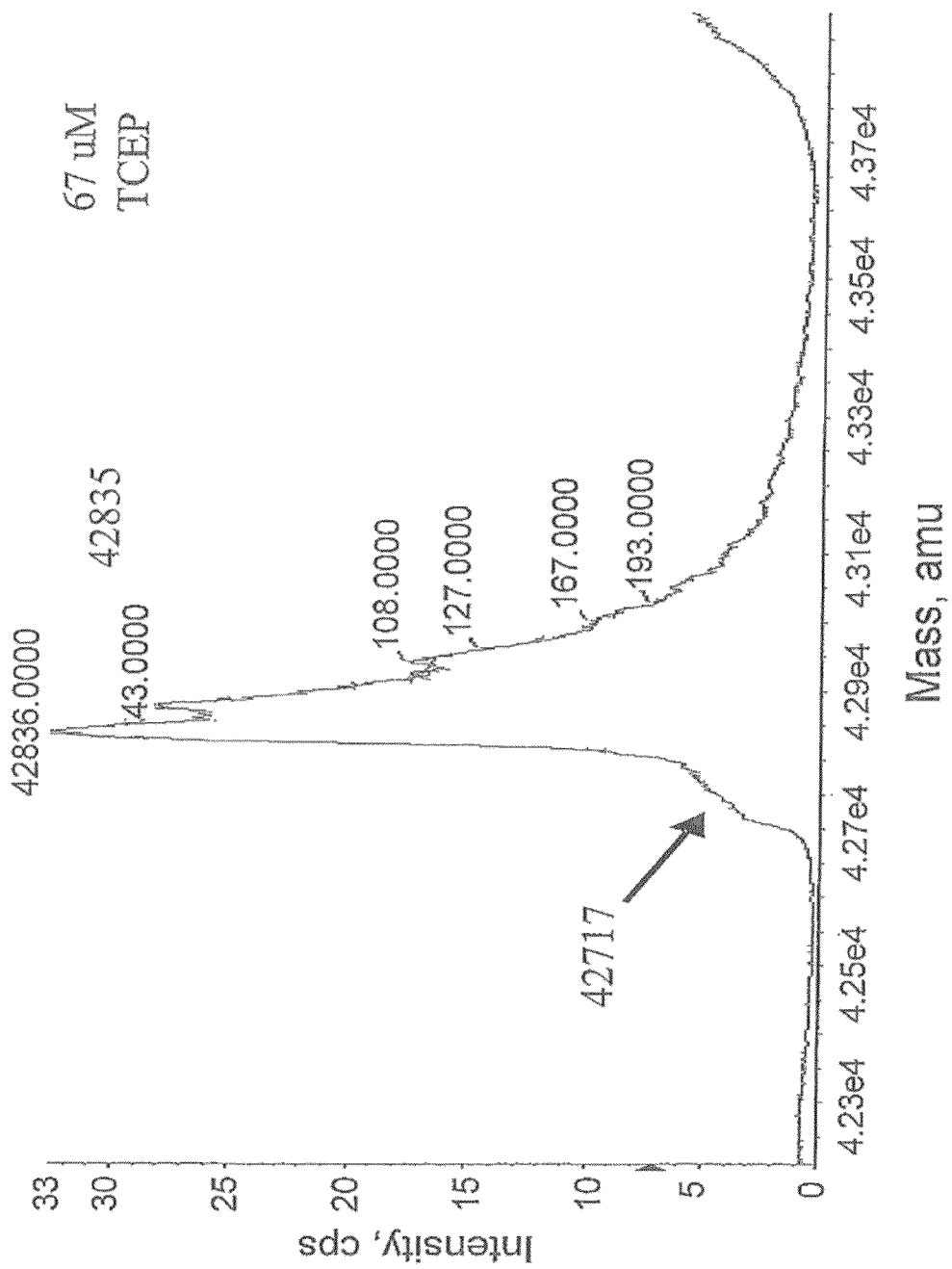
Figure 32D:
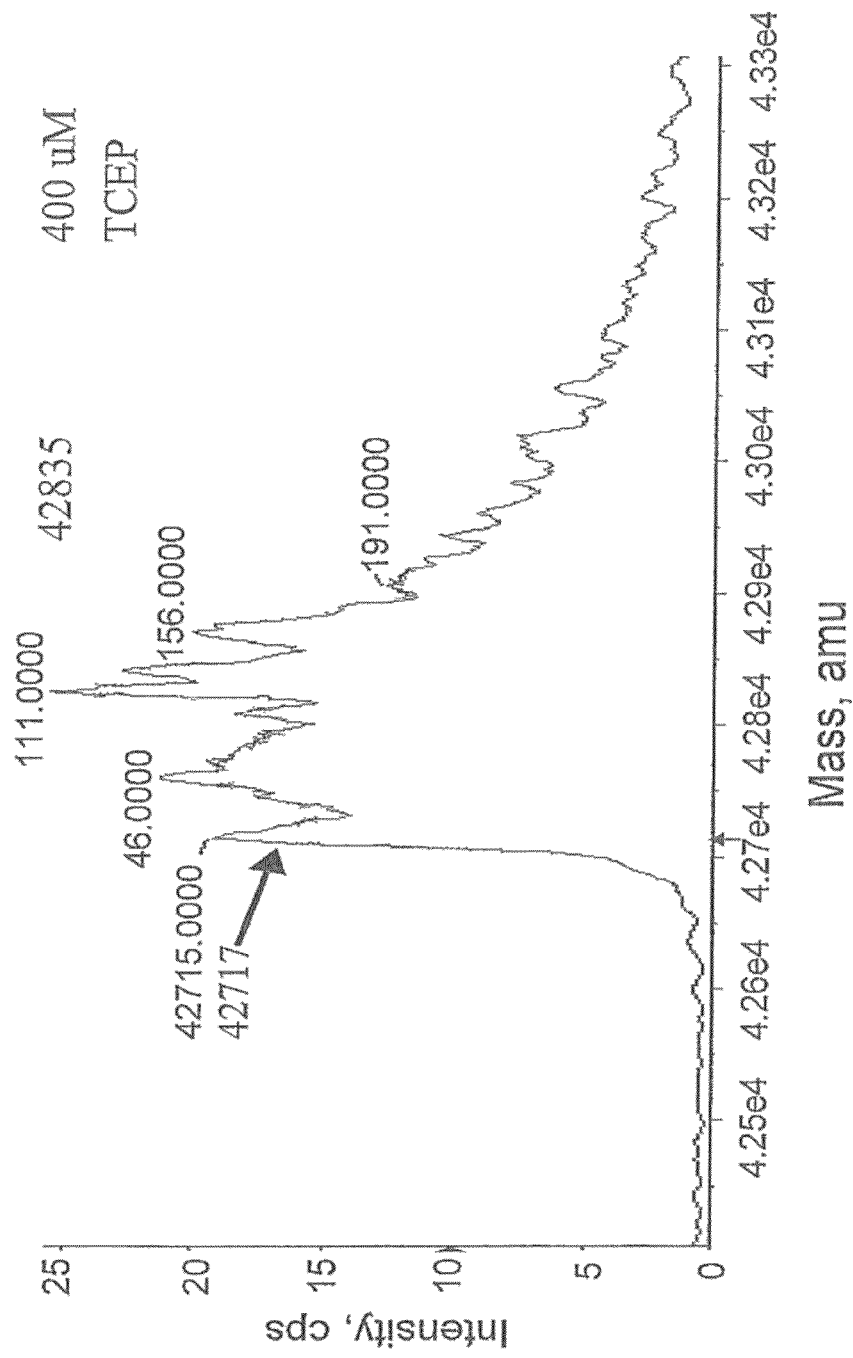
Figure 32E:
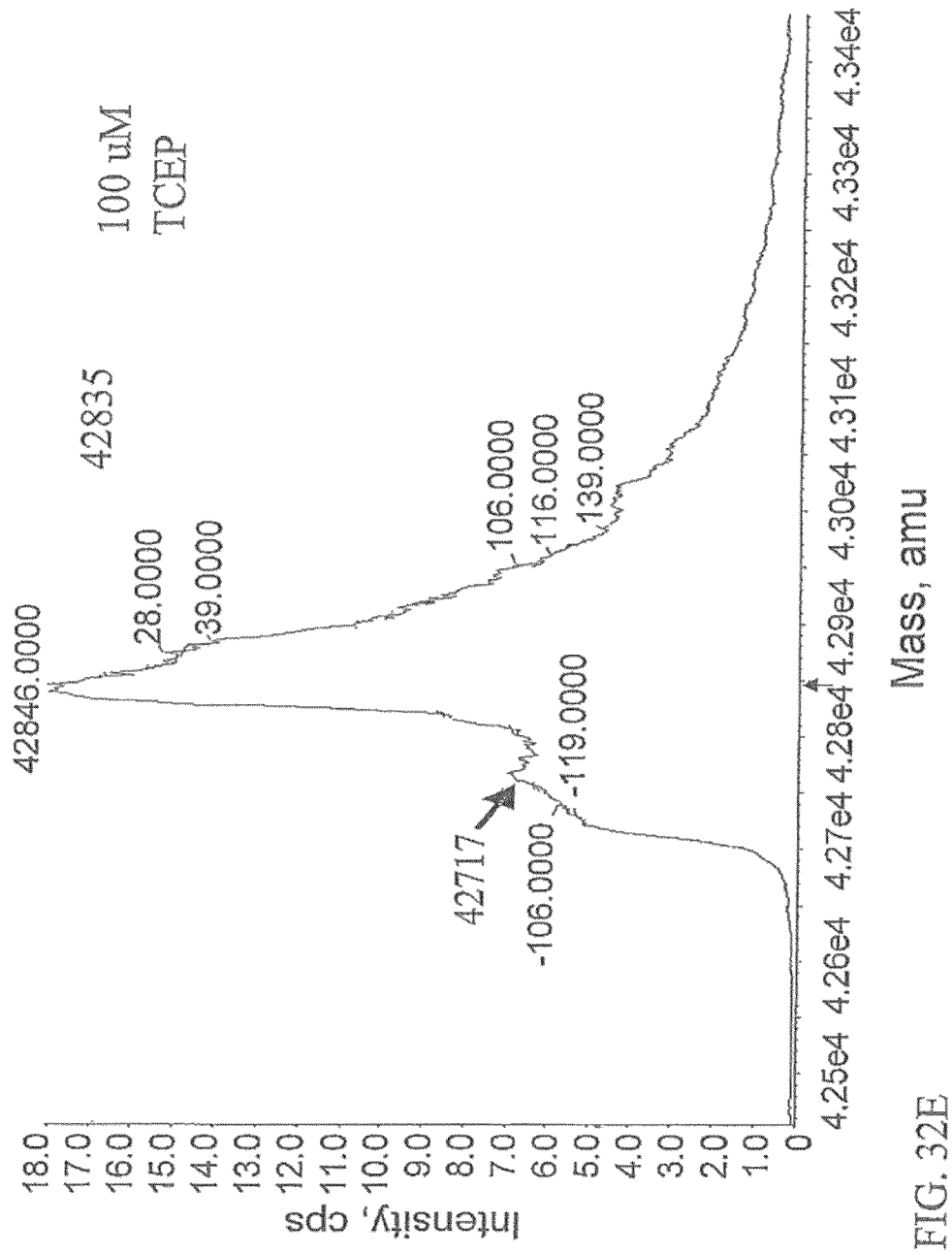
Figure 32F:
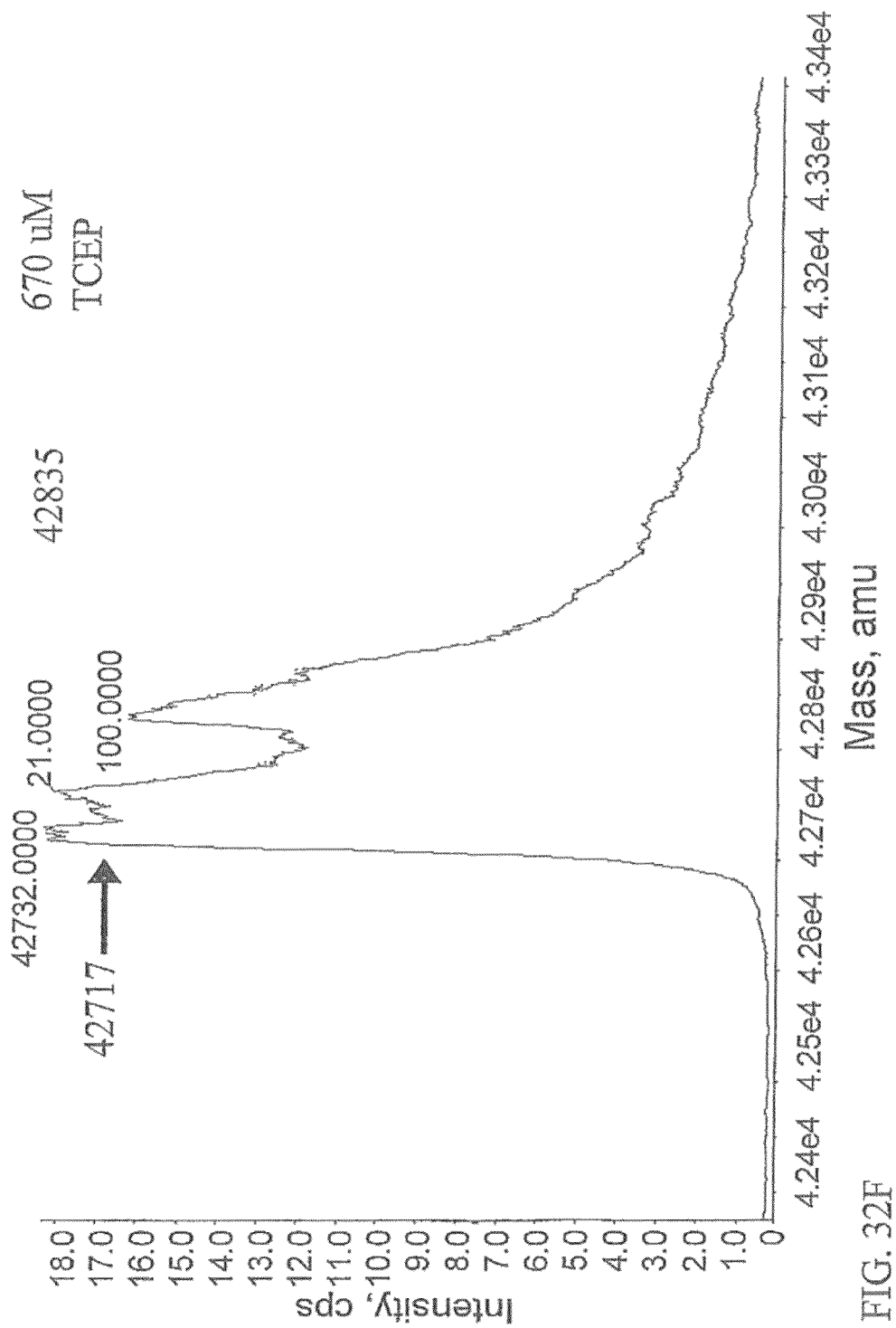

To determine the identity of the "cap" that prevents direct PEGylation of PEG muteins or full-length FVIII, PEG2+14 was reduced with TCEP at concentrations ranging from 67 uM to 670 uM. PEGylation yield increased in proportion to increasing amounts of TCEP (FIG. 31). The same samples were also analyzed by mass spectrometry prior to PEGylation (FIG. 32). In order to have a protein domain that could be directly studied, the samples were digested with thrombin at a ratio of 20 units/mg FVIII for 30 minutes at 37° C. Thrombin cleavage produces an A2 fragment that includes residues 372 to 740 and no occupied glycosylation sites. The digested sample was injected onto a C4 reversed phase liquid chromatography system and the eluent from the column was introduced directly into the quadrupole time-of-flight mass spectrometer via an electrospray interface. The mass spectrum from under the chromatographic peak corresponding to the A2 domain was deconvoluted to provide a protein intact mass value. Prior to reduction, the A2 domain of PEG2+14 yields a mass that is 118 daltons larger than theoretically predicted. As the TCEP concentration is increased, a new peak that has the precise predicted mass of A2 domain appears. The proportion of this new peak increases as the TCEP concentration is increased. The 118 dalton difference can be accounted for by cysteinylation at residue Cys 491 via disulfide formation with a cystine (119 Da) and instrumental accuracy. Thus this shows that the PEG muteins are capped by a cysteine, which prevents direct PEGylation.

All of the references disclosed herein are hereby incorporated herein in their entireties.

We claim:

1. A pharmaceutical composition comprising pharmaceutically acceptable adjuvants and a therapeutically effective amount of factor VIII conjugates;
    wherein the factor VIII conjugates have factor VIII procoagulant activity and consist of a functional factor VIII polypeptide having a heavy and a light chain in which one or more biocompatible polymers are covalently attached to the functional factor VIII polypeptide at only the heavy chain;
    wherein the functional factor VIII polypeptide comprises the amino acid sequence of SEQ ID NO: 4 or an allelic variant thereof; and
    wherein the one or more biocompatible polymers comprise polyalkylene oxide.

2. The pharmaceutical composition of claim 1, wherein the biocompatible polymer comprises polyethylene glycol.

3. The pharmaceutical composition of claim 2, wherein the polyethylene glycol comprises methoxypolyethylene glycol.

4. The pharmaceutical composition of claim 3, wherein the methoxypolyethylene glycol has a size range of from 5 kD to 64 kD.

5. The pharmaceutical composition of claim 1, wherein the functional factor VIII polypeptide is covalently attached to only one biocompatible polymer and the biocompatible polymer is polyethylene glycol.

6. The pharmaceutical composition of claim 5, wherein the polyethylene glycol is attached to the functional factor VIII polypeptide at amino acid position 711.

7. A pharmaceutical composition consisting essentially of pharmaceutically acceptable adjuvants and a therapeutically effective amount of factor VIII conjugates;
    wherein the factor VIII conjugates have factor VIII procoagulant activity and consist of a functional factor VIII polypeptide having a heavy and a light chain in which one or more biocompatible polymers are covalently attached to the functional factor VIII polypeptide at only the heavy chain;
    wherein the functional factor VIII polypeptide comprises the amino acid sequence of SEQ ID NO: 4 or an allelic variant thereof; and
    wherein the one or more biocompatible polymers comprise polyalkylene oxide.

8. The pharmaceutical composition of claim 7, wherein the biocompatible polymer comprises polyethylene glycol.

9. The pharmaceutical composition of claim 8, wherein the polyethylene glycol comprises methoxypolyethylene glycol.

10. The pharmaceutical composition of claim 9, wherein the methoxypolyethylene glycol has a size range of from 5 kD to 64 kD.

11. The pharmaceutical composition of claim 9, wherein the methoxypolyethylene glycol has a size range of from 5 kD to 43 kD.

12. The pharmaceutical composition of claim 7, wherein the functional factor VIII polypeptide is covalently attached to only one biocompatible polymer and the biocompatible polymer is polyethylene glycol.

13. The pharmaceutical composition of claim 12, wherein the polyethylene glycol is attached to the functional factor VIII polypeptide at amino acid position 711.

14. A pharmaceutical composition consisting of pharmaceutically acceptable adjuvants and a therapeutically effective amount of factor VIII conjugates;

wherein the factor VIII conjugates have factor VIII procoagulant activity and consist of a functional factor VIII polypeptide having a heavy and a light chain in which one or more biocompatible polymers are covalently attached to the functional factor VIII polypeptide at only the heavy chain;

wherein the functional factor VIII polypeptide comprises the amino acid sequence of SEQ ID NO: 4 or an allelic variant thereof; and wherein the one or more biocompatible polymers comprise polyalkylene oxide.

15. The pharmaceutical composition of claim 14, wherein the biocompatible polymer comprises polyethylene glycol.

16. The pharmaceutical composition of claim 15, wherein the polyethylene glycol comprises methoxypolyethylene glycol.

17. The pharmaceutical composition of claim 16, wherein the methoxypolyethylene glycol has a size range of from 5 kD to 64 kD.

18. The pharmaceutical composition of claim 16, wherein the methoxypolyethylene glycol has a size range of from 5 kD to 43 kD.

19. The pharmaceutical composition of claim 14, wherein the functional factor VIII polypeptide is covalently attached to only one biocompatible polymer and the biocompatible polymer is polyethylene glycol.

20. The pharmaceutical composition of claim 18, wherein the polyethylene glycol is attached to the functional factor VIII polypeptide at amino acid position 711.

* * * * *